US008748656B2

(12) United States Patent
Kong et al.

(10) Patent No.: US 8,748,656 B2
(45) Date of Patent: Jun. 10, 2014

(54) METHODS, COMPOUNDS, COMPOSITIONS AND VEHICLES FOR DELIVERING 3-AMINO-1-PROPANESULFONIC ACID

(75) Inventors: Xianqi Kong, Dollard-des-Ormeaux (CA); Mohamed Atfani, Laval (CA); Benoit Bachand, St-Laurent (CA); Abderrahim Bouzide, Laval (CA); Stéphane Ciblat, Montreal (CA); Sophie Levesque, Mirabel (CA); David Migneault, Laval (CA); Isabelle Valade, Laval (CA); Xinfu Wu, Laval (CA); Daniel Delorme, St-Lazare (CA)

(73) Assignee: BHI Limited Partnership, Laval, Quebec (CA)

( * ) Notice: Subject to any disclaimer, the term of this patent is extended or adjusted under 35 U.S.C. 154(b) by 429 days.

(21) Appl. No.: 11/871,639

(22) Filed: Oct. 12, 2007

(65) Prior Publication Data
US 2008/0146642 A1 Jun. 19, 2008

Related U.S. Application Data

(60) Provisional application No. 60/851,039, filed on Oct. 12, 2006, provisional application No. 60/911,459, filed on Apr. 12, 2007.

(51) Int. Cl.
*C07C 309/15* (2006.01)
*C07C 309/24* (2006.01)
*A61K 38/05* (2006.01)
*A61K 38/06* (2006.01)

(52) U.S. Cl.
USPC ............ 562/105; 562/42; 562/106; 514/21.9; 514/21.92

(58) Field of Classification Search
USPC ................. 562/42, 105, 106; 514/21.9, 21.92
See application file for complete search history.

(56) References Cited

U.S. PATENT DOCUMENTS

| 3,298,937 | A | | 1/1967 | Strauss et al. |
|---|---|---|---|---|
| 3,755,446 | A | | 8/1973 | Scheuermann et al. |
| 3,793,079 | A | | 2/1974 | Brown et al. |
| 4,472,392 | A | | 9/1984 | Anderson et al. |
| 4,521,619 | A | | 6/1985 | Kaplan |
| 4,563,470 | A | | 1/1986 | Durlach |
| 4,795,595 | A | * | 1/1989 | Agnes et al. ............... 548/497 |
| 4,812,512 | A | | 3/1989 | Buendia et al. |
| 5,091,432 | A | | 2/1992 | Glasky |
| 5,622,934 | A | | 4/1997 | Frick et al. |
| 5,643,562 | A | | 7/1997 | Kisilevsky et al. |
| 5,728,375 | A | | 3/1998 | Kisilevsky et al. |
| 5,776,970 | A | | 7/1998 | Shechter et al. |
| 5,840,294 | A | | 11/1998 | Kisilevsky et al. |
| 5,952,389 | A | | 9/1999 | Fogel |
| 5,972,328 | A | | 10/1999 | Kisilevsky et al. |
| 6,057,373 | A | | 5/2000 | Fogel |
| 6,166,086 | A | | 12/2000 | Taub |
| 6,265,437 | B1 | | 7/2001 | Berthelon et al. |
| 6,294,583 | B1 | | 9/2001 | Fogel |
| 6,297,226 | B1 | | 10/2001 | Glasky |
| 6,414,114 | B2 | | 7/2002 | Taub et al. |
| 6,451,853 | B1 | | 9/2002 | Taub et al. |
| 6,455,589 | B1 | | 9/2002 | Ames et al. |
| 6,818,787 | B2 | | 11/2004 | Gallop |
| 6,989,401 | B2 | | 1/2006 | Maeda et al. |
| 7,186,855 | B2 | | 3/2007 | Gallop |
| 7,253,306 | B2 | | 8/2007 | Kong et al. |
| 7,414,076 | B2 | | 8/2008 | Kong et al. |
| 7,991,569 | B2 | | 8/2011 | Kataoka |
| 8,642,801 | B2 | * | 2/2014 | Kong et al. ............. 562/44 |
| 2003/0176486 | A1 | | 9/2003 | Maeda et al. |
| 2004/0198832 | A1 | | 10/2004 | Szarek et al. |
| 2004/0220138 | A1 | | 11/2004 | Gervais et al. |
| 2005/0142191 | A1 | | 6/2005 | Legore |
| 2006/0046967 | A1 | | 3/2006 | Satyam |
| 2006/0111439 | A1 | | 5/2006 | Gallop |
| 2006/0205674 | A2 | | 9/2006 | Satyam |
| 2007/0010573 | A1 | | 1/2007 | Kong et al. |

FOREIGN PATENT DOCUMENTS

| CA | 1051802 | 4/1979 |
|---|---|---|
| CA | 1095306 | 2/1981 |
| EP | 208599 | 1/1987 |
| EP | 1 306 367 A | 5/2003 |
| JP | 51-4121 | 1/1976 |
| JP | 54-106560 | 8/1979 |
| JP | 59-21666 | 2/1984 |
| JP | 59-108758 | 6/1984 |
| JP | 59-137500 | 8/1984 |
| JP | 04-163311 | 6/1992 |
| JP | 05-508390 | 11/1993 |
| JP | 53-12812 | 11/1993 |
| JP | 06-138110 | 5/1994 |
| JP | 06-184089 | 7/1994 |
| JP | 09-178755 | 7/1997 |
| JP | 10-204476 | 8/1998 |
| JP | 2002-503700 | 2/2002 |
| JP | 2002-509104 | 3/2002 |
| JP | 2003-515530 | 5/2003 |
| JP | 2005-200314 | 7/2005 |

(Continued)

OTHER PUBLICATIONS

Definition of amino acid residue, IUPAC Gold Book, IUPAC Compendium of Chemical Terminology, 1997, 2nd edition.*
Entry for solvate, Free Dictionary, http://www.thefreedictionary.com/solvate, accessed online on Jul. 21, 2009.*
Vippagunta et al. Advanced Drug Delivery Reviews, 2001, 48, p. 3-26.*
Brittain, H.G. Polymorphism in Pharmaceutical Solids, 1999, p. 202-208 and 219.*
Marnela et al., J. Neurochem., 1984, 43(6), p. 1650-1653.*
Sawada et al., J. Pharm. Exp. Ther., 1999, 291, p. 705-709.*

(Continued)

*Primary Examiner* — Shaojia Anna Jiang
*Assistant Examiner* — Jonathan S Lau
(74) *Attorney, Agent, or Firm* — Cooley LLP

(57) ABSTRACT

The invention relates to methods, compounds, compositions and vehicles for delivering 3-amino-1-propanesulfonic acid (3APS) in a subject, preferably a human subject. The invention encompasses compounds that will yield or generate 3APS, either in vitro or in vivo. Preferred compounds include amino acid prodrugs of 3APS for use, including but not limited to, the prevention and treatment of Alzheimer's disease.

14 Claims, No Drawings

(56) References Cited

FOREIGN PATENT DOCUMENTS

| WO | WO 91/14434 | | 10/1991 |
|---|---|---|---|
| WO | WO 94/13655 | | 6/1994 |
| WO | WO 94/22437 | A2 | 10/1994 |
| WO | WO 96/28187 | A1 | 9/1996 |
| WO | WO 99/37606 | | 7/1999 |
| WO | WO 99/40909 | A1 | 8/1999 |
| WO | WO 99/59571 | A2 | 11/1999 |
| WO | WO 00/64420 | | 11/2000 |
| WO | WO 00/68263 | | 11/2000 |
| WO | WO 01/30979 | | 5/2001 |
| WO | WO 01/39796 | | 6/2001 |
| WO | WO 01/66533 | | 9/2001 |
| WO | WO 01/85093 | | 11/2001 |
| WO | WO 02/06214 | | 1/2002 |
| WO | WO 02/07781 | | 1/2002 |
| WO | WO 02/096937 | A | 12/2002 |
| WO | WO 2004/058239 | | 7/2004 |
| WO | WO 2004/112762 | | 12/2004 |
| WO | WO 2004/113275 | A | 12/2004 |
| WO | WO 2004/113277 | | 12/2004 |
| WO | WO 2004/113391 | A2 | 12/2004 |
| WO | WO 2006/059252 | | 6/2006 |
| WO | WO 2006/085149 | | 8/2006 |
| WO | WO 2007/049098 | | 5/2007 |
| WO | WO 2007/069073 | | 6/2007 |

OTHER PUBLICATIONS

Varga V. et al. "Modulation of Gabaergic Neurotransmission in the Brain by Dipeptides," Neurochemical Research, Plenum Press, New York, US, vol. 13, No. 11, Nov. 1, 1088, pp. 1027-1034, XP00906538, ISSN: 0364-3190.

Gervais, Francine et al., "Proteoglycans and Amyloidogenic Proteins in Peripheral Amyloidosis." Curr. Med. Chem.—Immun. Endoc. & Metab. Agents, 3:361-370, 2003.

Zeid, Ibrahim, et al., "Synthesis of N-substituted aminosulphonic acids," Chemistry and Industry, Apr. 21, 1973, 380.

Tokuda Toshimasa—Flame-Retardant Polycarbonate Resin Composition—Patent Abstracts of Japan—Publication No. 54-106560—Date of Publication: Aug. 21, 1979.

Sano Hirofumi et al. ,—"Production Of Hot Water-Resistant Polyvinyl Alcohol-Based Fiber", Patent Abstracts of Japan—Publication No. 04-163311, Date of Publication: Jun. 8, 1992.

Hattori Takatoshi—"Separator Column For Ion Chromatography", Patent Abstracts of Japan—Publication No. 06-138110—Date of Publication: May 20, 1994.

Takahashi Masakatsu—"New Gluocoaminosulfonic Acid Compound and Its Production and Surfactant Composition Containing the Same", Patent Abstracts of Japan—Publication No. 06-184089, Date of Publication: Jul. 5, 1994.

Kadota Akira et al., "Method and Reagent for Determining Bilirubin", Patent Abstracts of Japan—Publication No. 09-178755, Date of Publication: Jul. 11, 1997.

Tsubone Kazuyuki, "Surfactant", Patent Abstracts of Japan—Publication No. 10-204476, Date of Publication: Aug. 4, 1998.

Maeda Kazuhiro et al., "Method for Producing Sulfonic Acid Derivatives of Hydroxamic Acid", Patent Abstracts of Japan—Publication No. 2005-200314, Date of Publication: Jul. 28, 2005.

Espacenet Bibliographic data: JP2002509104 (A)—Mar. 26, 2002—"Methods of Treating Tardive Dyskinesia and Other Movement Disorders".

Espacenet Bibliographic data: JP2002503700 (A)—Feb. 5, 2002—"Novel Disulfides and Thiol Compounds".

Espacenet Bibliographic data: WO0206214 (A1)—Jan. 24, 2002—"Sulfonic Acid Derivatives of Hydroxamic Acids and Their Use as Medicinal Products".

Hisao Hirai et al., "Synthesis and Some Surface Active Properties of Fatty Derivatives of Propane Sultone", Sep. 15, 1966, pp. 469-474.

Noriyoshi Masuoka et al., "Preparation of a Volatile Derivative of Taurine and Application to Gas Chromatographic Determination of Urinary Taurine", Acta Med Okayama 43 (5) pp. 253-259 (1989).

Wada Morihiro et al., "M Protein Detecting Method for Serum Protein Fraction", Patent Abstract of Japan—Publication No. JP5312812—Publication Date: Nov. 26, 1993.

* cited by examiner

METHODS, COMPOUNDS, COMPOSITIONS AND VEHICLES FOR DELIVERING 3-AMINO-1-PROPANESULFONIC ACID

RELATED APPLICATION

This application claims priority from U.S. provisional patent application no. U.S. 60/851,039 filed Oct. 12, 2006, and U.S. provisional patent application no. U.S. 60/911,459 filed Apr. 12, 2007, which are incorporated herein by reference.

FIELD OF THE INVENTION

The invention relates to methods, compounds, compositions and vehicles for delivering 3-amino-1-propanesulfonic acid (3APS) in a subject, preferably a human subject. The invention encompasses compounds that will yield or generate 3APS, either in vitro or in vivo. Preferred compounds include amino acid prodrugs of 3APS for use, including but not limited to, the prevention and treatment of Alzheimer's disease.

BACKGROUND OF THE INVENTION

Alzheimer's disease (AD) is a progressive degenerative disease of the brain primarily associated with aging. Prevalence of AD in the United States in 2000 was close to 4.5 Million. It was estimated that about one in ten individuals over 65 and nearly half of those over 85 are affected by Alzheimer's disease. Approximately 360,000 patients will be diagnosed with AD each year in the United States alone.

Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as Aβ. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders.

3-amino-1-propanesulfonic acid (3APS, Tramiprosate, Alzhemed™) is a promising investigational product candidate for the treatment of Alzheimer's disease that is currently in Phase III clinical trials in North America and Europe (Wright, T. M., Drugs of Today (2006), 42(5): 291-298). This product is developed by Neurochem Inc. (Laval, QC, Canada) and it is believed to act by reducing the deposition and/or load of amyloid in the brain through its binding to soluble Aβ peptide. For increasing the therapeutic effectiveness of 3APS, it would be desirable to increase bioavailability, stability and/or crossing the blood brain barrier of 3APS. These and other needs can be satisfied by the disclosure herein of a prodrug form of 3-amino-1-propanesulfonic acid (3APS), pharmaceutical compositions and uses thereof to treat various medical disorders.

Previous metabolic stability studies had demonstrated that there was no in vitro metabolism of 3APS. Those studies include: 3APS metabolic stability in pooled human hepatocytes, human, rat and dog liver microsomes, human intestinal microflora, pooled human liver cytosol, and human arylamine N-acetyltransferase (See Examples 4 and 5).

SUMMARY OF THE INVENTION

Surprisingly, it has now been found that 3APS is metabolized both in vitro and in vivo. Indeed, as described in more detail hereinafter, recent in vivo studies indicate extensive metabolism, particularly first-pass and/or systemic metabolism of 3APS. Three potential metabolites were identified from at least one type of biological species: 2-carboxyethanesulfonic acid, 3-hydroxy-1-propanesulfonic acid and 3-acetylamino-1-propanesulfonic acid. Further studies demonstrated that 2-carboxyethanesulfonic acid was the only major metabolite of 3APS in mice, rats, dogs and humans.

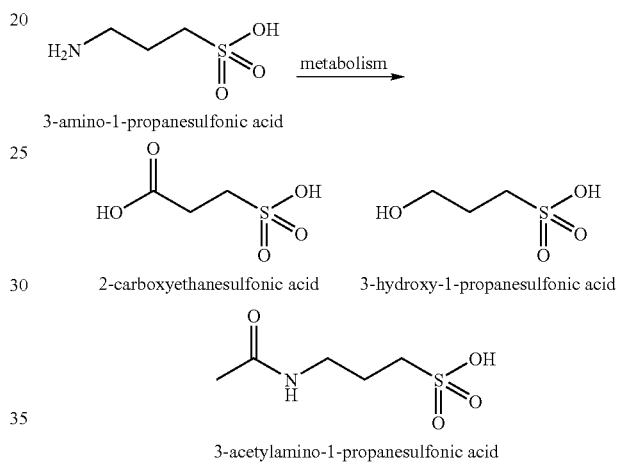

Without wishing to be bound by theory, it is hypothesized that metabolism of 3APS is mainly caused by a transaminase and/or monoamine oxidase that generates 2-carboxyethanesulfonic acid as the main metabolite and 3-hydroxy-1-propanesulfonic acid as a minor metabolite. N-acetyl-3-aminopropanesulfonic acid is another possible minor metabolite and it is believed to be produced by an enzyme that acetylates 3APS. These hypotheses are supported by in vitro experiments (see, for example, Example 5) showing that the conversion of 3APS to 2-carboxyethanesulfonic acid in primary neuron culture media was significantly inhibited by vigabatrin, a classic GABA transaminase inhibitor. Nialamide, a monoamine oxidase inhibitor, also reduced the formation of 2-carboxyethanesulfonic acid (from 3APS) but to a lesser extent.

Accordingly, an aspect of the invention concerns compounds and compositions that can deliver 3APS by minimizing the metabolism, e.g., first-pass metabolism, associated with that drug, and more particularly compounds that would block or protect the amino group of 3APS such that it avoids metabolism, e.g., by transaminases and/or monoamine oxidases.

The invention includes methods, compounds, compositions and vehicles for delivering in a subject, preferably a human subject, 3-amino-1-propanesulfonic acid, or salts thereof. 3-Amino-1-propanesulfonic acid (also named 3APS, Tramiprosate, Alzhemed™) has the structure:

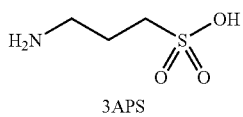

3APS

According to an aspect, the present invention relates to compounds or compositions that will yield or generate 3APS after administered in a subject. In one embodiment, the compound that will yield or generate 3APS is an amino acid prodrug of 3APS. In another embodiment, the compound that will yield or generate 3APS is a carbamate prodrug of 3APS. In another embodiment, the compound that will yield or generate 3APS is an amide prodrug of 3APS. In another embodiment, the compound that will yield or generate 3APS is a carbohydrate-derived prodrug of 3APS. In another embodiment, the compound that will yield or generate 3APS is a N-hydroxy prodrug. In another embodiment, the compound that will yield or generate 3APS is a cyclic double-protected prodrug. In further embodiment, the compound that yields or generates 3APS is a 3APS polymer (e.g. a molecule composed of two or more molecules of 3APS linked together). In further embodiment, the compound that yields or generates 3APS is a gemini dimer of 3APS. In certain embodiments, the amino acid prodrugs of 3APS that are capable of yielding or generating, either in vitro or in vivo, 3APS have one of the general or specific formulae or structures disclosed herein. The present invention encompasses these compounds, pharmaceutical compositions containing these compounds, and methods employing such compounds or compositions in the treatment of various medical disorders such as Alzheimer's disease.

The present invention also relates to pharmaceutical compositions comprising a compound of the present invention.

The present invention further relates to a method for increasing the therapeutic effectiveness of 3APS comprising administering to a subject, preferably a human subject, an effective amount of a prodrug of the present invention.

The present invention also provides processes for converting compounds of the invention to 3APS. The conversion and/or generation of 3APS involves contacting any of the compounds of the invention, e.g., with blood, plasma and/or brain cells. The conversion can occur in vitro or in vivo. The conversion may also occur in the presence of enzymes capable of cleaving amine bonds, such as peptidases, or other enzymes appropriate for other structures herein, including those found in the blood, plasma and/or brain.

The invention also provides the use of a compound according to the invention for the manufacture of a medicament. The invention also provides the use of a compound of the invention for the treatment or prevention of Alzheimer's disease, mild cognitive impairment, Down's syndrome, Hereditary Cerebral Hemorrhage with Amyloidosis of the Dutch-Type, cerebral amyloid angiopathy, other degenerative dementias, dementias of mixed vascular and degenerative origin, dementia associated with Parkinson's disease, dementia associated with progressive supranuclear palsy, dementia associated with cortical basal degeneration, or diffuse Lewy body type of Alzheimer's disease. The invention also provides methods for the treatment or prevention of the aforementioned diseases comprising administration of a therapeutically effective amount of a compound of the invention or a composition comprising the same, to a subject, preferably a human subject, in need thereof. More preferably, the disease is Alzheimer's disease. Accordingly, a related aspect of the invention relates to the prevention and/or treatment of Alzheimer's disease in a human subject by administering an effective amount of a compound or composition of the present invention to a human subject in need thereof.

In a further embodiment the invention includes administration of 3APS via or under the mucous membranes, the nose (intranasally), mouth, or eye, e.g., by nasal spray, chewing gum, or eye drops, via the ear, e.g., by eardrops, by the use of an implant, rectally, e.g., by a suppository or enema, vaginally, e.g., by a cream or lotion, or by the respiratory system, e.g., by inhalation, intranasally or intratracheally.

The invention in further aspects includes the administration of compounds of the invention via any mode and/or vehicle, including all modes and/or vehicles disclosed herein, e.g., the administration of the prodrugs of 3APS via the nose, mucous membranes, transdermally, via a patch, etc.

This invention in various aspects relates to the following numbered aspects:

Aspect 1. A compound of the Formula I:

$$B-L-A \qquad (I)$$

wherein

B is a pharmacokinetic modulating moiety, which is optionally also bonded to A directly or indirectly through a further linking group L;

A is a 3-amino-1-propanesulfonic acid moiety (i.e., 3APS bound to L-B), and

L is a cleavable linkage for covalently and dissociably coupling B to A (preferably and typically via the $NH_2$ group), or is absent, whereby L can be a direct bond or additional chemical structure providing a cleavable linkage, or a pharmaceutically acceptable salt or solvate thereof.

Aspect 2. The compound according to aspect 1, wherein

L is a linkage that when metabolized or hydrolyzed either in vitro or in vivo produces 3APS, and/or B is a moiety that increases the therapeutic bio-distribution of 3APS upon administration of the compound of formula I to a human subject.

Aspect 3. The compound according to aspect 1, wherein B is a 3-amino-1-propanesulfonic acid moiety.

Aspect 4. A compound according to aspect 1, wherein B is an amino acid or a peptide, and L is a hydrolyzable linkage.

Aspect 5. A compound according to aspect 1, which is a compound of formula (I), (I-A), (I-C), (I-D), (I-E), (I-P), (I-P2), (II), (III), (IV), (V), (VI), (VII), (VIII), (IX), (X), (XI), (XII), (XII-A) or (XIII), which are set forth hereinafter, or a pharmaceutically acceptable salt thereof.

Aspect 6. A pharmaceutical composition comprising a compound of aspect 1 and a pharmaceutically acceptable vehicle.

Aspect 7. A method for treating or preventing Alzheimer's disease, mild cognitive impairment Down's syndrome, Hereditary Cerebral Hemorrhage with Amyloidosis of the Dutch-Type, cerebral amyloid angiopathy, a degenerative dementia, a dementia of mixed vascular and degenerative origin, dementia associated with Parkinson's disease, dementia associated with progressive supranuclear palsy, dementia associated with cortical basal degeneration, or diffuse Lewy body type of Alzheimer's disease comprising administering a therapeutically effective amount of a compound of aspect 1 to a human subject in need thereof.

Aspect 8. A process for converting a compound of aspect 1 to 3APS comprising contacting said compound with an enzyme which metabolizes said compound to 3APS in vitro or in vivo.

Aspect 9. A process according to aspect 8, comprising contacting said compound with plasma, blood and/or brain cells.

Aspect 10. A method for increasing the therapeutic bio-distribution of 3APS in a human subject, comprising lessening metabolism of 3APS, e.g., first pass metabolism, which occurs when 3APS is administered to a human subject.

Aspect 11. A method for reducing side effects of 3APS in a human subject (e.g., reducing or preventing gastrointestinal intolerance), comprising lessening metabolism of 3APS, e.g., first pass metabolism, which occurs when 3APS is administered to a human subject.

Aspect 12. A method according to aspect 10, wherein 3APS is administered in the form of a prodrug of 3APS which yields or generates 3APS after being administered to said human subject.

Aspect 13. A method according to aspect 10, wherein the prodrug is a compound of the Formula I:

$$B\text{-}L\text{-}A \quad (I)$$

wherein
B is a pharmacokinetic modulating moiety, which is optionally also bonded to A directly or indirectly through a further linking group L;
A is a 3-amino-1-propanesulfonic acid moiety (i.e., 3APS bound to L-B), and
L is a cleavable linkage for covalently and dissociably coupling B to A (preferably and typically via the $NH_2$ group), or is absent, whereby L can be a direct bond or additional chemical structure providing a cleavable linkage,
or a pharmaceutically acceptable salt or solvate thereof.

Aspect 14. A method according to aspect 10, wherein 3APS is administered through the respiratory system, intratracheally, intranasally, via or under a mucous membrane, via the ear, rectally, or vaginally, or by an implant, spray, nasal spray, chewing gum, eye drop, eardrop, suppository, enema, or vaginal cream or lotion.

Aspect 15. The method of aspect 10, wherein the bioavailability of 3APS, AUC of 3APS, brain levels of 3APS, CSF levels of 3APS, $C_{max}$ of 3APS, $T_{max}$ of 3APS, and/or bio-absorption of 3APS is increased.

Aspect 16. A method according to aspect 10, wherein Alzheimer's disease is treated or prevented.

Aspect 17. A method according to aspect 10, wherein the effective therapeutic level of 3APS in a selected human tissue is increased.

Aspect 18. A method according to aspect 17, which increases the level of 3APS in the brain of said human subject.

Aspect 19. A method according to aspect 10, which increases the therapeutic effectiveness of 3APS.

Aspect 20. A method according to aspect 10, which lessens the first pass metabolism of 3APS.

Aspect 21. A method according to aspect 10, which reduces the side effects of 3APS.

Aspect 22. A method according to aspect 10, wherein the oral AUC of 3APS is increased by at least 20%.

Aspect 23. A method for increasing the therapeutic bio-distribution of 3APS in a human subject, comprising administering 3APS in the form of a prodrug or in the form of a gemini dimer of 3APS.

Aspect 24. A method for increasing the therapeutic bio-distribution of 3APS in a human subject, comprising administering 3APS non-orally or non-enterally.

Aspect 25. A method according to aspect 10, wherein 3APS is delivered using a route (transdermally, S.C., intranasally, etc.) or vehicle (patch, implant, spray, formulation, etc.) which minimizes hepatic first-pass metabolism of 3APS.

Aspect 26. A compound according to aspect 1, wherein said cleavable linkage is selected for yielding or generating 3APS or a derivative of 3APS, either in vitro or in vivo, e.g., wherein the linkage is cleavable hydrolytically or enzymatically.

Aspect 27. A compound according to aspect 1, wherein said pharmacokinetic modulating moiety is selected for increasing the therapeutic bio-distribution of 3APS upon administration of the compound of formula I to a human subject.

Aspect 28. A prodrug of the Formula I:

$$B\text{-}L\text{-}A \quad (I)$$

wherein
B is a pharmacokinetic modulating moiety, which is optionally also bonded to A directly or indirectly through a further linking group L;
A is a 3-amino-1-propanesulfonic acid moiety (i.e., 3APS bound to L-B), and
L is a cleavable linkage for covalently and dissociably coupling B to A (preferably and typically via the $NH_2$ group), or is absent, whereby L can be a direct bond or additional chemical structure providing a cleavable linkage,
or a pharmaceutically acceptable salt, metabolite or solvate thereof,
wherein the metabolite of said prodrug can be 3APS and/or other metabolites, including, but not limited to, metabolites identified elsewhere herein, e.g., the examples.

Additional objects, advantages and features of the present invention will become more apparent upon reading of the following non-restrictive description of preferred embodiments which are exemplary and should not be interpreted as limiting the scope of the invention.

I. Definitions

All technical and scientific terms used herein have the same meaning as commonly understood by one ordinary skilled in the art to which the invention pertains. For convenience, the meaning of certain terms and phrases used herein are provided below.

To the extent the definitions of terms in the publications, patents, and patent applications incorporated herein by reference are contrary to the definitions set forth in this specification, the definitions in this specification control. The section headings used herein are for organizational purposes only, and are not to be construed as limiting the subject matter disclosed.

It should be noted that, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

The symbol "—" in general represents a bond between two atoms in the chain. Thus $CH_3$—O—$CH_2$—$CH(R_i)$—$CH_3$ represents a 2-substituted-1-methoxypropane compound. In addition, the symbol "—" represents the point of attachment of the substituent to a compound. Thus for example aryl($C_1$-$C_6$)-alkyl indicates an arylalkyl group, such as benzyl, attached to the compound at the alkyl moiety.

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

As used herein, the term "Compounds of the present invention" and equivalent expressions refers to compounds mentioned herein as being useful for at least one purpose of the invention, e.g., those encompassed by structural Formulae such as (I), (I-A), (I-C), (I-D), (I-E), (I-P), (I-P2), (II), (III), (IV), (V), (VI), (VII), (VIII), (IX), (X), (XI), (XII), (XII-A) and (XIII), and includes specific compounds mentioned herein such as A1 to A35, C1 to C26, B1 to B14, H1 to H4, G1 to G11, S1 to S14 and D1 to D8, etc., as well as their pharmaceutically acceptable salts and solvates. Embodiments herein may exclude one or more of the compounds of the invention. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers, or diastereomers. Accordingly, the chemical structures disclosed herein encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan, e.g., chiral chromatography (such as chiral HPLC), immunoassay techniques, or the use of covalently (such as Mosher's esters) and non-covalently (such as chiral salts) bound chiral reagents to respectively form a diastereomeric mixture which can be separated by conventional methods, such as chromatography, distillation, crystallization or sublimation, the chiral salt or ester is then exchanged or cleaved by conventional means, to recover the desired isomers. The compounds may also exist in several tautomeric forms including the enol form, the keto form, and mixtures thereof. Accordingly, the chemical structures depicted herein encompass all possible tautomeric forms of the illustrated compounds. The disclosed compounds also include isotopically labeled compounds where one or more atoms have an atomic mass different from the atomic mass most abundantly found in nature. Examples of isotopes that may be incorporated into the compounds of the present invention include, but are not limited to, $^2H(D)$, $^3H(T)$, $^{11}C$, $^{13}C$, $^{14}C$, $^{15}N$, $^{18}O$, $^{17}O$, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present invention. Further, when partial structures of the compounds are illustrated, brackets or equivalents indicate the point of attachment of the partial structure to the rest of the molecule.

The term "prodrug" and equivalent expressions refer to agents which can be converted in vitro or in vivo directly or indirectly to an active form (see, e.g., R. B. Silverman, 1992, "The Organic Chemistry of Drug Design and Drug Action," Academic Press, Chap. 8; Bundgaard, Hans; Editor. Neth. (1985), "Design of Prodrugs". 360 pp. Elsevier, Amsterdam; Stella, V.; Borchardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the biodistribution (e.g., to allow agents which would not typically enter the reactive site of the protease) or the pharmacokinetics for a particular agent. A wide variety of groups have been used to modify compounds to form prodrugs, for example, esters, ethers, phosphates, etc. When the prodrug is administered to a subject, the group is cleaved, enzymatically or non-enzymatically, reductively, oxidatively, or hydrolytically, or otherwise to reveal the active form. As used herein, "prodrug" includes pharmaceutically acceptable salts thereof, or pharmaceutically acceptable solvates as well as crystalline forms of any of the foregoing. Prodrugs are frequently, although not necessarily, pharmacologically inactive until converted to the parent drug.

The term "gemini dimer" and equivalent expressions refer to a synthetic compound comprising at least two moieties of the same agent or drug coupled together. For background on gemini dimers, see: Hammell D C, Hamad M, Vaddi H K, Crooks P A, Stinchcomb A L. A duplex "Gemini" prodrug of naltrexone for transdermal delivery. J Control Release. 2004. 97(2):283-90. In preferred embodiment, the gemini dimers of the invention are made of two linked 3APS molecules that may be converted in vitro or in vivo directly or indirectly to release at least one, preferably two, pharmaceutically active 3APS molecules.

The term "carbamate" refers to an oxycarbonyl residue (—OC(O)—) linked to an amino group to form a group comprising a (—OC(O)N(or NH)—) radical The carbamate group can be secondary (NH) or tertiary (N). This term is further defined in Section II-B(a).

The term "amide" refers to an organic compound containing a carbonyl (—C(O)—) attached to an amine group to form a group comprising the radical (—C(O)N (or NH)—). The amide group can be secondary (NH) or tertiary (N). This term is further defined in Section II-A. The term "non-amino acid amide" refers to an amide group where the carbonyl (—C(O)—) does not form part of an amino acid residue. This term is further defined in Section II-B(b).

The term "carbohydrate-derived" refers to compounds where the group attached to, for example, 3APS, is an organic group that is or is derived from a polyhydroxy aldehyde, polyhydroxy ketone, or a polyol, can change to such group on simple chemical transformations, such as hydrolysis, oxidation, or reduction. These groups include, for example, sugars, starches, celluloses, and gums. This term is further defined in Section II-C. The term "N-hydroxy-derived" refers to compounds containing a hydroxy or hydroxy-derived group (e.g. alkoxy, benzyloxy, phenoxy, acyloxy, and the like) to form an (RO—N(or NH)—). This term is further defined in Section II-D(a).

The term "cyclic double-protected" refers to compounds wherein a protecting group in linked to both the amine and the sulfonic acid of 3APS. This term is further defined in Section II-D(b).

The term "ester" refers to compounds that can be represented by the formula RCOOR (carboxylic ester) or the formula $RSO_3R'$ (sulfonate ester)', where the group R can be, for example 3APS or the 3-aminopropane part thereof, and the group R' can be another organic group. These compounds are usually respectively formed by the reaction between a carboxylic or a sulfonic acid and an alcohol usually with the elimination of water.

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated or N-alkylated amino acids, as well as amino acids having nitrogen or oxygen-containing side chains (such as Lys, Orn, or Ser) in which the nitrogen or oxygen atom has been acylated or alkylated. Amino acids may be pure L or D isomers or mixtures of L and D isomers, including racemic mixtures. In general, amino acids are represented by the residue of Formula V.

The term "natural amino acid" and equivalent expressions refer to L-amino acids commonly found in naturally occurring proteins. Examples of natural amino acids include, without limitation, alanine (Ala), cystein (Cys), aspartic acid (Asp), glutamic acid (Glu), phenylalanine (Phe), glycine (Gly), histidine (H is), isoleucine (Ile), lysine (Lys), leucine (Leu), methionine (Met), asparagine (Asp), proline (Pro), glutamine (Gln), arginine (Arg), serine (Ser), threonine (Thr), valine (Val), tryptophan (Trp), tyrosine (Tyr), β-alanine (β-ALA), and γ-aminobutyric acid (GABA).

The term "unnatural amino acid" refers to any derivative of a natural amino acid including D forms, and α- and β-amino acid derivatives. The terms "unnatural amino acid" and "non-natural amino acid" are used interchangeably herein and are meant to include the same moieties. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-NH$_2$-Phe), 2-aminopimelic acid (Apm), biphenylalanine (Bip), para-bromophenylalanine (4-Br-Phe), ortho-chlorophenylalanine (2-C$_1$-Phe), meta-chlorophenylalanine (3-Cl-Phe), para-chlorophenylalanine (4-C$_1$-Phe), meta-chlorotyrosine (3-C$_1$-Tyr), para-benzoylphenylalanine (Bpa), tert-butylglycine (TLG), cyclohexylalanine (Cha), cyclohexylglycine (Chg), desmosine (Des), 2,2-diaminopimelic acid (Dpm), 2,3-diaminopropionic acid (Dpr), 2,4-diaminobutyric acid (Dbu), 3,4-dichlorophenylalanine (3,4-C$_{1-2}$-Phe), 3,4-difluororphenylalanine (3,4-F$_2$-Phe), 3,5-diiodotyrosine (3,5-I$_2$-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), hydroxylysine (Hyl), allo-hydroxylysine (aHyl), 5-hydroxytryptophan (5-OH-Trp), 3- or 4-hydroxyproline (3- or 4-Hyp), para-iodophenylalanine (4-I-Phe), 3-iodotyrosine (3-I-Tyr), indoline-2-carboxylic acid (Idc), isodesmosine (Ide), allo-isoleucine (a-Ile), isonipecotic acid (Inp), N-methylisoleucine (MeIle), N-methyllysine (MeLys), meta-methyltyrosine (3-Me-Tyr), N-methylvaline (MeVal), 1-naphthylalanine (1-Nal), 2-naphthylalanine (2-Nal), para-nitrophenylalanine (4-NO$_2$-Phe), 3-nitrotyrosine (3-NO$_2$-Tyr), norleucine (Nle), norvaline (Nva), ornithine (Orn), ortho-phosphotyrosine (H$_2$PO$_3$-Tyr), octahydroindole-2-carboxylic acid (Oic), penicillamine (Pen), pentafluorophenylalanine (F$_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

As used herein, the term "acyclic" refers to an organic moiety without ring system.

The term "aliphatic group" includes organic moieties characterized by straight or branched-chains, typically having between 1 and 15 carbon atoms. Aliphatic groups include non cyclic alkyl groups, alkenyl groups, and alkynyl groups.

As used herein, the term "alkyl" refers to saturated hydrocarbons having from one to twelve carbon atoms, including linear, branched, and cyclic alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, cyclopropyl, cyclopentyl, cyclohexyl, cycloheptyl, cyclooctyl, and the like. The term alkyl includes both unsubstituted alkyl groups and substituted alkyl groups. The term "$C_1$-$C_n$alkyl", wherein n is an integer from 2 to 12, refers to an alkyl group having from 1 to the indicated "n" number of carbon atoms.

As used herein, the term "alkenyl" refers to unsaturated hydrocarbons having from two to twelve carbon atoms, including linear, branched, and cyclic non aromatic alkenyl groups, and comprising between one to six carbon-carbon double bond. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, cyclopentenyl, cyclohexenyl, ethylcyclopentenyl, ethylcylohexenyl, and the like. The term alkenyl includes both unsubstituted alkenyl groups and substituted alkenyl groups. The term "$C_2$-$C_n$alkenyl", wherein n is an integer from 3 to 12, refers to an alkenyl group having from 2 to the indicated "n" number of carbon atoms.

As used herein, the term "alkynyl" refers to unsaturated hydrocarbons having from two to twelve carbon atoms, including linear, branched, and cyclic non aromatic alkynyl groups, and comprising between one to six carbon-carbon triple bond. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The term "$C_2$-$C_n$alkynyl", wherein n is an integer from 3 to 12, refers to an alkynyl group having from 2 to the indicated "n" number of carbon atoms.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal or less than 6 carbon atoms.

The terms "cycloalkyl", "alicyclic", "carbocyclic" and equivalent expressions refer to a group comprising a saturated or partially unsaturated carbocyclic ring in a single, spiro (sharing one atom), or fused (sharing at least one bond) carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo [4,3,0]nonanyl, norbornyl, and the like. The term cycloalkyl includes both unsubstituted cycloalkyl groups and substituted cycloalkyl groups. The term "$C_3$-$C_n$cycloalkyl", wherein n is an integer from 4 to 15, refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

The term "heterocycloalkyl" and equivalent expressions refer to a group comprising a saturated or partially unsaturated carbocyclic ring in a single, spiro (sharing one atom), or fused (sharing at least one bond) carbocyclic ring system having from three to fifteen ring members, including one to six heteroatoms (e.g. N, O, S, P) or groups containing such heteroatoms (e.g. NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g. via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl", wherein n is an integer from 4 to 15, refers to a heterocycloalkyl group having from 3 to the indicated "n" number of atoms in the ring structure, including at least one hetero group or atom as defined above. Unless the number of carbons is otherwise specified, "lower heterocycloalkyl" groups as herein used, have at least 3 and equal or less than 8 carbon atoms in their ring structure.

The terms "aryl" and "aryl ring" refer to aromatic groups having "$4n+2$"$\pi$(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl", wherein n is an integer from 6 to 15, refers to an aryl group having from 6 to the indicated "n" number of atoms in the ring structure, including at least one hetero group or atom as defined above.

The terms "heteroaryl" and "heteroaryl ring" refer to an aromatic groups having "$4n+2$"$\pi$(pi) electrons, wherein n is an integer from 1 to 3, in a conjugated monocyclic or polycyclic system (fused or not) and having five to fourteen ring members, including one to six heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g. via a nitrogen atom), where such is possible. Examples of heteroaryl groups include, without limitation, pyridyl, imidazolyl, pyrimidinyl, pyrazolyl, triazolyl, tetrazolyl, furyl, thienyl, isooxazolyl, thiazolyl, oxazolyl, isothiazolyl, pyrrollyl, quinolinyl, isoquinolinyl, indolyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl", wherein n is an integer from 6 to 15, refers to an heteroaryl group having from 5 to the indicated "n" number of atoms in the ring structure, including at least one hetero group or atom as defined above.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —$NR^aR^b$, in which $R^a$ and $R^b$ are each independently hydrogen, alkyl, aryl, or heterocyclyl, or $R^a$ and $R^b$, taken together with the nitrogen atom to which they are attached, form a heterocyclic ring. The term amino includes compounds or moieties in which a nitrogen atom is covalently bonded to at least one carbon or heteroatom. Thus, the terms "alkylamino" and "dialkylamino" as used herein means an amine group having respectively one and at least two $C_1$-$C_6$alkyl groups attached thereto. The term "arylamino" and "diarylamino" include groups wherein the nitrogen is bound to at least one or two aryl groups, respectively. The term "amide" or "aminocarbonyl" includes compounds or moieties which contain a nitrogen atom which is bound to the carbon of a carbonyl or a thiocarbonyl group. The term acylamino refers to an amino group directly attached to an acyl group as defined herein.

The term "nitro" means —NO$_2$; the terms "halo" and "halogen" refer to bromine, chlorine, fluorine or iodine substituents; the term "thiol", "thio", or "mercapto" means SH; and the term "hydroxyl" or "hydroxy" means —OH. The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The term "alkoxy" or "lower alkoxy" as used herein means an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups and the like. The term alkoxy includes both unsubstituted or substituted alkoxy groups, etc., as well as perhalogenated alkyloxy groups.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group ($C_1$-$C_6$alkyl, $C_1$-$C_6$alkenyl, $C_1$-$C_6$alkynyl, e.g. acetyl), a cycloalkyl group ($C_3$-$C_8$cycloalkyl), a heterocyclic group ($C_3$-$C_8$heterocycloalkyl and $C_5$-$C_6$heteroaryl), an aromatic group ($C_6$aryl, e.g., benzoyl), and the like. Acyl groups may be unsubstituted or substituted acyl groups (e.g. salicyloyl).

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. The term "substituted", when in association with any of the foregoing groups refers to a group substituted at one or more position with substituents such as acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g. if the group contains an alkyl group, an aryl group, or other.

The term "solvate" refers to a physical association of a compound of this invention with one or more solvent molecules, whether organic or inorganic. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, hemiethanolates, and the like.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that takes advantage of an intrinsically basic, acidic or charged functionality on the molecule and that is not biologically or otherwise undesirable. Example of pharmaceutically acceptable salts are also described, for example, in Berge et al., "Pharmaceutical Salts", *J. Pharm. Sci.* 66, 1-19 (1977). Such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g. lithium, sodium, potassium), an alkaline earth ion (e.g. magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from the parent agent that contains a basic or acidic moiety, by conventional chemical methods. Generally, such salts are prepared by reacting the free acid or base forms of these agents with a stoichiometric amount of the appropriate base or acid in water or in an organic solvent, or in a mixture of the two. Salts may be prepared in situ, during the final isolation or purification of the agent or by separately reacting a purified compound of the invention in its free acid or base form with the desired corresponding base or acid, and isolating the salt thus formed. The term "pharmaceutically acceptable salts" also include zwitterionic compounds containing a cationic group covalently bonded to an anionic group, as they are "internal salts".

All acid, salt, base, and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

"Abeta", "Aβ", or "β-amyloid", is defined as any peptide resulting from beta-secretase mediated cleavage of Beta Amyloid Precursor Protein (APP), including for examples peptides of 37, 38, 39, 40, 41, 42, and 43 amino acids, and extending from the beta-secretase cleavage site to amino acids 37, 38, 39, 40, 41, 42, or 43. It also includes It also includes N-terminal truncated species of above peptides, such as the pyroglutamic forms pE3-40, pE3-42, pE3-43, pE11-42, pE11-43 and the like. For convenience of nomenclature, "$A\beta_{1-42}$", may be referred to herein as "Aβ(1-42)" or simply as "$A\beta_{42}$" (and likewise for any other amyloid peptides discussed herein). As used herein, the terms "Abeta", "Aβ", "β-amyloid", "amyloid-β" are synonymous referring collectively to truncated and non-truncated peptide species of the sequence between β- and γ-cleavage sites of APP.

The term "amyloid-β disease" or "amyloid-β related disease" may be used for mild cognitive impairment; vascular dementia; early Alzheimer's disease; Alzheimer's disease, including sporadic (non-hereditary) Alzheimer's disease and familial (hereditary) Alzheimer's disease; age-related cognitive decline; cerebral amyloid angiopathy ("CAA"); hereditary cerebral hemorrhage; senile dementia; Down's syndrome; inclusion body myositis ("IBM"); or age-related macular degeneration ("ARMD"), Mild cognitive impairment ("MCI"), Cerebral amyloid angiopathy ("CAA"), age-related macular degeneration (ARMD).

"AUC" is the area under a curve representing the concentration of a compound in a biological sample of a subject as a function of time following administration of the compound to the subject. Examples of biological samples include biological fluids such as plasma and blood, or organ homogenates such as brain or liver homogenates. The AUC can be determined by measuring the concentration of a compound in a biological sample such as the plasma, blood or brain homogenate using methods such as liquid chromatography-tandem mass spectrometry (LC/MS/MS), at various time intervals, and calculating the area under the concentration-versus-time curve. Suitable methods for calculating the AUC from a drug concentration-versus-time curve are well known in the art. As relevant to the disclosure here, an AUC for 3APS can be determined by measuring the concentration of 3APS in the plasma, blood or brain homogenate of a subject following oral administration of a compound of Formulae (I), (I-A), (I-C), (I-D), (I-E), (I-P), (I-P2), (II), (III), (IV), (V), (VI), (VII), (VIII), (IX), (X), (XI), (XII) or (XII-A), to the subject. Unless noted otherwise herein; AUC means $AUC_{0-\infty}$, as further defined in Example 4.

"Bioavailability" refers to the rate and amount of a drug that reaches the systemic circulation of a subject following administration of the drug or prodrug thereof to the patient and can be determined by evaluating, for example, the plasma or blood concentration-versus-time profile for the drug. Parameters useful in characterizing a plasma or blood concentration-versus-time curve include the area under the curve (AUC), the time to peak concentration ($T_{max}$), and the maximum drug concentration ($C_{max}$). Bioavailability is often expressed as F(%) referring to the ratio in percentage of the AUC of the compound for a specific mode of administration (e.g. orally) over AUC of the compound after an IV administration.

"Bioequivalence" refers to equivalence of the rate and extent of absorption of a drug after administration of equal doses of the drug or prodrug to a patient. As used herein, two plasma or blood concentration profiles are bioequivalent if the 90% confidence interval for the ratio of the mean response of the two profiles is within the limits of 0.8 and 1.25. The mean response includes at least one of the characteristic parameters of a profile such as $C_{max}$, $T_{max}$, and AUC.

"$C_{max}$" is the maximum concentration of a drug in the biological sample of a subject following administration of a dose of the drug or prodrug to the subject.

"$T_{max}$" is the time to the maximum concentration ($C_{max}$) of a drug in the biological sample of a subject following administration of a dose of the drug or prodrug to the subject.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the size, age, and general health of the subject; the specific disease involved; the degree of or involvement or the severity of the disease; the response of the individual subject; the particular compound administered; the mode of administration; the bioavailability characteristics of the preparation administered; the dose regimen selected; the use of concomitant medication; and other relevant circumstances.

As used herein the term "therapeutic bio-distribution of 3APS" refers to one or more pharmacokinetic parameters of 3APS which affect 3APS therapeutic activity. Examples of such pharmacokinetic (PK) parameters include but are not limited to: bioavailability of 3APS, AUC of 3APS, brain levels of 3APS, CSF levels of 3APS, $C_{max}$ of 3APS, $T_{max}$ of 3APS, and/or bio-absorption of 3APS, etc.

As used herein the terms "increased (or like terms, e.g., increasing, increase in, etc.) therapeutic effectiveness of 3APS" and "enhanced (or like terms, e.g., enhancing, enhancement, etc.) therapeutic effectiveness of 3APS" refer to an increased effectiveness of 3APS as measured, e.g., by one or more parameters listed under "therapeutic bio-distribution of 3APS" above, e.g., by 5%, 10%, 20%, 30%, 40%, 50%, 60%, 70%, 80%, 90%, 95%, 99%, 125%, etc., or even more, e.g., 2, or 4 fold, or even more when administered to a subject, e.g., animal or human, which increase is with respect to the same equivalent molar dose of 3APS administered orally in water solution. Preferably such % increases are achieved also with respect to 3APS administered orally in the formulation of Table 3 of U.S. Ser. No. 11/103,656, filed on Apr. 12, 2005. Effectiveness can also be as measured, for example, by effect on characteristics of a disease such as Alzheimer's disease, e.g., by the reduction of plaques or AD load in the brain, or by an improvement in selected manifestations of the disease, e.g., memory loss, cognition, reasoning, judgment, orientation, etc. See U.S. Ser. No. 11/103,656, filed on Apr. 12, 2005, for details on how to measure effects on characteristics of such diseases.

The term "lessening metabolism of 3APS" (or related terms such as reduction, less, lowering, reducing, lowered, etc) refers to decreasing the degree or amount of first-pass metabolism in the GI tract or liver of 3APS (by administering it to a subject non-orally or in particular oral formulations or in the form of a prodrug) by e.g., 5%, 10%, 20%, 30%, 40%, 50%, 60%, 70%, 80%, 90%, 95%, 99%, or even 100%, which decrease is with respect to the degree or amount of metabolism of 3APS that occurs when the same equivalent molar dose of 3APS is administered orally in water solution. Preferably such % decreases are achieved also with respect to 3APS administered orally in the formulation of Table 3 of U.S. Ser. No. 11/103,656, filed on Apr. 12, 2005.

The term "reduction of side effects of 3APS" refers to decreasing the amount of or severity of one or more side effects of 3APS by, e.g., 5%, 10%, 20%, 30%, 40%, 50%, 60%, 70%, 80%, 90%, 95%, 99%, or 99.9%, or even 100%, which decrease is with respect to the amount of or severity of a side effect of 3APS that is exhibited when the same equivalent molar dose of 3APS is administered orally in water solution. Preferably such % decreases are achieved also with respect to 3APS administered orally in the formulations of Table 3 of U.S. Ser. No. 11/103,656, filed on Apr. 12, 2005.

More generally, the terms lessening etc., increasing etc., refer in context herein to the percentage changes, e.g., by 5%, 10%, 20%, 30%, 40%, 50%, 60%, 70%, 80%, 90%, 95%, 99%, 125%, etc., or even more, e.g., 2, or 4 fold, or even more.

All of the pharmacokinetic data in U.S. Ser. No. 11/103,656, filed on Apr. 12, 2005, are incorporated herein by reference, including the data for example 1 and of Table 3, for example, for forming a comparative basis for the effects achieved by the present inventions.

When referring to "3APS" being produced (e.g., released from a formulation or prodrug), all forms of 3APS are included, e.g., solvates thereof, ionically dissociated forms thereof, charged forms thereof, etc.

"Pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans.

"Pharmaceutically acceptable vehicle" refers to a diluent, adjuvant, excipient, or carrier with which a compound is administered.

"Pharmaceutical composition" refers to at least one compound and at least one pharmaceutically acceptable vehicle, with which the compound is administered to a patient.

"Preventing" or "prevention" is intended to refer at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease).

"Treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of the disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination, a psychiatric evaluation, or a cognition test such as CDR, MMSE, DAD, ADAS-Cog, or another test known in the art. For example, the methods of the invention successfully treat a subject's dementia by slowing the rate of or lessening the extent of cognitive decline.

"Therapeutically effective amount" means the amount of compound that, when administered to a patient for treating or preventing a disease, is sufficient to effect such treatment or prevention of the disease. The "therapeutically effective amount" will vary depending on the compound, the disease and its severity, and the age, weight, etc., of the patient having the disease to be treated or prevented.

Reference will now be made in detail to certain embodiments of compounds and methods. The disclosed embodiments are not intended to be limiting of the invention.

In a further aspect the invention includes the administration of 3APS that is not via a transdermal patch, or not by topical administration in a composition, e.g., lotions, creams, solutions, gels or solids or not by subcutaneous, intravenous or intraperitoneal injection, or not intraspinally, or intracerebrally.

II. Compounds of the Invention

The present invention relates to methods, compounds and compositions for delivering in a subject, preferably a human subject, 3-amino-1-propanesulfonic acid, or salts thereof, also referred herein as 3APS. The invention encompasses compounds that will yield or generate 3APS, either in vitro or in vivo.

In a preferred embodiment, compounds of the invention include prodrugs that will yield or generate 3APS once administered in a human. Without wishing to be bound by theory, in some aspects the prodrugs according to invention comprise a "pharmacokinetic modulating moiety," e.g., B, below, covalently but dissociably linked to 3APS that, e.g., by a linkage, L, below, which will be cleaved once in the blood, plasma or other specific tissue (e.g. brain), thereby releasing 3APS.

Thus, in one aspect, the invention relates to a compound of the Formula I:

B-L-A           (I)

as well as pharmaceutically acceptable salts, metabolites, and solvates thereof, where:

B is a pharmacokinetic modulating moiety, which is optionally also bonded to A directly or indirectly thought a further linking group L;

A is 3-amino-1-propanesulfonic acid moiety (i.e., 3APS bound to L-B); and

L is a cleavable linkage for covalently and dissociably coupling B to A (preferably and typically via the $NH_2$ group), or is absent, whereby L can be a direct bond or additional chemical structure providing a cleavable linkage.

Suitable pharmacokinetic modulating moieties (e.g. B) moieties include amino acid or peptide moieties, carbamate moieties, non-amino-acid amide moieties, carbohydrate-derived moieties and analogs such as inositol-derived moieties, N-hydroxy and derivatives thereof (e.g., where the H in OH is replaced by an OH protecting group). B can also comprise a cyclic double protected 3APS molecule and precursors (e.g., where a moiety connects $NH_2$ and $SO_3H$ of 3APS, e.g., sulfinic acids, thiols, sulfides, disulfides, etc.), and combinations thereof. More generally B moieties include N-protecting groups. B can also be the molecule 3APS itself (see gemini dimers).

Suitable linkages L will be any which are cleaved as described herein, e.g., by enzymes mentioned herein or others in blood, plasma and or brain cells, in vitro or in vivo. Linkages will generally comprise a bond which is known to be so cleavable such as but not limited to, a peptide, amide, ester, sulfide, disulfide, carboxamate, urea, —N—O—, etc. bond, and others as demonstrated for example in the structures disclosed herein, all of which are in general applicable as linkages, L, in compounds in general. Actual cleavability of the linker can be assessed in vitro and/or in vivo by using hydrolytic-, enzymatic (e.g. peptidase, esterase) or metabolic-based tests and assays well known in the art. International PCT application WO 91/14434, published applications US 2005/0096317, US 2006/0046967 and provisional application U.S. 60/____ filed concurrently herewith, are all incorporated herein by reference since they describe a variety of linkers that may be useful according to the present invention.

In another aspect, the invention relates to Formula I-A (and salts, esters and solvates thereof)

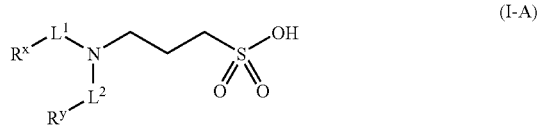

(I-A)

wherein, $R^x$ and $R^y$ are independently selected from hydrogen and a protecting group, wherein $R^x$ and $R^y$ are not both hydrogen; and $L^1$ and $L^2$ are each a cleavable linkage; wherein when $R^x$ is H, $L^1$ is absent, and when $R^y$ is H, then $L^2$ is absent.

The term "protecting group" refers to a group inhibiting and reducing metabolism of the amino group of 3APS. Examples of protecting groups include, without limitation, an amino acid residue, a carbamate, a non-amino acid amide, a carbohydrate-derived residue, a N-hydroxy-derived residue, a cyclic double protecting group, and the like.

According to preferred embodiments, the compounds of the invention exhibit numerous advantageous properties. In one embodiment, the compound is a prodrug which bypasses first-pass metabolism by the liver and/or the digestive tract (e.g. gut, stomach, or intestine) that is associated with administration of 3APS, per se, thereby increasing bio-distribution and/or bioavailability of 3APS as compared to an administration of a molar equivalent of 3APS. Bypassing hepatic first-pass metabolism modifies, improves or increases pharmacokinetic parameters of 3APS such as the AUC, the $C_{max}$ and/or $T_{max}$ of 3APS. In one embodiment, the compound is a prodrug which exhibits an increased absorption by the gastrointestinal tract, compared to the administration a molar equivalent of 3APS per se. In one embodiment, the compound is a prodrug which provides a slow release of 3APS over time. In another embodiment, the compound is a prodrug which increases brain levels of 3APS when compared to the administration a molar equivalent of 3APS per se. In another embodiment, the compound is a prodrug which lessens common side effects associated with the administration of 3APS per se. For instance, in a preferred embodiment, the prodrug exhibits a better gastrointestinal tolerability than 3APS.

In preferred embodiments the compounds and/or compositions of the invention achieve one or more of the following benefits: (1) reducing the molar dose of 3APS administered to a patient (e.g. due to a improved absorption when compared to 3APS or due to a reduction in the first-pass metabolism of 3APS); (2) avoiding common side effects such as gastrointestinal irritation associated with an oral administration of 3APS; (3) improving penetration of 3APS across the BBB; (4) reducing the side effects associated with 3APS (e.g. by lessening gastrointestinal problems or by increasing the relative amount of 3APS reaching the brain; (5) increasing concentration or levels of 3APS in desired tissues or fluids (e.g. brain, CSF). Other benefits will be apparent to those skilled in the art.

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein. Compounds of the invention are also shown in Table 1, Table 2, Table 3, Table 4 and Table 4B below.

The compounds of the present invention may exhibit polymorphism. Polymorphs of compounds according to this invention may be prepared by crystallization under different conditions. For example, using different solvents or different solvent mixtures for recrystallization; crystallization at different temperatures; various modes of cooling ranging from very fast to very slow cooling during crystallization. Polymorphs may also be obtained by heating or melting a prodrug followed by gradual or fast cooling. The presence of polymorphs may be determined by solid probe NMR spectroscopy, IR spectroscopy, differential scanning calorimetry, powder X-ray diffraction or other such techniques.

The compounds of the present invention may also exist in the form of a solvate, for example, hydrate, ethanolate, n-proponalate, iso-propanolate, 1-butanolate, 2-butanolate and solvates of other physiologically acceptable solvents, such as the Class 3 solvents described in the *International Conference on Harmonization (ICH), Guidance for Industry, Q3C Impurities: Residual Solvents* (1997). The present invention includes each solvate and mixtures thereof.

The amino acid or peptidic moiety, the carbamate moiety, the non-amino acid amide moiety, the carbohydrate-derived moiety and analogs such as inositol-derived, the N-hydroxy moiety and derivatives, or any other pharmacokinetic modulating moiety of the prodrugs, including cyclic double protected 3APS and precursors (e.g. sulfinic acids, thiol, sulfide, disulfide, etc), and combinations thereof, according to the invention may be cleaved prior to absorption by the gastrointestinal tract (e.g., within the stomach or intestinal lumen) and/or after absorption by the gastrointestinal tract (e.g., in intestinal tissue, blood, liver, or other suitable tissue of a mammal). In certain embodiments, 3APS remains covalently attached to the pharmacokinetic modulating moiety during transit across the intestinal mucosal barrier to provide protection from presystemic metabolism. In certain embodiments, pharmacokinetic modulating moieties according to the invention are essentially not metabolized to the corresponding 3APS within cells of the intestine or liver (e.g. enterocytes, hepatocytes), but generates the parent 3APS molecule once within the systemic circulation. In certain embodiments, at least some of the prodrug administered generates the corresponding 3APS only once in the brain, i.e. after it has passed the blood brain barrier (BBB). Cleavage of the pharmacokinetic modulating moiety of prodrugs according to the invention after absorption by the gastrointestinal tract may allow these prodrugs to be absorbed into the systemic circulation either by active transport, passive diffusion, or by a combination of both active and passive processes. Accordingly, in certain embodiments, a pharmaceutical composition, formulation, or dosage form of the present invention is capable of maintaining a therapeutically effective concentration of 3APS in the plasma or blood of a patient for a time period of at least about 1 hour, for at least 2 hours, for at least 3 hours, 4 hours, for at least about 8 hours, for a period of at least about 12 hours, at least about 16 hours, at least about 20 hours, and in certain embodiments for at least about 24 hours after the pharmaceutical composition, formulation, or dosage form comprising a corresponding compound according to the invention and a pharmaceutically acceptable vehicle is orally administered to the patient. In certain embodiments, a pharmaceutical composition, formulation, or dosage form of the present invention is capable of improving the $T_{max}$ of 3APS by at least 2 fold, or by at least 3, 4, 5, 6, 7, 8, 9 or 10 fold or more.

The pharmacokinetic modulating moiety of certain of the compounds according to the invention may be cleaved either chemically and/or enzymatically. One or more enzymes present in the stomach, intestinal lumen, intestinal tissue, blood, liver, brain, or any other suitable tissue of a mammal may enzymatically cleave the amino acid or peptidic moiety of the compound. If the pharmacokinetic modulating moiety is cleaved after absorption by the gastrointestinal tract, certain of the compounds according to the invention may have the opportunity to be absorbed into the systemic circulation from the large intestine. In certain embodiments, the pharmacokinetic modulating moiety is cleaved after absorption by the gastrointestinal tract or after crossing the BBB.

Although theory of operation is discussed herein, for specific compound structures, including all generic structural formulas and specific names and formulas of compounds, the invention is not limited by any such theories unless specifically stated otherwise. Thus, all uses of all novel compounds are encompassed by the invention, irrespective of mechanism or theory of operation.

II-A. Amino Acid Prodrugs

In a preferred embodiment, the compounds of the invention are amino acids prodrugs that will yield or generate 3APS once administered in a human. Preferred prodrugs are composed of an amino acid residue linked to the amine group of 3APS via an amide bond. The amino acid residue may be cleaved in vivo by enzymes such as peptidases, or by any other mechanisms, to liberate the amine group of 3APS.

More particularly, an aspect of the invention relates to a compound of Formula (II), and to pharmaceutically acceptable salts, esters or solvates thereof:

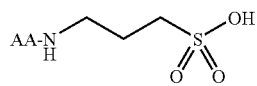

(II)

wherein AA is a natural or unnatural amino acid residue or a peptide comprising 2, 3 or more natural or unnatural amino acid residues.

Other aspects of the invention relate to compounds of Formula (III) and to a pharmaceutically acceptable salt or solvate thereof:

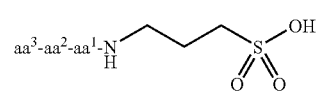

(III)

wherein:
aa$^1$ is a natural or unnatural amino acid residue;
aa$^2$ and aa$^3$ are each independently a natural or unnatural amino acid residue or absent.

Further aspects of the invention relate to compounds of Formula (IV) and to pharmaceutically acceptable salts, esters or solvates thereof:

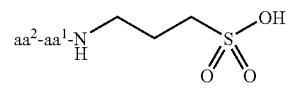

(IV)

wherein:
aa$^1$ is a natural or unnatural amino acid residue;
aa$^2$ is a natural or unnatural amino acid residue, or is absent.

Yet further aspects of the invention relate to compounds of Formula (V), and to pharmaceutically acceptable salts, esters or solvates thereof:

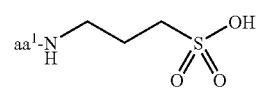

(V)

wherein aa$^1$ is a natural or unnatural amino acid residue.

The invention further relates to compounds of Formula (V-A), and to pharmaceutically acceptable salts, esters or solvates thereof:

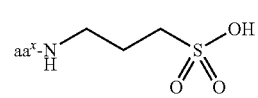

(V-A)

wherein aa$^x$ is an amino acid residue selected from valine, proline, lysine, leucine, methionine, D-methionine, serine, alanine, D-alanine, glycine, isoleucine, histidine, aminoisobutyric acid, phenylglycine, tryptophan, tyrosine, O-benzylserine, O-benzylglutamine, and γ-aminobutyric acid.

In preferred embodiments aa$^x$ is an amino acid residue selected from valine, lysine, methionine, serine, and O-benzylserine, or a pharmaceutically acceptable salt or solvate thereof.

In one embodiment, the amino acid residue is coupled via an acid end (C-coupled). In an embodiment, the amino acid residue is a natural amino acid residue, or a salt or ester thereof. In another embodiment, the amino acid residue is an unnatural amino acid residue, or a salt or ester thereof. In yet another embodiment, the amino acid residue is not a phenylalanine, e.g., in the case where a single amino acid is attached to the N atom, but also in any other case. In a further embodiment, natural or unnatural amino acid residues in Formula II, Formula II, Formula IV, Formula V, or Formula V-A are optionally represented by Formula (VI):

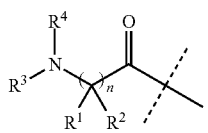

(VI)

wherein:

$R_1$ and $R_2$ are each independently selected from the group consisting of H and a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, $C_5$-$C_{15}$heteroaryl, NH($C_1$-$C_6$alkyl), N($C_1$-$C_6$alkyl)$_2$, and C(O)($C_1$-$C_6$alkyl); or $R_1$ and $R_2$ are taken together with the adjacent carbon atom to form a substituted or unsubstituted $C_3$-$C_{12}$heterocycloalkyl;

$R_3$ is selected from the group consisting of H and a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, $C_5$-$C_{15}$heteroaryl, C(O)($C_1$-$C_6$alkyl), and C(O)($C_6$-$C_{10}$aryl); or $R_3$ is a bond between two amino acid residues, when at least two amino acid residues are present;

$R_4$ is selected from the group consisting of H and a substituted or unsubstituted group selected from $C_1$-$C_6$alkyl, $C_2$-$C_6$alkenyl, $C_2$-$C_6$alkynyl; or $R_1$ and $R_4$ are taken together with the adjacent carbon and nitrogen atoms to form a $C_3$-$C_{10}$heterocycloalkyl; and n is 1, 2 or 3, or a higher number.

In one embodiment, the compound of the invention comprises an amino acid residue of Formula VI, wherein $R_2$ is H and all other groups are as previously disclosed. In another embodiment, the compound of the invention comprises an amino acid residue of Formula VI, wherein $R_2$ and $R_3$ are each H and all other groups are as previously disclosed. In another embodiment, the compound of the invention comprises an amino acid residue of Formula VI, wherein when $R_2$ and $R_3$ are each H, then $R_1$ is not an aryl-substituted $C_1$alkyl. In another embodiment, the compound of the invention comprises an amino acid residue of Formula VI, wherein when $R_2$ and $R_3$ are each H, then $R_1$ is not a —$CH_2$ aryl group. In another embodiment, the compound of the invention comprises an amino acid residue of Formula VI, wherein when $R_2$ is H and $R_3$ is H or a bond, then $R_1$ is not a —$CH_2$-phenyl group. In another embodiment, the invention provides compounds of Formula V, provided that aa$^1$ is not a phenylalanine. In another embodiment, the invention provides compounds of Formula IV, provided that aa$^1$ and aa$^2$ are not both D-phenylalanine. In another embodiment, the invention provides compounds of Formula IV, provided that aa$^1$ and aa$^2$ are not both L-phenylalanine. In another embodiment, the invention provides compounds of Formula IV, provided that when one of aa$^1$ and aa$^2$ is D-phenylalanine, then the other is not D-phenylalanine or D-tyrosine. In yet another embodiment, the invention provides compounds of Formula IV, provided that when one of aa$^1$ and aa$^2$ is L-phenylalanine, then the other is not D-phenylalanine or L or D-tyrosine.

TABLE 1

Exemplary amino acid prodrugs according to the invention

| ID | Structure |
|---|---|
| A1 | 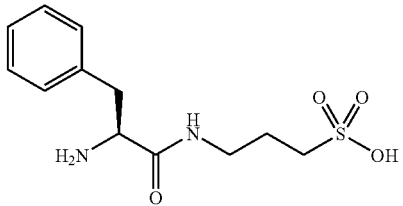 [SMILES: N[C@@H](Cc1ccccc1)C(=O)NCCCS(=O)(=O)O] |
| A2 | 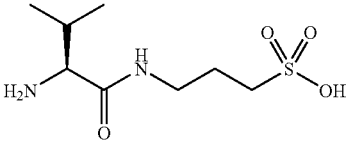 |
| A3 | 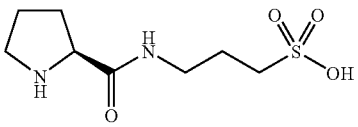 [SMILES: O=C(NCCCS(=O)(=O)O)[C@@H]1CCCN1] |
| A4 | 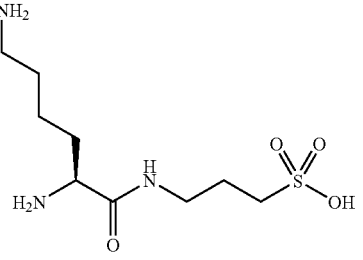 |
| A5 | 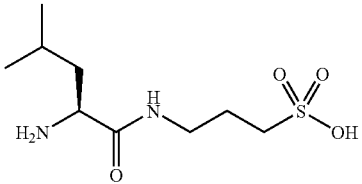 [SMILES: CC(C)C[C@H](N)C(=O)NCCCS(=O)(=O)O] |
| A6 | 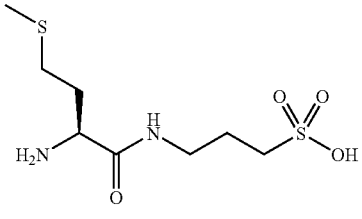 [SMILES: CSCC[C@H](N)C(=O)NCCCS(=O)(=O)O] |
| A7 | 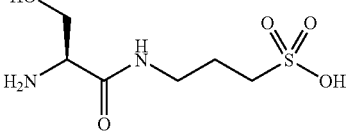 |
| A8 | 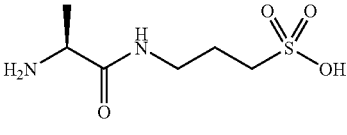 |

TABLE 1-continued

Exemplary amino acid prodrugs according to the invention

| ID | Structure |
|----|-----------|
| A9 | Ala-NH-CH$_2$CH$_2$CH$_2$-SO$_3$H |
| A10 | Gly-NH-CH$_2$CH$_2$CH$_2$-SO$_3$H |
| A11 | Ile-NH-CH$_2$CH$_2$CH$_2$-SO$_3$H |
| A12 | Met-NH-CH$_2$CH$_2$CH$_2$-SO$_3$H |
| A13 | His-NH-CH$_2$CH$_2$CH$_2$-SO$_3$H |
| A14 | Aib-NH-CH$_2$CH$_2$CH$_2$-SO$_3$H |
| A15 | Phg-NH-CH$_2$CH$_2$CH$_2$-SO$_3$H |
| A16 | Trp-NH-CH$_2$CH$_2$CH$_2$-SO$_3$H |
| A17 | Tyr-NH-CH$_2$CH$_2$CH$_2$-SO$_3$H |
| A18 | Ser(OBn)-NH-CH$_2$CH$_2$CH$_2$-SO$_3$H |
| A19 | Glu(OBn)-NH-CH$_2$CH$_2$CH$_2$-SO$_3$H |
| A20 | H$_2$N-CH$_2$CH$_2$CH$_2$-C(O)-NH-CH$_2$CH$_2$CH$_2$-SO$_3$H |
| A21 | Glu-NH-CH$_2$CH$_2$CH$_2$-SO$_3$H |
| A22 | Asp-NH-CH$_2$CH$_2$CH$_2$-SO$_3$H |
| A23 | Ser-Val-HN-CH$_2$CH$_2$CH$_2$-SO$_3$H |

TABLE 1-continued

Exemplary amino acid prodrugs according to the invention

| ID | Structure |
|---|---|
| A24 | Ala-Leu-HN~~~S(O)(O)OH |
| A25 | Ser-Lys-Leu-HN~~~S(O)(O)OH |
| A26 | Lys-Leu-HN~~~S(O)(O)OH |
| A27 | Gly-Pro-Glu-HN~~~S(O)(O)OH |
| A28 | Val-Val-HN~~~S(O)(O)OH |
| A29 | Met-Val-HN~~~S(O)(O)OH |
| A30 | Met-Ala-HN~~~S(O)(O)OH |
| A31 | Ala-Ala-HN~~~S(O)(O)OH |
| A32 | Gly-Gly-HN~~~S(O)(O)OH |
| A33 | Met-Gly-HN~~~S(O)(O)OH |
| A34 | Met-Met-HN~~~S(O)(O)OH |
| A35 | O-Bn-Ser-Val-HN~~~S(O)(O)OH |

Preferred amino acid prodrugs according to the invention are Compounds A2, A4, A6, A7 and A18 (as described above), and pharmaceutically acceptable salts and solvates thereof.

II-B. Carbamate, Non-Amino Acid Amide and Related Prodrugs

Certain aspects of the invention relate to a compound of Formula (VII), and to pharmaceutically acceptable salts, esters or solvates thereof:

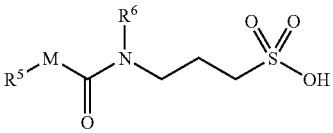

(VII)

wherein, $R_5$ is a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, $C_5$-$C_{15}$heteroaryl, NH($C_1$-$C_6$alkyl), N($C_1$-$C_6$alkyl)$_2$, and C(O)($C_1$-$C_6$alkyl);

$R_6$ is a hydrogen or a substituted or unsubstituted group selected from C(O)NH$_2$, C(O)NH($C_1$-$C_6$alkyl), C(O)N($C_1$-$C_6$alkyl)$_2$, and C(O)($C_1$-$C_6$alkyl); or $R_5$ and $R_6$ are taken together with the adjacent carbon atom to form a substituted or unsubstituted $C_3$-$C_{12}$heterocycloalkyl;

M is selected from the group consisting of oxygen, sulfur, and nitrogen (NH or N($C_1$-$C_6$alkyl)) or is absent.

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein.

In one embodiment, the invention provides compounds of Formula VII, wherein when M is absent and $R^8$ is H, then $R^5$ is other than 1-(4-isobutylphenyl)ethyl. In another embodiment, the invention provides compounds of Formula VII, wherein when $R^6$ is H and M is NH or absent, then $R^5$ is other than 1-(4-isobutylphenyl)ethyl. In another embodiment, the invention provides compounds of Formula VII, wherein when $R^6$ is H and M is NH, then $R^5$ is other than benzyl, diphenylmethyl, hexyl, dodecyl, adamantyl, and t-butyl. In another embodiment, the invention provides compounds of Formula VII, wherein when $R^6$ is H and M is NH, then $R^5$ is other than hydrogen, 1,4-dihydro-5,6-dimethyl-4-oxo-2-pyrimidinyl, and 5-ethyloxycarbonyl-1-penthyl. In another embodiment, the invention provides compounds of Formula VII, wherein when M is NH and $R^5$ and $R^6$ are taken together with the adjacent carbon atom to form a substituted or unsubstituted $C_{3-12}$heterocycloalkyl, then the heterocycloalkyl is other than benzimidazol-2-one, tetrahydro-2,4,6-trioxo-1,3,5-triazine, 2,4-dioxo-1-imidazolidine, 2,4-dioxo-(di or tetrahydro)-benzo[g]pteridine, 4,10-dihydro-10-methyl-2,4-dioxopyrimido[4,5b]quinoline, 2-oxo-1-imidazolidinyl, and 3,4-dihydro-2,4-dioxo-1-(2H)pyrimidine. In another embodiment, the invention provides compounds of Formula VII, wherein when M is NH, then $R^5$ and $R^6$ are not taken together with the adjacent carbon atom to form a substituted or unsubstituted $C_{3-12}$heterocycloalkyl. In another embodiment, the invention provides compounds of Formula VII, wherein when $R^6$ is H and M is O, then $R^5$ is other than t-butyl and benzyl. In another embodiment, the invention provides compounds of Formula VII, wherein when $R^6$ is H and M is O, then $R^5$ is other than i-butyl and 9H-fluoren-9-ylmethyl. In another embodiment, the invention provides compounds of Formula VII, wherein when $R^5$ is H and M is absent, then $R^5$ is other than benzyl, phenyl, 3-pyridinyl, 3-N-methylpyridinium, methyl, trifluoromethyl, pentafluoroethyl, pentafluorophenyl, and t-butyl. In another embodiment, the invention provides compounds of Formula VII, wherein when $R^6$ is H and M is absent, then $R^5$ is other than n-butyl, i-butyl, n-propyl, i-propyl, vinyl, 2-propenyl, 2-(1-decenyl), 2-(1-dodecenyl), 1-(8-undecenyl), octyl, decyl, undecyl, tridecyl, pentadecyl, heptadecyl, 4-(N-oxy-2,2,6,6-tetramethylpiperidinyl), 5-(1,3-dihydro-1,3-dioxo-2-benzofuranyl), 4-nitrophenyl, and 3-phenoxyphenyl.

a) Carbamate Prodrugs

In some preferred embodiments, the compounds of the invention are carbamate prodrugs that will yield or generate 3APS once administered in a human. Preferred prodrugs comprise an oxycarbonyl residue (—OC(O)—) linked to the amine group of 3APS via a carbamate bond (—OC(O)—NH—). The amine residue may be cleaved in vivo by enzymes or by any other mechanisms, including hydrolysis, to liberate the amine group of 3APS. In a preferred embodiment, the compounds of the invention are carbamate prodrugs that will yield or generate 3APS once administered in a human.

More particularly, certain aspects of the invention relate to a compound of Formula (VIII), and to pharmaceutically acceptable salts, esters or solvates thereof:

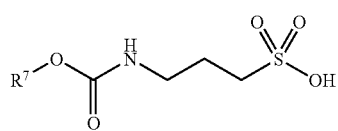

(VIII)

wherein, $R^7$ is a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, $C_5$-$C_{15}$heteroaryl, $C_7$-$C_{12}$arylalkyl, $C_7$-$C_{12}$heteroarylalkyl, and combinations thereof.

In one embodiment, the definition of $R^7$ is a substituted or unsubstituted 1-(alkylcarboxy)alkyl group. In another embodiment, $R^7$ is a substituted or unsubstituted benzyl group. In another embodiment, $R^7$ is a substituted or unsubstituted heterocycloalkylmethylene group. In another embodiment, the invention provides compounds of Formula VIII, provided that $R^7$ is other than t-butyl or benzyl. In another embodiment, the invention provides compounds of Formula VIII, provided that $R^7$ is other than i-butyl or 9H-fluoren-9-ylmethyl.

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein. Compounds of the invention are also shown in Table 2 below.

TABLE 2

Exemplary carbamate prodrugs according to the invention

| ID | Structure |
|---|---|
| C1 | 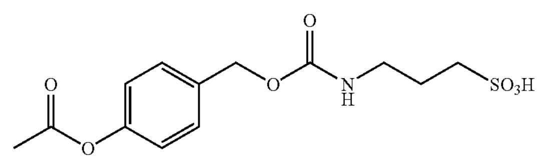 [SMILES: CC(=O)Oc1ccc(COC(=O)NCCCS(=O)(=O)O)cc1] |
| C2 | 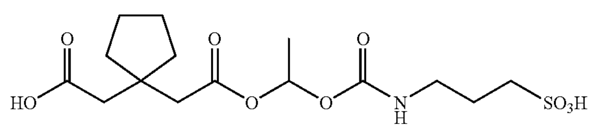 [SMILES: CC(OC(=O)CC1(CC(=O)O)CCCC1)OC(=O)NCCCS(=O)(=O)O] |
| C3 | 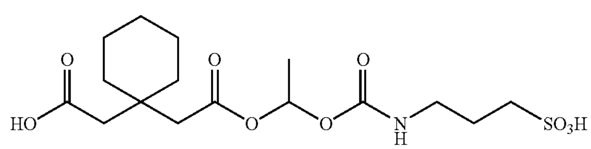 [SMILES: CC(OC(=O)CC1(CC(=O)O)CCCCC1)OC(=O)NCCCS(=O)(=O)O] |
| C4 | 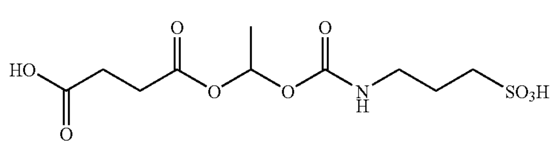 [SMILES: CC(OC(=O)CCC(=O)O)OC(=O)NCCCS(=O)(=O)O] |
| C5 | 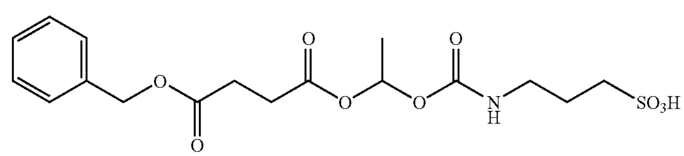 [SMILES: CC(OC(=O)CCC(=O)OCc1ccccc1)OC(=O)NCCCS(=O)(=O)O] |

TABLE 2-continued

Exemplary carbamate prodrugs according to the invention

| ID | Structure |
|----|-----------|
| C6 | 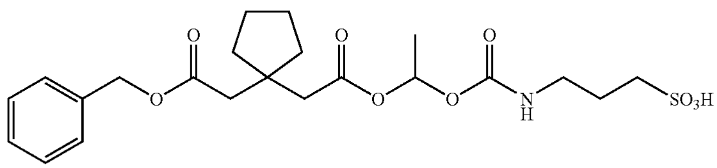 [SMILES: CC(OC(=O)CC1(CC(=O)OCc2ccccc2)CCCC1)OC(=O)NCCCS(=O)(=O)O] |
| C7 | 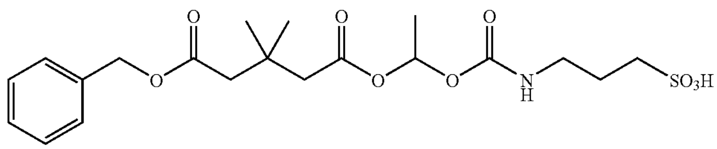 [SMILES: CC(OC(=O)CC(C)(C)CC(=O)OCc1ccccc1)OC(=O)NCCCS(=O)(=O)O] |
| C8 | 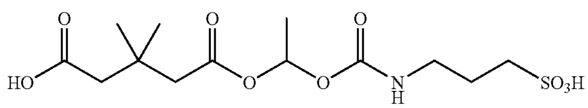 [SMILES: CC(OC(=O)CC(C)(C)CC(=O)O)OC(=O)NCCCS(=O)(=O)O] |
| C9 | 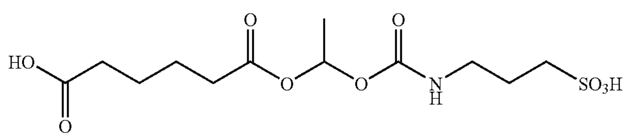 [SMILES: CC(OC(=O)CCCCC(=O)O)OC(=O)NCCCS(=O)(=O)O] |
| C10 | 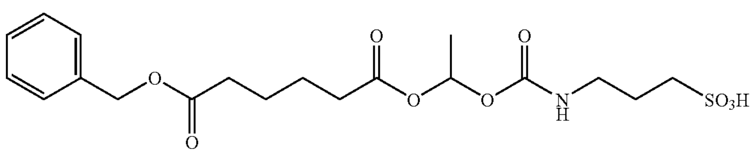 [SMILES: CC(OC(=O)CCCCC(=O)OCc1ccccc1)OC(=O)NCCCS(=O)(=O)O] |
| C11 | 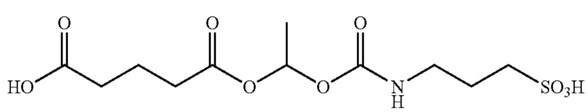 [SMILES: CC(OC(=O)CCCC(=O)O)OC(=O)NCCCS(=O)(=O)O] |
| C12 | 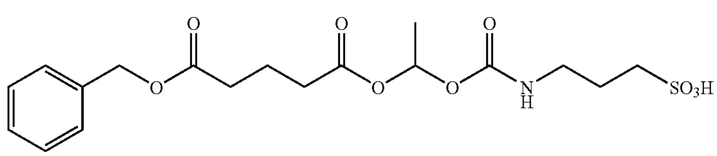 [SMILES: CC(OC(=O)CCCC(=O)OCc1ccccc1)OC(=O)NCCCS(=O)(=O)O] |
| C13 | 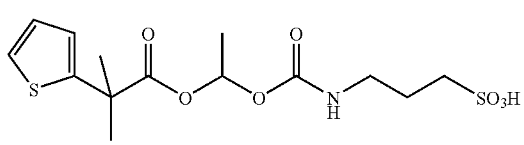 [SMILES: CC(OC(=O)NCCCS(=O)(=O)O)OC(=O)C(C)(C)c1cccs1] |
| C14 | 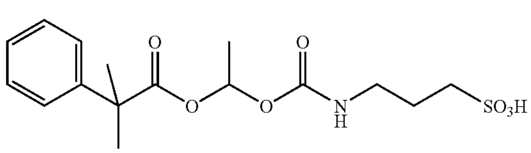 [SMILES: CC(OC(=O)NCCCS(=O)(=O)O)OC(=O)C(C)(C)c1ccccc1] |
| C15 | 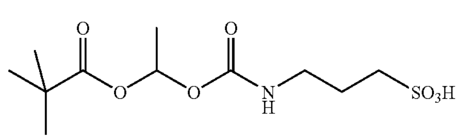 [SMILES: CC(OC(=O)NCCCS(=O)(=O)O)OC(=O)C(C)(C)C] |

TABLE 2-continued
Exemplary carbamate prodrugs according to the invention
| ID | Structure |
|---|---|
| C16 | 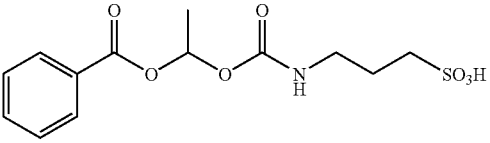 [SMILES: CC(OC(=O)NCCCS(=O)(=O)O)OC(=O)c1ccccc1] |
| C17 | 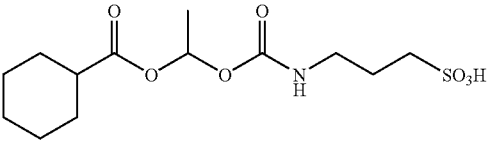 [SMILES: CC(OC(=O)NCCCS(=O)(=O)O)OC(=O)C1CCCCC1] |
| C18 | 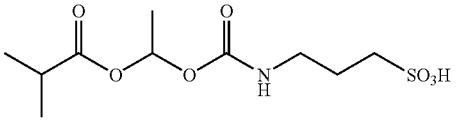 [SMILES: CC(OC(=O)NCCCS(=O)(=O)O)OC(=O)C(C)C] |
| C19 | 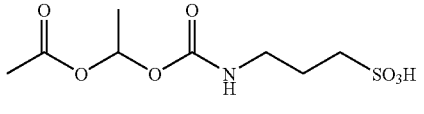 [SMILES: CC(=O)OC(C)OC(=O)NCCCS(=O)(=O)O] |
| C20 | 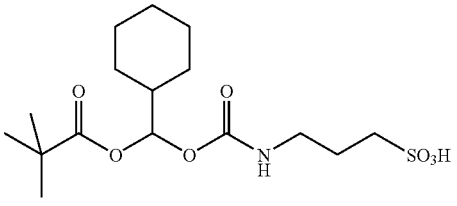 [SMILES: CC(C)(C)C(=O)OC(OC(=O)NCCCS(=O)(=O)O)C1CCCCC1] |
| C21 | 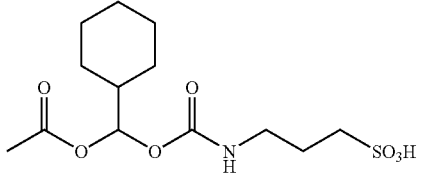 [SMILES: CC(=O)OC(OC(=O)NCCCS(=O)(=O)O)C1CCCCC1] |
| C22 | 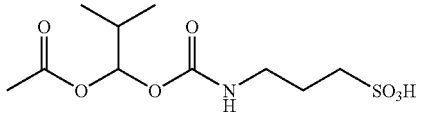 [SMILES: CC(=O)OC(OC(=O)NCCCS(=O)(=O)O)C(C)C] |
| C23 | 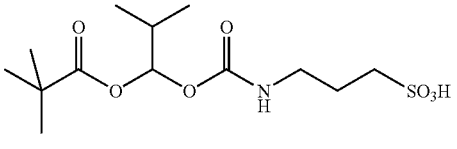 [SMILES: CC(C)C(OC(=O)NCCCS(=O)(=O)O)OC(=O)C(C)(C)C] |
| C24 | 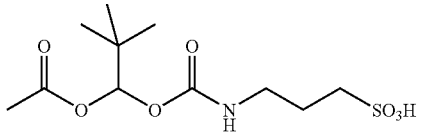 [SMILES: CC(=O)OC(OC(=O)NCCCS(=O)(=O)O)C(C)(C)C] |
| C25 | 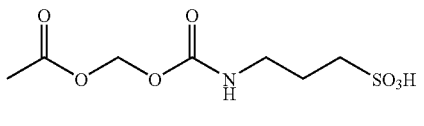 [SMILES: CC(=O)OCOC(=O)NCCCS(=O)(=O)O] |

TABLE 2-continued

Exemplary carbamate prodrugs according to the invention

| ID | Structure |
|---|---|
| C26 | 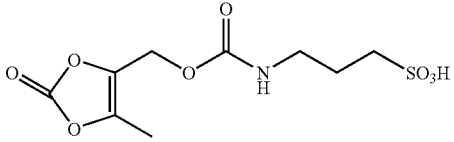 [SMILES: Cc1oc(=O)oc1COC(=O)NCCCS(=O)(=O)O] | b) Non-Amino Acid Amide Prodrugs

In some preferred embodiments, the compounds of the invention are non-amino acid amide prodrugs that will yield or generate 3APS once administered to a human. Preferred prodrugs comprise a carbonyl-containing residue linked to the amine group of 3APS via an amide bond. The carbonyl-containing residue may be cleaved in vivo by enzymes or by any other mechanism, to liberate the amine group of 3APS.

Preferred prodrugs are composed of a carbonyl-containing residue linked to the amine group of 3APS via an amide bond and such carbonyl-containing group having a nucleophile such as a carboxylic acid or alcohol, capable of internally cleaving the amide bond. The amino acid residue may be cleaved in vivo by enzymes, or by any other mechanism, to liberate the amine group of 3APS.

More particularly, certain aspects of the invention relate to a compound of Formula (IX), and to pharmaceutically acceptable salts, esters or solvates thereof:

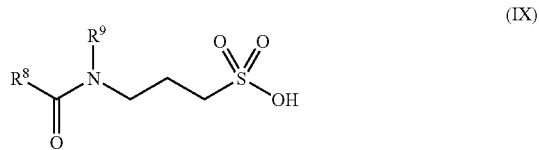

(IX)

wherein, $R^8$ is a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, $C_5$-$C_{15}$heteroaryl; and $R^9$ is a hydrogen or a substituted or unsubstituted C(O)($C_1$-$C_6$alkyl), C(O)$NH_2$, C(O)NH($C_1$-$C_6$alkyl), or C(O)N($C_1$-$C_6$alkyl)$_2$; or $R^8$ and $R^9$ are taken together with the adjacent carbon atom to form a substituted or unsubstituted $C_3$-$C_{12}$heterocycloalkyl.

In one embodiment, $R^8$ is a substituted $C_1$-$C_{12}$alkyl. In another embodiment, $R^8$ is a $C_1$-$C_{12}$alkyl substituted with a substituent selected from hydroxycarbonyl, alkoxycarbonyl, alkylcarbonyloxy, substituted or unsubstituted 2-hydroxyphenyl, substituted or unsubstituted 2-alkylcarbonyloxyphenyl group or combinations thereof. In another embodiment, $R^8$ is a substituted or unsubstituted benzyl group. In a further embodiment, $R^8$ is selected from the groups depicted in Table 3.

In one embodiment, the compound of the invention is a compound of Formula IX, wherein $R^9$ is H. In another embodiment, the compound of the invention is a compound of Formula IX, wherein $R^8$ and $R^9$ are taken together with the adjacent carbon atom to form a substituted or unsubstituted $C_3$-$C_{12}$heterocycloalkyl. In another embodiment, the compound of the invention is a compound of Formula IX, wherein $R^8$ and $R^9$ are taken together with the adjacent carbon atom to form a substituted or unsubstituted phthalimide. In another embodiment, the compound of the invention is a compound of Formula IX, wherein $R^8$ and $R^9$ are taken together with the adjacent carbon atom to form a substituted or unsubstituted $C_3$-$C_{12}$heterocycloalkyl, wherein said heterocycle is other than phthalimide. In another embodiment, the invention provides compounds of Formula IX, wherein when $R^9$ is H, then $R^8$ is other than benzyl, phenyl, 3-pyridinyl, 3-N-methylpyridinium, methyl, trifluoromethyl, pentafluoroethyl, pentafluorophenyl, and t-butyl. In another embodiment, the invention provides compounds of Formula IX, wherein when $R^9$ is H, then $R^8$ is other than n-butyl, i-butyl, n-propyl, i-propyl, vinyl, 2-propenyl, 2-(1-decenyl), 2-(1-dodecenyl), 1-(8-undecenyl), octyl, decyl, undecyl, tridecyl, pentadecyl, heptadecyl, 4-(N-oxy-2,2,6,6-tetramethylpiperidinyl), 5-(1,3-dihydro-1,3-dioxo-2-benzofuranyl), 4-nitrophenyl, and 3-phenoxyphenyl. In another embodiment, the invention provides compounds of Formula IX, wherein $R^8$ is selected from n-butyl, i-butyl, n-propyl, i-propyl, vinyl, 2-propenyl, 2-(1-decenyl), 2-(1-dodecenyl), 1-(8-undecenyl), octyl, decyl, undecyl, tridecyl, pentadecyl, heptadecyl, 4-(N-oxy-2,2,6,6-tetramethylpiperidinyl), 5-(1,3-dihydro-1,3-dioxo-2-benzofuranyl), 4-nitrophenyl, and 3-phenoxyphenyl. In yet another embodiment, the invention provides a compound of Formula IX, wherein when $R^9$ is H, then $R^8C(O)$ is other than a 24-oxocholan-24-yl. In yet another embodiment, the invention provides a compound of Formula IX, wherein when $R^9$ is H, then $R^8C(O)$ is other than (3α,5β)-3-hydroxy-24-oxocholan-24-yl, (3α,5β,12α)-3,12-dihydroxy-24-oxocholan-24-yl, (3α,5β,7α)-3,7-dihydroxy-24-oxocholan-24-yl, or (3α,5β,7α,12α)-3,7,12-trihydroxy-24-oxocholan-24-yl. In yet another embodiment, the invention provides a compound of Formula IX, wherein $R^8C(O)$ is selected from (3α,5β)-3-hydroxy-24-oxocholan-24-yl, (3α,5β,12α)-3,12-dihydroxy-24-oxocholan-24-yl, (3α,5β,7α)-3,7-dihydroxy-24-oxocholan-24-yl, and (3α,5β,7α,12α)-3,7,12-trihydroxy-24-oxocholan-24-yl.

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein. Compounds of the invention are also shown in Table 3 below.

TABLE 3

Exemplary non-amino acid amide prodrugs according to the invention

| ID | Structure |
|---|---|
| B1 | (cyclohexane-1,1-diyl)bis(acetic acid) mono-(3-sulfopropyl)amide |
| B2 | (cyclopentane-1,1-diyl)bis(acetic acid) mono-(3-sulfopropyl)amide |
| B3 | 3,3-dimethylglutaric acid mono-(3-sulfopropyl)amide |
| B4 | 2,2-dimethylglutaric acid mono-(3-sulfopropyl)amide |
| B5 | succinic acid mono-(3-sulfopropyl)amide |
| B6 | glutaric acid mono-(3-sulfopropyl)amide |
| B7 | 2,4-dimethylphenyl valine ester sulfonamide derivative |
| B8 | 4-amino-2-(3-sulfopropyl)isoquinoline-1,3(2H,4H)-dione |
| B9 | 2,4-dimethylphenyl phenylalanine ester sulfonamide derivative |

TABLE 3-continued

Exemplary non-amino acid amide prodrugs according to the invention

| ID | Structure |
|---|---|
| B10 | 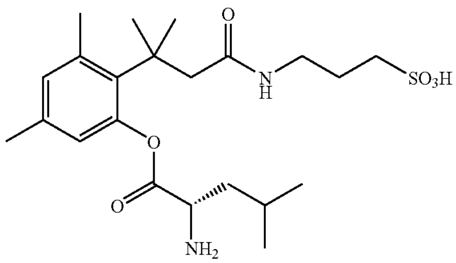 [SMILES: Cc1cc(C)c(C(C)(C)CC(=O)NCCCS(=O)(=O)O)c(OC(=O)[C@@H](N)CC(C)C)c1] |
| B11 | 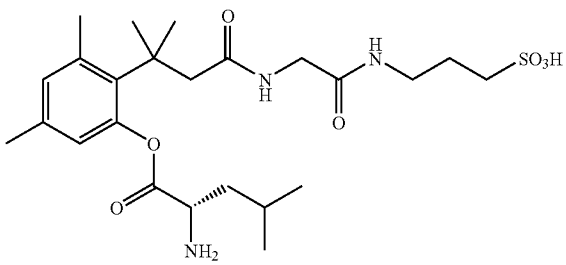 [SMILES: Cc1cc(C)c(C(C)(C)CC(=O)NCC(=O)NCCCS(=O)(=O)O)c(OC(=O)[C@@H](N)CC(C)C)c1] |
| B12 | 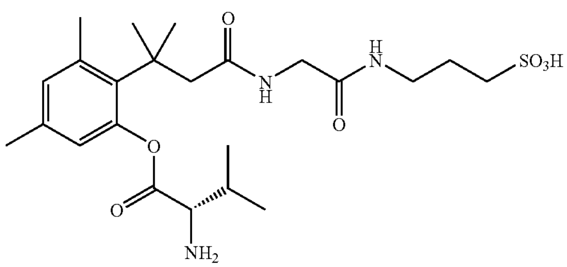 [SMILES: Cc1cc(C)c(C(C)(C)CC(=O)NCC(=O)NCCCS(=O)(=O)O)c(OC(=O)[C@@H](N)C(C)C)c1] |
| B13 | 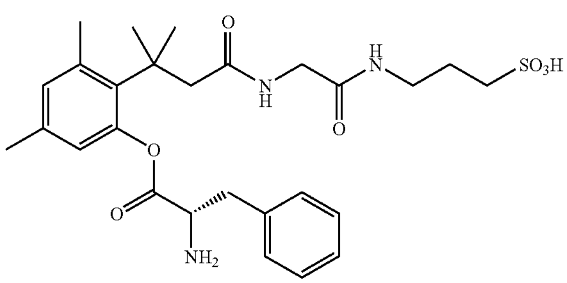 [SMILES: Cc1cc(C)c(C(C)(C)CC(=O)NCC(=O)NCCCS(=O)(=O)O)c(OC(=O)[C@@H](N)Cc2ccccc2)c1] |
| B14 | 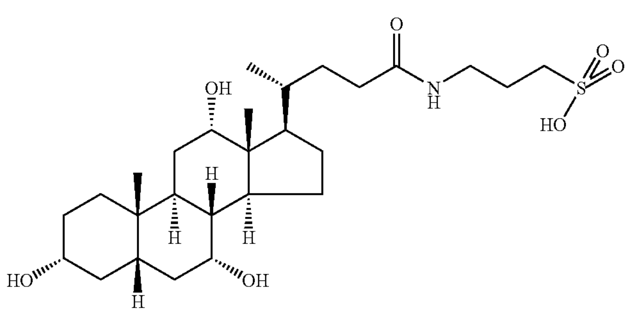 |

II-C. Carbohydrate-Derived Prodrugs

In some preferred embodiments, the compounds of the invention are carbohydrate-derived prodrugs that will yield or generate 3APS once administered in a human. Preferred prodrugs according to the invention disclosed herein comprise a carbohydrate or a polyol analog residue linked to the amine group of 3APS via a linkage, e.g. an amide, a carbamate, a urea, or a cleavable alkyl group. In one embodiment, the carbohydrate-derived moiety is, for example, a carbohydrate derivative such as hexose, pentose, a carbohydrate-derived polyol, inositol or an inositol-derived moiety, a carbohydrate-derived carboxylic acid, ascorbic acid, nucleic acid, or nucleotide. The linkage and/or carbohydrate-derived residue may be cleaved in vivo by enzymes or by any other mechanism, to liberate the amine group of 3APS.

More particularly, certain aspects of the invention relate to a compound of Formula (X), and to pharmaceutically acceptable salts, esters or solvates thereof:

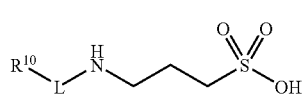

(X)

wherein, $R^{10}$ is a residue of a carbohydrate, a carbohydrate derivative or a carbohydrate-derived polyol, e.g., a $C_{5-6}$ saturated or partially or completely unsaturated cycloalkyl group, optionally and preferably containing an —O— group, which is substituted by 3 to 5 substituents, each independently selected from —OH, —OAc, —CH$_2$OH, —OCH$_3$, —CH$_2$OAc and =O.

L is a linking moiety or is absent, e.g., an alkyl group, which may be saturated or unsaturated, preferably a lower alkyl group, which is optionally interrupted by one or more —O— and/or —NH— groups, and is optionally substituted by one or more =O, —OH, and/or —NH$_2$ groups.

In one embodiment, the invention provides a compound of Formula X, wherein when L is absent, then $R^{10}$ is other than 2-deoxy-2-D-glucose.

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein. Compounds of the invention are also shown in Table 4A below.

TABLE 4A

Exemplary carbohydrate-derived prodrugs according to the invention

| ID | Structure |
|----|-----------|
| S1 | 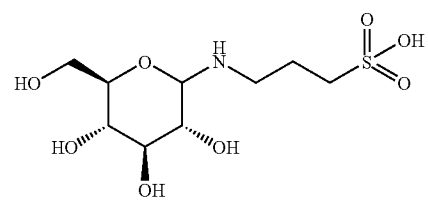 [SMILES: O=S(=O)(O)CCCNC1O[C@H](CO)[C@@H](O)[C@H](O)[C@H]1O] |
| S2 | 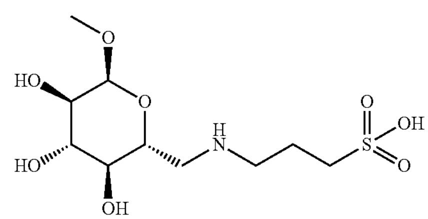 [SMILES: CO[C@H]1O[C@H](CNCCCS(=O)(=O)O)[C@@H](O)[C@H](O)[C@H]1O] |
| S3 | 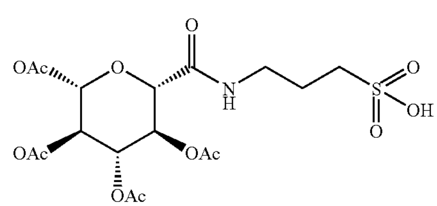 [SMILES: CC(=O)O[C@@H]1O[C@H](C(=O)NCCCS(=O)(=O)O)[C@@H](OC(C)=O)[C@H](OC(C)=O)[C@H]1OC(C)=O] |
| S4 | 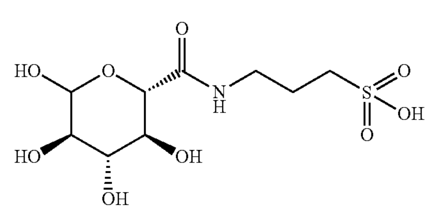 [SMILES: O=C(NCCCS(=O)(=O)O)[C@H]1OC(O)[C@H](O)[C@@H](O)[C@@H]1O] |

TABLE 4A-continued

Exemplary carbohydrate-derived prodrugs according to the invention

| ID | Structure |
|---|---|
| S5 | 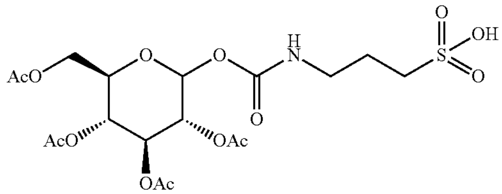 [SMILES: CC(=O)OC[C@H]1OC(OC(=O)NCCCS(=O)(=O)O)[C@H](OC(C)=O)[C@@H](OC(C)=O)[C@@H]1OC(C)=O] |
| S6 | 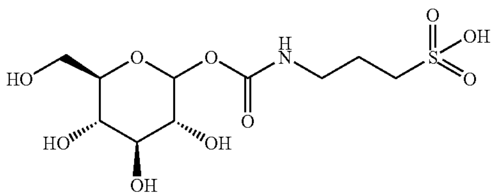 [SMILES: O=C(NCCCS(=O)(=O)O)OC1O[C@H](CO)[C@@H](O)[C@H](O)[C@H]1O] |
| S7 | 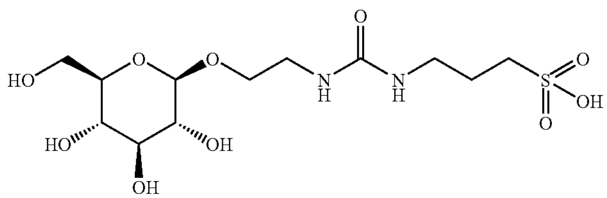 [SMILES: O=C(NCCCS(=O)(=O)O)NCCO[C@@H]1O[C@H](CO)[C@@H](O)[C@H](O)[C@H]1O] |
| S8 | 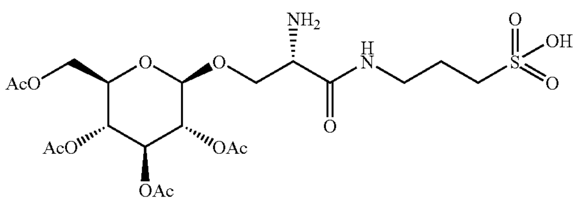 [SMILES: CC(=O)OC[C@H]1O[C@@H](OC[C@H](N)C(=O)NCCCS(=O)(=O)O)[C@H](OC(C)=O)[C@@H](OC(C)=O)[C@@H]1OC(C)=O] |
| S9 | 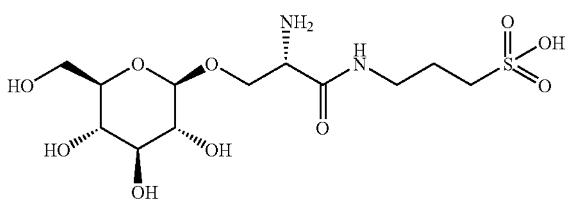 [SMILES: N[C@@H](CO[C@@H]1O[C@H](CO)[C@@H](O)[C@H](O)[C@H]1O)C(=O)NCCCS(=O)(=O)O] |
| S10 | 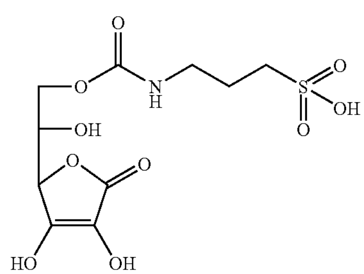 [SMILES: O=C(NCCCS(=O)(=O)O)OCC(O)C1OC(=O)C(O)=C1O] |
| S11 | 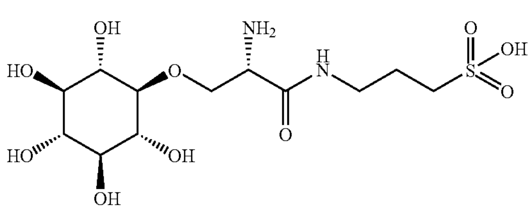 [SMILES: N[C@@H](CO[C@H]1[C@H](O)[C@@H](O)[C@H](O)[C@@H](O)[C@@H]1O)C(=O)NCCCS(=O)(=O)O] |

TABLE 4A-continued

Exemplary carbohydrate-derived prodrugs according to the invention

| ID | Structure |
|---|---|
| S12 | 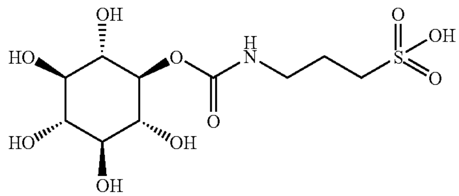 [SMILES: O=C(NCCCS(=O)(=O)O)O[C@H]1[C@H](O)[C@@H](O)[C@H](O)[C@@H](O)[C@@H]1O] |
| S13 | 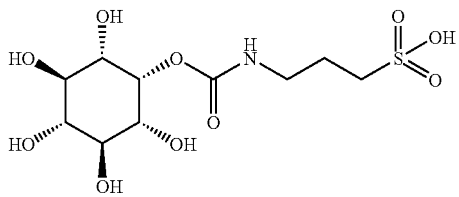 [SMILES: O=C(NCCCS(=O)(=O)O)O[C@@H]1[C@H](O)[C@@H](O)[C@H](O)[C@@H](O)[C@@H]1O] |
| S14 | 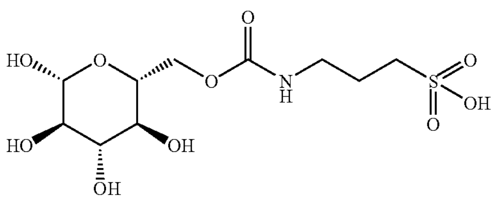 [SMILES: O=C(NCCCS(=O)(=O)O)OC[C@H]1O[C@@H](O)[C@H](O)[C@@H](O)[C@@H]1O] |
| S15 | 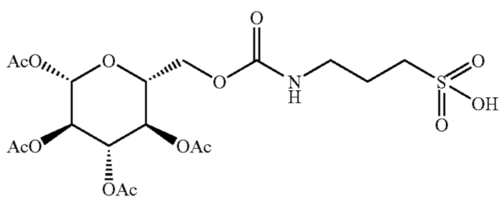 [SMILES: CC(=O)O[C@@H]1O[C@H](COC(=O)NCCCS(=O)(=O)O)[C@@H](OC(C)=O)[C@H](OC(C)=O)[C@H]1OC(C)=O] |
| S16 | 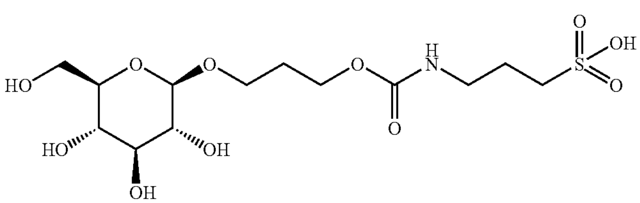 [SMILES: O=C(NCCCS(=O)(=O)O)OCCCO[C@@H]1O[C@H](CO)[C@@H](O)[C@H](O)[C@H]1O] |
| S17 | 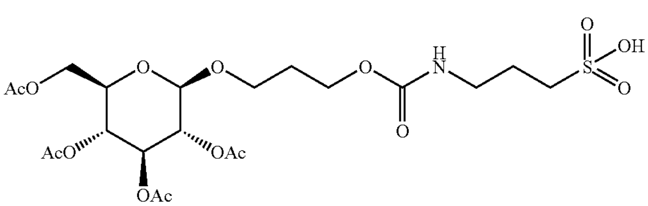 [SMILES: CC(=O)OC[C@H]1O[C@@H](OCCCOC(=O)NCCCS(=O)(=O)O)[C@H](OC(C)=O)[C@@H](OC(C)=O)[C@@H]1OC(C)=O] |

II-D. Other Prodrugs

In some preferred embodiments, the compounds of the invention are N-hydroxy prodrugs and derivatives, cyclic double-protected prodrugs, precursors of 3APS, as prodrugs that will yield or generate 3APS once administered in a human.

a) N-Hydroxy-Derived Prodrugs

More particularly, certain aspects of the invention relate to a compound of Formula (XI), and to pharmaceutically acceptable salts, esters or solvates thereof:

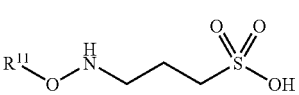
(XI)

wherein, $R^{11}$ is a hydrogen or a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, $C_5$-$C_{15}$heteroaryl, C(O)$R^{12}$, and C(O)O$R^{13}$; and $R^{12}$ and $R^{13}$ are independently selected from substituted or unsubstituted $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, $C_5$-$C_{15}$heteroaryl.

In one embodiment, the invention provides compounds of Formula XI, wherein $R^{11}$ is other than a hydroxyl.

Compounds of the invention include compounds:

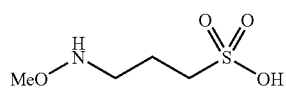

Compound H1

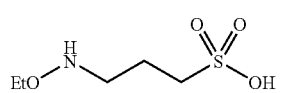

Compound H2

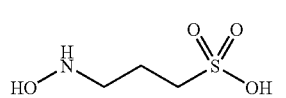

Compound H3

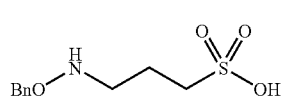

Compound H4 b) Cyclic Double-Protected Prodrugs

More particularly, certain aspects of the invention relate to a compound of Formula (XII), and to pharmaceutically acceptable salts, esters or solvates thereof:

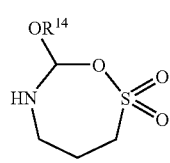

(XII)

wherein,

D is a carbonyl, an amino acid residue, or a substituted methylene group; and

X is selected from O, NH, and S.

More particularly, certain aspects of the invention relate to a compound of Formula (XII-A), and to pharmaceutically acceptable salts, esters or solvates thereof:

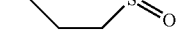

(XII-A)

wherein, $R^{14}$ is a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, $C_5$-$C_{15}$heteroaryl.

Compounds of the invention include the following compounds:

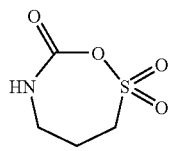

Compound D1

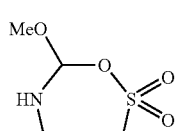

Compound D2

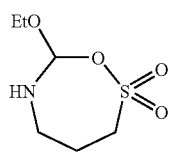

Compound D3

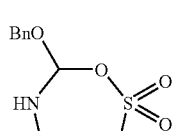

Compound D4

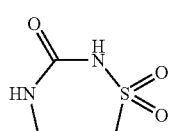

Compound D5

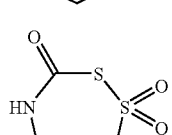

Compound D6

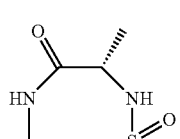

Compound D7

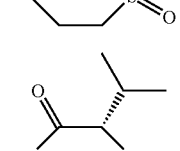

Compound D8 c) Imine Prodrugs

More particularly, certain aspects of the invention relate to a compound of Formula (XIII), and to pharmaceutically acceptable salts, esters or solvates thereof:

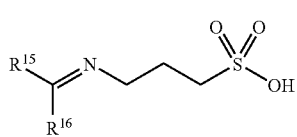

(XIII)

wherein, $R^{15}$ and $R^{16}$ are independently selected from a hydrogen or a substituted or unsubstituted group selected from $C_1$-$C_{12}$alkyl, $C_2$-$C_{12}$alkenyl, $C_2$-$C_{12}$alkynyl, $C_3$-$C_{15}$cycloalkyl, $C_3$-$C_{15}$heterocycloalkyl, $C_6$-$C_{15}$aryl, and $C_5$-$C_{15}$heteroaryl.

In one embodiment, the invention provides compounds of Formula XIII, wherein when both $R^{15}$ and $R^{16}$ are substituted or unsubstituted aryl, then at least one of $R^{15}$ and $R^{16}$ is substituted with a hydroxyl group at the ortho position. In another embodiment, the invention provides compounds of Formula XIII, wherein when both $R^{15}$ and $R^{16}$ are substituted or unsubstituted aryl, then none of $R^{15}$ and $R^{16}$ is substituted with a hydroxyl group at the ortho position.

Compounds of the invention include the following compounds:

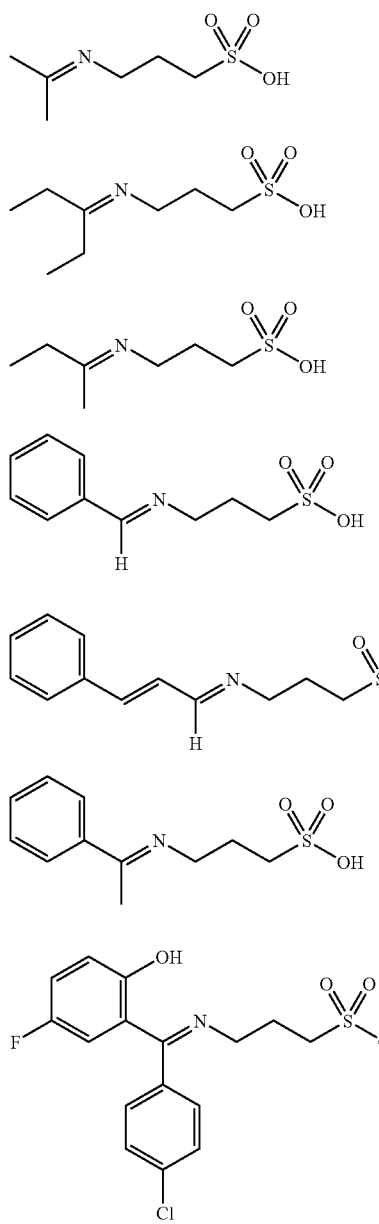

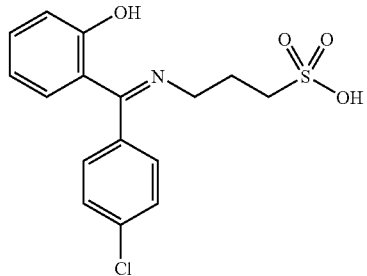

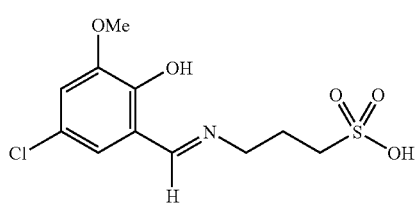

In some preferred embodiments, the compounds of the invention comprise a combination of any of the prodrugs described herein in sections II-A to II-D, as prodrugs that will yield or generate 3APS once administered in a human. The invention further relates to sulfonic acid precursors of any of the prodrugs mentioned in Sections II-A to II-D, including sulfonate esters, sulfonamides, sulfinic acids, sulfides, disulfides and the like.

II-E. Oligomers and Gemini Dimers

In a further embodiment the compound of the Formula I may comprise two or more 3APS molecules linked together. Therefore, another aspect of the invention relates to polymers of 3APS, i.e., a molecule comprising, or consisting essentially of, or consisting of two or more molecules of 3APS linked together with cleavable linkage. Thus, another aspect of the invention relates to a compound of the Formula I-P:

$$A\text{-}(L^x\text{-}A)_p\text{-}L^x\text{-}A \qquad (I\text{-}P)$$

as well as pharmaceutically acceptable salts, esters, metabolites, and solvates thereof, where:

A is 3-amino-1-propanesulfonic acid moiety;

$L^x$ is a cleavable linkage for covalently and dissociably coupling together two adjacent 3APS moieties, and p is 0, or an integer number which may vary from 1 to 5, e.g. 2, 3, 4, or 5.

Those skilled in the art will readily understand that there can be a great number of possible variations or orientations for coupling together three or more 3APS moieties (the number of possibilities being $2^{n-1}$, n being equal to 3 for a trimer (4 possibilities), n=4 for tetramer (8 possibilities), etc). Indeed, as exemplified with more details hereinafter with gemini dimers, such connections could be made via the $NH_2$ group or the $SO_3H$ group of the 3APS molecule. For instance, for a trimer of 3APS (i.e., 3 molecules of 3APS), there would be 4 different possibilities:

the symbol "♦" representing the NH$_2$ group of the 3APS molecule, the symbol "—" the SO$_3$H group of the 3APS molecule, and the symbol "*" representing the position of the linkage.

Alternatively, the invention relates to a compound of Formula I-P2:

$$L^y(A)_m \qquad (I\text{-}P2)$$

and pharmaceutically acceptable salts, esters, and solvates thereof, where:

m is an integer from 2 to 5;

A is 3-amino-1-propanesulfonic acid moiety;

L$^y$ is a multivalent carrier moiety for covalently and dissociably coupling from two to five A moieties, either at the amino or sulfonic acid end of A.

In preferred embodiments, the compounds of the Formula I-P comprise or are "Gemini dimers" i.e., they comprise two 3APS molecules linked together with a cleavable linkage. Thus, in another aspect, the invention relates to compounds of Formula I-C (and salts, esters and solvates thereof):

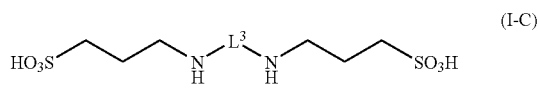
(I-C)

wherein, L$^3$ is bivalent linker which connects two molecules of 3APS at their amino groups either using the same or different linkages as defined herein, including, but not limited to, amide linkage and carbamate linkage.

In another aspect, the invention relates to compounds of Formula I-D (and salts, esters, and solvates thereof):

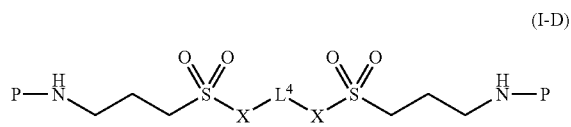
(I-D)

wherein, L$^4$ is a bivalent linker which connects two molecules of 3APS at their sulfonic acid groups either using the same or different linkages as defined herein, including, but not limited to, ester linkage or anhydride linkage where X is oxygen, or sulfonamide linkage where X is nitrogen (NH, or NR), or thiosulfonate linkage where X is sulfur. P is hydrogen or a N-protecting group as defined herein.

In another aspect, the invention relates to compounds of Formula I-E (and salts, esters, and solvates thereof):

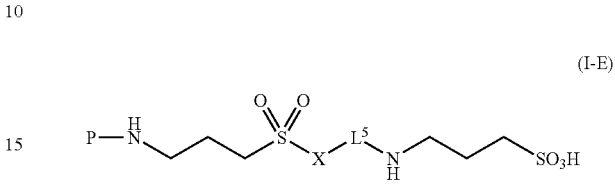
(I-E)

wherein, L$^5$ is a bivalent linker which connects two molecules of 3APS, at amino group in one 3APS using a linkage as defined in Formula I-C, and at sulfonic acid group in the other 3APS using a linkage as defined in Formula I-D. P is hydrogen or a N-protecting group as defined herein.

In preferred embodiment, the linker L$^x$, L$^3$, L$^4$, or L$^5$, or the carrier moiety L$^y$ are selected such that the two, three, four or five linked 3APS moieties may be converted in vitro or in vivo, directly or indirectly, to release two, three, four or five pharmaceutically active 3APS molecules. The capability of releasing the parent 3APS molecule(s) may be tested and, in many cases, it can be predicted. More preferably, the linker is designed to bind the 3APS molecules via their nitrogen atoms (for improved protection against first pass metabolism), but as exemplified hereinbefore, it is also possible to bind the 3APS molecules via the oxygen atom of their sulfonate group (e.g., through an ester-type of linkage) or via their sulfur atom (e.g., sulfonamide linked dimers). Various permutations of the above are also possible. Those skilled in the art will be capable to select proper linkers and linkage site and test the resulting product for efficacy and for capability of cleavage under various chemical and/or biological conditions. Compounds of the invention are also shown in Table 4B below.

TABLE 4B

Exemplary gemini dimers according to the invention

| ID | Structure |
|---|---|
| G1 | 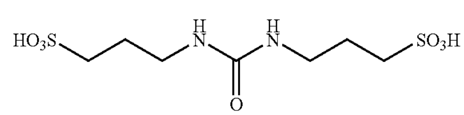 [SMILES: O=C(NCCCS(=O)(=O)O)NCCCS(=O)(=O)O] |
| G2 | 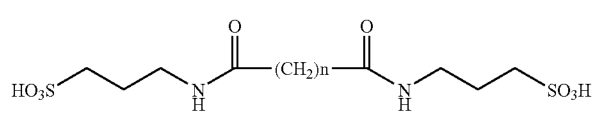 |
| G3 | 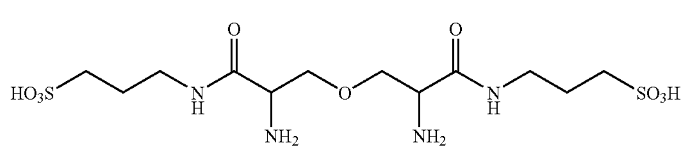 [SMILES: NC(COCC(N)C(=O)NCCCS(=O)(=O)O)C(=O)NCCCS(=O)(=O)O] |

TABLE 4B-continued

Exemplary gemini dimers according to the invention

| ID | Structure |
|---|---|
| G4 | (structure) |
| G5 | (structure) |
| G6 | (structure) |
| G7 | (structure) |
| G8 | (structure) |
| G9 | (structure) |
| G10 | (structure) |

TABLE 4B-continued

Exemplary gemini dimers according to the invention

| ID | Structure |
|---|---|
| G11 | (structure: HO-S(=O)(=O)-CH2CH2CH2-NH-C(=O)-[benzene ring with meta-disubstitution and a 5-SO2NH2 group]-C(=O)-NH-CH2CH2CH2-S(=O)(=O)-OH) |

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein.

III. Synthesis of the Compounds of the Invention

In general, all compounds of the present invention may be prepared by the methods illustrated in the Examples hereinafter and/or other conventional methods, using readily available and/or conventionally preparable starting materials, reagents and conventional synthesis procedures. In these reactions, it is also possible to make use of variants which are in themselves known, but are not mentioned here. Certain novel and exemplary methods of preparing the inventive compounds are described in the Exemplification section. Such methods are within the scope of this invention. Functional and structural equivalents of the compounds described herein and which have the same general properties, wherein one or more simple variations of substituents are made which do not adversely affect the essential nature or the utility of the compound are also included.

More particularly, the amino acid prodrugs of the present invention may be prepared by the methods illustrated in Example 1-A hereinafter, and in general reaction schemes such as, for example, described in Schemes 1 and 2, or by modifications thereof.

The carbamate prodrugs of the present invention may be prepared by the methods illustrated in Example 1-B hereinafter, or by modifications thereof.

The non-amino acid prodrugs of the present invention may be prepared by the methods illustrated in Example 1-C hereinafter, and in the general reaction schemes such as, for example, the amide coupling steps described in Schemes 1 and 2, or by modifications thereof.

The carbohydrate-derived prodrugs may be prepared by the methods illustrated in Example 1-D hereinafter, or by known coupling reactions depending on the linkage used (carbamate, urea, amide, and the like), or by modifications thereof.

The N-hydroxy prodrugs and their derivatives may be prepared by oxidation of the amine group, and by alkylating such N-hydroxy group when desired. The procedures to accomplish these reactions are readily available and known to the skilled artisan.

The cyclic double-protected prodrugs are prepared according to standard procedures for the cyclization of such groups, depending on the D and X groups used.

The compounds of the present invention may be readily prepared in accordance with the synthesis schemes and protocols described herein, as illustrated in the specific procedures provided. However, those skilled in the art will recognize that other synthetic pathways for forming the compounds of this invention may be used, and that the following is provided merely by way of example, and is not limiting to the present invention. See, e.g., "Comprehensive Organic Transformations" by R. Larock, VCH Publishers (1989). It will be further recognized that various protecting and deprotecting strategies will be employed that are standard in the art (See, e.g., "Protective Groups in Organic Synthesis" by Greene and Wuts (1991)). Those skilled in the relevant arts will recognize that the selection of any particular protecting group (e.g., amine, hydroxyl, thio, and carboxyl protecting groups) will depend on the stability of the protected moiety with regards to the subsequent reaction conditions and will understand the appropriate selections.

Further illustrating the knowledge of those skilled in the art is the following sampling of the extensive chemical literature: "Chemistry of the Amino Acids" by J. P. Greenstein and M. Winitz, John Wiley & Sons, Inc., New York (1961); "Advanced Organic Chemistry: Reactions, Mechanisms, and Structure" by J. March, 4th Edition, John Wiley & sons (1992); T. D. Ocain, et al., *J. Med. Chem.*, 31, 2193-99 (1988); E. M. Gordon, et al., J. Med. Chem. 31, 2199-10 (1988); "Practice of Peptide Synthesis" by M. Bodansky and A. Bodanszky, Springer-Verlag, New York (1984); "Asymmetric Synthesis: Construction of Chiral Molecules Using Amino Acids" by G. M. Coppola and H. F. Schuster, John Wiley & Sons, Inc., New York (1987); "The Chemical Synthesis of Peptides" by J. Jones, Oxford University Press, New York (1991); and "Introduction of Peptide Chemistry" by P. D. Bailey, John Wiley & Sons, Inc., New York (1992).

The synthesis of compounds of the invention is preferably carried out in a solvent. Suitable solvents are liquids at ambient room temperature and pressure or remain in the liquid state under the temperature and pressure conditions used in the reaction. The choice of solvent is within the general skills of the skilled artisan and will depend on the reaction conditions, such, temperature, the nature of the reagents and starting material, solubility and stability of the reagents and starting material, the type of reaction, and the like. Depending on the circumstances, solvents may be distilled or degassed. Solvents may be, for example, aliphatic hydrocarbons (e.g., hexanes, heptanes, ligroin, petroleum ether, cyclohexane, or methylcyclohexane) and halogenated hydrocarbons (e.g., methylenechloride, chloroform, carbontetrachloride, dichloroethane, chlorobenzene, or dichlororbenzene); aromatic hydrocarbons (e.g., benzene, toluene, tetrahydronaphthalene, ethylbenzene, or xylene); ethers (e.g., diglyme, methyl-tert-butyl ether, methyl-tert-amyl ether, ethyl-tert-butyl ether, diethylether, diisopropylether, tetrahydrofuran or methyltetrahydrofurans, dioxane, dimethoxyethane, or diethyleneglycol dimethylether); amides (e.g., N,N-dimethylformamide, N,N-dimethylacetamide); nitriles (e.g., acetonitrile); ketones (e.g., acetone); esters (e.g., methyl acetate or ethyl acetate); alcohols (e.g., methanol, ethanol, isopropanol); water and mixtures thereof.

"Activated esters" and equivalent expressions may be represented by the formula COX, where X is a leaving group, typical examples of which include N-hydroxysulfosuccinimidyl and N-hydroxysuccinimidyl groups; aryloxy groups substituted with electron-withdrawing groups (e.g., p-nitro, pentafluoro, pentachloro, p-cyano, or p-trifluoromethyl); and carboxylic acids activated by a carbodiimide or other conventional coupling reagents to form an anhydride or mixed anhydride, e.g., —OCOR$^a$ or —OCNR$^a$NHR$^b$, where R$^a$ and R$^b$ are independently $C_1$-$C_6$ alkyl, $C_5$-$C_8$ alkyl (e.g., cyclohexyl), $C_1$-$C_6$ perfluoroalkyl, or $C_1$-$C_6$ alkoxy groups. An activated ester may be formed in situ or may be an isolable reagent. The ester leaving group may be, for example, sulfosuccinimidyl esters, pentafluorothiophenol esters, sulfotetrafluorophenol, substituted or unsubstituted $C_1$-$C_6$ alkyl (such as methyl, ethyl, propyl, isopropyl, butyl, isobutyl, sec-butyl, tert-butyl, pentyl, or hexyl), or substituted or unsubstituted $C_6$-$C_{14}$ aryl or heterocyclic groups, such as 2-fluoroethyl, 2-chloroethyl, 2-bromoethyl, 2,2-dibromoethyl, 2,2,2-trichloroethyl, 3-fluoropropyl, 4-chlorobutyl, methoxymethyl, 1,1-dimethyl-1-methoxymethyl, ethoxymethyl, N-propoxymethyl, isopropoxymethyl, N-butoxymethyl, tert-butoxymethyl, 1-ethoxyethyl, 1-methyl-1-methoxyethyl, 1-(isopropoxy)ethyl, 3-methoxypropyl-4-methoxybutyl, fluoromethoxymethyl, 2,2,2-trichloroethoxymethyl, bis(2-chloroethoxy)methyl, 3-fluoropropoxymethyl, 4-chlorobutoxyethyl, dibromomethoxyethyl, 2-chloroethoxypropyl, fluoromethoxybutyl, 2-methoxyethoxymethyl, ethoxymethoxyethyl, methoxyethoxypropyl, methoxyethoxybutyl, benzyl, phenethyl, 3-phenylpropyl, 4-phenylbutyl, α-naphthylmethyl, β-naphthylmethyl, diphenylmethyl, triphenylmethyl, α-naphthyldipheylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, or bis(2-nitrophenyl)methyl groups.

III. Exemplary Synthesis of Amino Acid Prodrugs According to the Invention

The following schemes are for illustration purposes and are not intended to be limiting. The coupling of 3-amino-1-propanesulfonic acid with a first amino acid may be generally represented by Scheme 1:

Scheme 1:

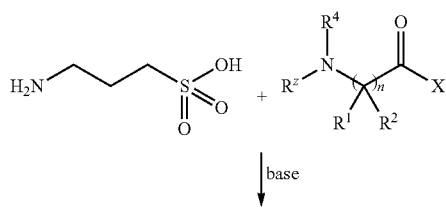

-continued

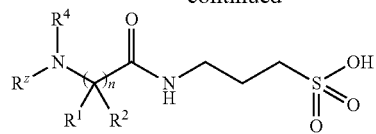

wherein $R^1$, $R^2$ and $R^4$ are as previously disclosed, $R^z$ is $R^3$ or a protecting group, and X is the leaving group of an activated ester.

In Scheme 1, a monoamino acid prodrug of 3-amino-1-propanesulfonic acid is produced by reacting its free amino group (or a protected sulfonate ester variant) with an activated ester of the desired amino acid (which may be N-protected). Group C(O)X of the activated ester may be an acyl halide, mixed anhydride, succinimide ester, or may be a carboxylic acid activated by a peptide coupling agent (e.g., carbodiimides (such as EDC (1-(3-dimethylaminopropyl)-3-diisopropylethylcarbodiimide)) and uroniums (such as HATU (O-(7-azabenzotriazol-1-yl)-N,N,N',N'-tetramethyluronium hexafluorophosphate))), in the presence of a base (e.g., amines (such as DIPEA (N,N-diisopropylethylamine), hydroxides (such as sodium hydroxide), carbonates (such as potassium carbonate), etc), and optionally a catalyst (e.g. 4-(dimethylamino)pyridine (DMAP), 1-hydroxybenzotriazole (HOBt)). The choice of base and catalyst will depend mainly on the nature of the activated ester.

At this stage, protecting groups ($R^z$ on amine or protecting groups present on heteroatoms in $R^1$ and $R^2$ groups) may be removed. Protecting groups on heteroatoms other than on the amine may not be removed if further amino acid couplings are necessary (see Scheme 2). Protecting groups of oxygen atoms may include benzyl and silyl ethers, acetals and esters, protecting groups of nitrogen may include carbamates and fluorene derivatives. They are cleaved by widely used procedures (see, for example, Greene and Wuts (1991), supra).

Scheme 2:

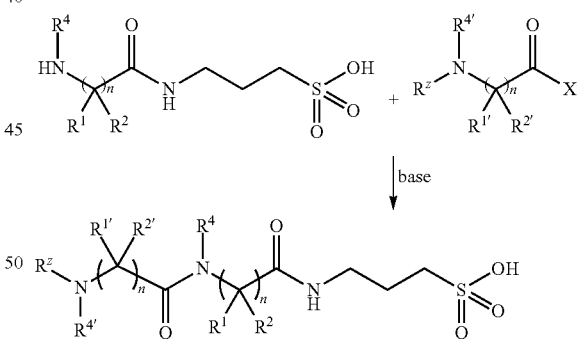

wherein $R^{1'}$, $R^{2'}$ and $R^{4'}$ are defined respectively as $R^1$, $R^2$ and $R^4$ but may or may not be the same as $R^1$, $R^2$ and $R^4$ in the above scheme, and $R^1$, $R^2$, $R^4$, $R^z$ and X are as previously disclosed.

Scheme 2 is used to produce prodrugs comprising two or more amino acids attached to 3APS. Coupling conditions are generally the same as described for Scheme 1. Subsequent amino acids are added in the same manner, with a deprotection of the amine group between each coupling step. If other protecting groups are present on heteroatoms of the residues, they may be removed during a last chemical step.

In general, after completion of the reaction, the product is isolated from the reaction mixture according to standard techniques. For example, the solvent is removed by evaporation or filtration if the product is solid, optionally under reduced pressure. After the completion of the reaction, water may be added to the residue to make the aqueous layer acidic or basic and the precipitated compound filtered, although care should be exercised when handling water-sensitive compounds. Similarly, water may be added to the reaction mixture with a hydrophobic solvent to extract the target compound. The organic layer may be washed with water, dried over anhydrous magnesium sulfate or sodium sulfate, and the solvent is evaporated to obtain the target compound. The target compound thus obtained may be purified, if necessary, e.g., by recrystallization, reprecipitation, chromatography, or by converting it to a salt by addition of an acid or base.

IV. Alternate Routes and Vehicles for Delivering 3APS by Minimizing or Lessening Hepatic First-Pass Metabolism As indicated hereinbefore, an aspect of the invention concerns new routes of administration (e.g. transdermally, subcutaneously, intranasally, etc.) and new pharmaceutical vehicles (e.g. patches, implants, spray, formulations (including for oral administration)) for lessening hepatic first-pass metabolism of 3APS.

Transdermal Drug Delivery Devices

The delivery of drugs by the transdermal route is an area of increasing interest and offers the advantage of allowing a prolonged, steady input of drug into the blood. Transdermal delivery of 3APS is one preferred embodiment of the invention because it could avoid hepatic first-pass metabolism that is associated with administration of 3APS, and thus increase the therapeutic effectiveness of 3APS. Transdermal delivery may also help avoid the pain associated with injections, and may increase dosage compliance.

Accordingly, certain aspects of the present invention relate to a method for the delivery of a compound according to the invention, preferably 3APS, to improve the effectiveness of the compound in the treatment of cognitive disorders. The invention further relates to a method of delivering a compound according to the invention, preferably 3APS, wherein the compound may be administered in a transdermal patch.

Transdermal drug delivery devices according to the invention can be manufactured using techniques and components well known to the skilled artisan. Transdermal drug delivery devices typically involve includes a backing layer, which may optionally be composed of a pigmented polyester film, a drug reservoir, a microporous membrane that controls the rate of delivery of the drug from the system to the skin surface, and an adhesive formulation to attach the delivery system to a subject. Optionally, the adhesive formulation may include the drug, thus providing a more immediate bolus of the compound upon application of the patch to a subject.

Transdermal drug delivery devices also typically involve a carrier (such as a liquid, gel, or solid matrix, or a pressure sensitive adhesive) into which the drug to be delivered is incorporated. The drug-containing carrier is then placed on the skin and the drug, along with any adjuvants and excipients, is delivered to the skin. Typically the portions of the carrier that are not in contact with the subject's skin are covered by a backing. The backing serves to protect the carrier (and the components contained in the carrier, including the drug) from the environment and prevents loss of the ingredients of the drug delivery device to the environment. Because hydration of the stratum corneum is known to enhance transport of certain drugs across the skin, it is sometimes desirable that the backing have a relatively low moisture vapor transmission rate in order to retain moisture at the site covered by the drug delivery device. In order to maintain the health of the covered skin during long term wear (e.g., for periods in excess of a day) by allowing the skin to breath, it is also desirable that the backing have relatively high permeability to oxygen. Further, as the backing is in contact with the components of the carrier, including the drug and any adjuvants and excipients, it is important that the backing be stable to such components in order that the backing retains its structural integrity, tensile strength, and conformability to the skin. It is also desirable that the backing not absorb drug or other excipients from the carrier. In connection with the preparation of certain reservoir-type transdermal drug delivery devices, it is also desirable for the backing to be heat sealable at a relatively low temperature to itself and to a variety of other polymeric substrates. Backing materials that have found use in transdermal drug delivery devices include metal foils, metalized plastic films, and single layered and multilayered polymeric films (see U.S. Pat. No. 5,264,219).

Membranes useful in the construction of a transdermal patch are known in the art and include, but are not limited to, CoTran™ membranes commercially available from 3M, such as the COTRAN™ 9701, 9702, 9705, 9706, 9715, 9716, 9726, and COTRAN™ 9728 membranes. Backing useful in the construction of a transdermal patch are known in the art and include, but are not limited to, backing material commercially available from 3M, such as COTRAN™ and SCOTCHPAK™ backings. Likewise, liners are well known in the art and may be obtained from a number of commercial sources. Optionally, a gelling agent may be optionally added at up to 20% by volume. Gelling agents, include, but are not limited to: crosslinked acrylic acid polymers, such as the "carbomer" family of polymers, e.g., carboxypolyalkylenes that may be obtained commercially under the tradename CARBOPOL™; hydrophilic polymers, such as polyethylene oxides, polyoxyethylene-polyoxypropylene copolymers and polyvinylalcohol; cellulosic polymers, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin.

Those skilled in the art will readily identified the proper combination and/or concentration of backing layer, drug reservoir, membrane, carrier, backing, penetration enhancer, gelling agent, etc. If necessary, one could refer to the numerous publications on the subject, including the patent literature such as EP 1 602 367, US 2005/019384, US 2005/0074487 and US 2005/175680 all describing transdermal drug delivery devices and associated. For instance, the absorption through human skin of a drug may be used to determine the feasibility of transdermal delivery with a particular carrier or vehicle. For example, penetration of a compound according to the invention, preferably 3APS, across human epidermis may be measured in vitro using glass diffusion cells. Therefore, optimization of the compound's absorption is achieved by use of formulations disclosed herein and known in the art as penetration enhancers. Additional well known tests and assays include permeability rate studies, absorption studies, diffusion assays, time-course profiling for penetration across human epidermis, irritancy studies, etc.

Clinical studies indicate that an oral dose of a 3APS of about 100 and/or 150 mg bid may produce a beneficial treatment for cognitive disorders, such as AD. Since transdermal administration of a compound according to the invention, preferably 3APS, is believed to be subject to reduced first-pass metabolism, the dosage of a 3APS may be reduced when administered transdermally. On the other hand, transdermal administration could be helpful to increase the dosage of 3APS by avoiding common side effects such as gastrointestinal irritation associated with an oral administration of that drug.

A benefit of a transdermal dosage form includes improved subject compliance, due to the possibility of reduced administrations. For example, a transdermal patch of the invention may be formulated so as to provide one, two, three, four, five, six or seven days of medication. In an exemplary embodiment, the transdermal patch provides medication for about three days, before it is desirable to replace the patch. In another exemplary embodiment, the transdermal patch provides seven days of medication, before it is desirable to replace the patch. In addition, the transdermal dosage may be formulated with any desirable dosage of a compound according to the invention. For example, the transdermal dosage may provide the equivalent dosage to oral administration of 100 mg bid, 150 mg bid, 200 mg bid, 250 mg bid, 300 mg bid, 350 mg bid, or 400 mg bid. As such, a transdermal patch(es) having the equivalent dosage to oral administration of 150 mg bid may be administered to a subject for a desired period of time, for example, four weeks, and then a patch or patches having the equivalent dosage to oral administration of 200 mg bid may be administered for a desired period of time.

Also included within the invention is a kit, which may contain a desired supply of patches, for example, a one month supply of transdermal patches. Optionally, a kit may be organized into a plurality of, e.g., three, differently identified (numbered, colored or the like) parts, wherein the contents of a first part are initially administered, followed by administration of the contents of a second part, which are then followed by administration of the contents of the third part. Alternatively, a kit may contain a combination of patches and oral formulations.

V. Subjects and Patient Populations

The term "subject" includes living organisms in which AD-amyloidosis can occur, or which are susceptible to Aβ-amyloid diseases, e.g., Alzheimer's disease, etc. Examples of subjects include humans, chickens, ducks, Peking ducks, geese, monkeys, deer, cows, rabbits, sheep, goats, dogs, cats, mice, rats, and transgenic species thereof. The term "subject" preferably includes animals susceptible to states characterized by neuronal cell death, e.g. mammals, e.g. humans. The animal can be an animal model for a disorder, e.g., a transgenic mouse with an Alzheimer's-type neuropathology. In preferred embodiments, the subject is a mammal, more preferably a human subject.

The term "human subject" includes humans susceptible to benefit from 3APS administration, and more particularly those susceptible to or diagnosed of having an amyloid-β related disease and/or suffering from a neurodegenerative disease, such as Alzheimer's disease, Parkinson's disease, etc.

In certain embodiments of the invention, the human subject is in need of treatment by the methods of the invention, and is selected for treatment based on this need. A subject in need of treatment is art-recognized, and includes subjects that have been identified as having a disease or disorder related to β-amyloid deposition, has a symptom of such a disease or disorder, or is at risk of such a disease or disorder, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

For example, the human subject may be a human over 30 years old, human over 40 years old, a human over 50 years old, a human over 60 years old, a human over 70 years old, a human over 80 years old, a human over 85 years old, a human over 90 years old, or a human over 95 years old. The subject may be a female human, including a postmenopausal female human, who may be on hormone (estrogen) replacement therapy. The subject may also be a male human. In another embodiment, the subject is under 40 years old.

In preferred embodiments, the subject is a human subject having an Alzheimer's-type neuropathology. Individuals presently suffering from Alzheimer's disease can be recognized from characteristic dementia, as well as the presence of risk factors described below. In addition, a number of diagnostic tests based on cognitive and neurological testing are available for identifying individuals who have AD. For example, individuals suffering from Alzheimer's disease can be diagnosed by the Clinical Dementia Rating (CDR) scale, Mini-mental State Examination (MMSE), Alzheimer's Disease Assessment Scale-Cognitive Subscale (ADAS-Cog), or any other test known in the art, as discussed herein. Baseline scores on suitable metrics including the MMSE and the ADAS together with other metrics designed to evaluate a more normal population can be used to find an at risk population. Another method for identifying an at risk group utilizes an assay for neural thread protein in the urine; see, e.g., Munzar et al., *Neurology and Clinical Neurophysiology, Vol.* 2002, No. 1. Patients with high risk for Alzheimer's Disease can also be selected from a population by screening for early signs of memory loss or other difficulties associated with pre-Alzheimer's symptomatology, a family history of Alzheimer's Disease, patients with Mild Cognitive Impairment (MCI), genetic risk factors, age, sex, and other features found to predict high-risk for Alzheimer's Disease.

The term "prevention" or "preventing" is also used to describe the administration of a compound or composition of the invention to a subject who is at risk of (or susceptible to) such a disease or condition. Patients amenable to treatment for prevention of the disease or condition include individuals at risk of the disease or condition but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without any assessment of the risk of the subject patient. But the present methods are especially useful for individuals who do have a known risk of Alzheimer's disease. Such individuals include those having relatives who have experienced this disease, and those whose risk is determined by analysis of genetic or biochemical markers, including brain plaques diagnosed by imaging methods, e.g., MRI, PET, SPECT etc. Examples of such imaging methods are discussed in Burggren et al., *Current Topics in Medicinal Chemistry*, vol. 2002, no. 2, pp. 385-393, and Sair et al., *Neuroradiology*, vol. 46, pp. 93-104 (2002). Alzheimer's disease predisposing factors identified or proposed in the scientific literature include, among others, a genotype predisposing a subject to Alzheimer's disease; environmental factors predisposing a subject to Alzheimer's disease; past history of infection by viral and bacterial agents predisposing a subject to Alzheimer's disease; and vascular factors predisposing a subject to Alzheimer's disease. Genetic markers of risk toward Alzheimer's disease include mutations in the APP gene, particularly mutations at position 717 and positions 670 and 671 referred to as the Hardy and Swedish mutations respectively (see Hardy et al., TINS 20, 154-158 (1997)). Other markers of risk are mutations in the presenilin genes, PS1 and PS2, and ApoE4, family history of AD, hypercholesterolemia or atherosclerosis. The subject may be shown to be at risk by a diagnostic brain imaging technique, for example, one that measures brain activity, plaque deposition, or brain atrophy. The human subject may also be shown to be at risk by a cognitive test such as Clinical Dementia Rating ("CDR"), Alzheimer's disease Assessment Scale-Cognition ("ADAS-Cog"), Disability Assessment for Dementia ("DAD") or Mini-Mental State Examination ("MMSE") and/or by any other cognition test known in the art.

In another embodiment, the human subject exhibits no symptoms of Alzheimer's disease. In another embodiment, the subject is at least 40 years of age and exhibits no symptoms of Alzheimer's disease. In another embodiment, the human subject is at least 40 years of age and exhibits one or more symptoms of Alzheimer's disease.

By using the methods and compounds of the present invention, the levels of amyloid peptides in a subject's plasma or cerebrospinal fluid (CSF) could be significantly reduced from levels prior to treatment from about 10 to about 100 percent, or even about 50 to about 100 percent, e.g., 15, 25, 40, 60, 70, 75, 80, 90, 95 or 99%. Accordingly, in certain embodiments, the human subject can have an elevated level of amyloid $A\beta_{40}$ and $A\beta_{42}$ peptide in the blood and/or CSF prior to a treatment according to the present methods, e.g. $A\beta_{40}$ levels of greater than about 10 pg/mL, or greater than about 20 pg/mL, or greater than about 35 pg/mL, or even greater than about 40 pg/mL; and $A\beta_{42}$ levels 30 pg/mL to about 200 pg/mL, or even to about 500 pg/mL. Similarly, according to some embodiments, the methods and compounds of the present invention help reduce the size and/or number of Aβ plaques or Aβ deposits in the brain, from about 10 to about 100 percent, or even about 50 to about 100 percent, e.g., 15, 25, 40, 60, 70, 75, 80, 90, 95 or 99%, when compared to levels prior to treatment.

VI. Pharmaceutical Compositions

Preferably, the compounds of the invention are formulated prior to administration into pharmaceutical compositions using techniques and procedures well known in the art. Accordingly, in another embodiment, the present invention relates to pharmaceutical compositions (e.g. solutions, suspensions or emulsions) comprising effective amounts of one or more compounds according to any of the Formulae herein and a pharmaceutically acceptable vehicle, as well as methods of using and manufacturing such pharmaceutical compositions.

The pharmaceutical compositions are formulated into suitable administration (orally, parenterally, (IV, IM, depo-1M, SC, and depo SC), sublingually, intranasally (inhalation), intrathecally, topically, or rectally). Suitable pharmaceutically acceptable vehicles include, without limitation, any non-immunogenic pharmaceutical carrier or diluent suitable for oral, parenteral, nasal, mucosal, transdermal, topical, intrathecal, rectal, intravascular (IV), intraarterial (IA), intramuscular (IM), and subcutaneous (SC) administration routes, such as phosphate buffer saline (PBS). Also, the present invention includes such compounds which have been lyophilized and which may be reconstituted to form pharmaceutically acceptable formulations for administration, as by intravenous, intramuscular, or subcutaneous injection. Administration may also be intradermal or transdermal.

The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Preferably, the compound(s) of the invention can be orally administered. Formulations of the present invention include those suitable for oral administration. The formulations may conveniently be presented in unit dosage form and may be prepared by any methods well known in the art of pharmacy. Methods of preparing these formulations or compositions include the step of bringing into association a compound of the present invention with a pharmaceutically acceptable vehicle (e.g. an inert diluent or an assimilable edible carrier) and, optionally, one or more accessory ingredients. In general, the formulations are prepared by uniformly and intimately bringing into association a compound of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g. hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) or as mouth washes and the like, each containing a predetermined amount of a compound of the present invention as an active ingredient. A compound of the present invention may also be administered as a bolus, electuary or paste, or incorporated directly into the subject's diet. Moreover, in certain embodiments these pellets can be formulated to (a) provide for instant or rapid drug release (i.e., have no coating on them); (b) be coated, e.g., to provide for sustained drug release over time; or (c) be coated with an enteric coating for better gastrointestinal tolerability.

In solid dosage forms of the invention for oral administration the active ingredient is mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions suitable for injectable use include sterile aqueous solutions (where water soluble) or dispersions, and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Pharmaceutical formulations are also provided which are suitable for administration as an aerosol, by inhalation. These formulations comprise a solution or suspension of the desired compound of any Formula herein or a plurality of solid particles of such compound(s). The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of an agent of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included. The compound(s) of the invention may also be administered parenterally, intraperitoneally, intraspinally, or intracerebrally. For such compositions, the compound(s) of the invention can be prepared in glycerol, liquid polyethylene glycols, and mixtures thereof and in oils. Under ordinary conditions of storage and use, these preparations may contain a preservative to prevent the growth of microorganisms.

To administer the compound(s) of the invention by other than parenteral administration, it may be useful to coat the compound(s) with, or co-administer the compound(s) with a material to prevent its inactivation. For example, the compound(s) of the invention may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutical compositions according to the invention may also be coated by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

The compound(s) of the invention may be packaged as part of a kit, optionally including a container (e.g. packaging, a box, a vial, etc). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

VII. Dosage

Dosage forms, upon releasing a compound according to the invention, can provide the corresponding 3APS upon in vivo administration to a human patient. It is understood that appropriate doses depend upon a number of factors within the knowledge of the ordinarily skilled physician, veterinarian, or researcher (e.g. see Wells et al. eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)). The dose(s) of the compound(s) of the invention will vary, for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g. bioavailability, stability, potency, toxicity, etc). Such appropriate doses may be determined using the assays described herein. When one or more of the compounds of the invention is to be administered to humans, a physician may for example, prescribe a relatively low dose at first, subsequently increasing the dose until an appropriate response is obtained.

Exemplary doses include milligram or microgram amounts of the compound per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include doses of about 5 to about 500 mg, or about 25 to about 300 mg, or about 25 to about 200 mg, preferably about 50 to about 150 mg, more preferably about 50, about 100, about 150 mg, about 200 mg or about 250 mg, and, preferably, daily or twice daily, or lower or higher amounts. For comparison, exemplary doses for 3APS per se include about 2-3 milligram of 3APS per kilogram of subject (twice daily). See also U.S. Ser. No. 11/103,656, filed on Apr. 12, 2005, which is incorporated herein by reference.

It is generally advantageous to formulate parenteral compositions in dosage unit form for ease of administration and uniformity of dosage. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical vehicle. In an embodiment, the compositions according to the invention are formulated in a unit dosage form, each dosage containing from about 50 mg to about 500 mg, more preferably about 100 mg to about 300 mg of the compound according to the invention. See also U.S. Ser. No. 11/103,656, filed on Apr. 12, 2005, which is incorporated herein by reference. The specification for the dosage unit forms of the invention may vary and are dictated by and directly dependent on (a) the unique characteristics of the therapeutic agent and the particular therapeutic effect to be achieved, and (b) the limitations inherent in the art of compounding such a therapeutic agent for the treatment of amyloid deposition in subjects.

Administration of the compounds and compositions of the present invention to a subject to be treated can be carried out using known procedures, at dosages and for periods of time effective to achieved a desired purposes (e.g. prevention or treatment of AD, obtaining specific levels of 3APS, etc). Dosage regimens can be adjusted to provide the optimum therapeutic response. For example, several divided doses may be administered daily or the dose may be proportionally reduced as indicated by the exigencies of the therapeutic situation.

In one embodiment, the compound(s) of the invention is administered at a therapeutically effective dosage sufficient to inhibit amyloid deposition in a subject, preferably a human subject. When referring to amyloid deposition a "therapeutically effective" dosage inhibits amyloid deposition by, for example, at least about 20%, or by at least about 40%, or even by at least about 60%, or by at least about 80% relative to untreated subjects.

In one embodiment, the compound(s) of the invention is administered at a therapeutically effective dosage for the prevention or treatment of Alzheimer's. When referring to Alzheimer's, a "therapeutically effective" dosage stabilizes cognitive function or prevents a further decrease in cognitive function (i.e., preventing, slowing, or stopping disease progression).

VII. Uses of Compounds, Composition, and Dosage Forms

Another aspect of the invention pertains to a method for inhibiting neuronal cell death by administering an effective amount of a compound of the present invention. In yet another aspect, the invention pertains to a method for providing neuroprotection to a subject having an Aβ-amyloid related disease, e.g. Alzheimer's disease, which includes administering an effective amount of a compound of the present invention to the subject, such that neuroprotection is provided. As used herein, the term "neuroprotection" includes protection of neuronal cells of a subject from cell death that may result in initiation of processes such as, but not limited to: the destabilization of the cytoskeleton; DNA fragmentation; the activation of hydrolytic enzymes, such as phospholipase A2; activation of caspases, calcium-activated proteases and/or calcium-activated endonucleases; inflammation mediated by macrophages; calcium influx into a cell; membrane potential changes in a cell; the disruption of cell junctions leading to decreased or absent cell-cell communication; and the activation of expression of genes involved in cell death.

According to a preferred embodiment, the compounds and compositions of the present invention are used for one or more of the following: to prevent Alzheimer's disease, to treat Alzheimer's disease, or ameliorate symptoms of Alzheimer's disease, to regulate production of or levels of amyloid β (Aβ) peptides, prevent, reduce, or inhibit amyloid deposition in a subject, and to treat or prevent of amyloid-related diseases.

The compounds and pharmaceutical compositions of the invention may act to ameliorate the course of a β-amyloid related disease using any of the following mechanisms (this list is meant to be illustrative and not limiting): slowing the rate of β-amyloid fibril formation or deposition; lessening the degree of β-amyloid deposition; inhibiting, reducing, or preventing amyloid fibril formation; inhibiting neurodegeneration or cellular toxicity induced by β-amyloid; inhibiting amyloid induced inflammation; enhancing the clearance of β-amyloid from the brain; enhancing degradation of Aβ in the brain; or favoring clearance of amyloid protein prior to its organization in fibrils, and decreasing the ratio of Aβ42:Aβ340 in the CSF or plasma. In another embodiment, the invention pertains to a method for improving cognition in a subject suffering from AD. The method includes administering an effective amount of a therapeutic compound of the invention, such that the subject's cognition is improved. The subject's cognition can be tested using methods known in the art such as the Clinical Dementia Rating ("CDR"), Mini-Mental State Examination ("MMSE"), Disability Assessment for Dementia ("DAD"), and the Alzheimer's Disease Assessment Scale-Cognition ("ADAS-Cog"). Improvement in cognition is present within the context of the present invention if there is a measurable difference between the performances of subjects treated using the methods of the invention as compared to members of a placebo group, historical control, or between subsequent tests given to the same subject. The invention also pertains to a method for treating, slowing or stopping a β-amyloid related disease associated with cognitive impairment, by administering to a subject an effective amount of a therapeutic compound of the invention, wherein the annual deterioration of the subject's cognition as measured by any of the foregoing mentioned test is improved.

It is to be understood that wherever values and ranges are provided herein, e.g., in ages of subject populations, dosages, and blood levels, all values and ranges encompassed by these values and ranges, are meant to be encompassed within the scope of the present invention. Moreover, all values in these values and ranges may also be the upper or lower limits of a range.

VIII. Combination Therapy

In certain embodiments, the compounds and composition according to the invention can be used in combination therapy with at least one other therapeutic agent. The prodrug compounds according to the invention and the at least one other therapeutic agent(s) can act additively or, in certain embodiments, synergistically. In certain embodiments, the compounds of the invention can be administered concurrently with the administration of another therapeutic agent. In certain embodiments, the compounds of the invention can be administered prior or subsequent to administration of another therapeutic agent. The at least one other therapeutic agent can be effective for treating the same or different disease, disorder, or condition.

Methods of the present invention include administration of one or more compounds or pharmaceutical compositions of the present invention and one or more other therapeutic agents provided that the combined administration does not inhibit the therapeutic efficacy of the one or more compounds of the present invention and/or does not produce adverse combination effects.

In certain embodiments, compositions of the present invention can be administered concurrently with the administration of another therapeutic agent, which can be part of the same pharmaceutical composition as, or in a different composition from, that containing the compounds of the present invention. In certain embodiments, compounds of the present invention can be administered prior or subsequent to administration of another therapeutic agent. In certain embodiments of combination therapy, the combination therapy comprises alternating between administering a composition of the present invention and a composition comprising another therapeutic agent, e.g., to minimize adverse side effects associated with a particular drug. When a compound of the present invention is administered concurrently with another therapeutic agent that potentially can produce adverse side effects including, but not limited to, toxicity, the therapeutic agent can advantageously be administered at a dose that falls below the threshold at which the adverse side effect is elicited.

In certain embodiments, a pharmaceutical composition can further comprise substances to enhance, modulate and/or control release, bioavailability, therapeutic efficacy, therapeutic potency, stability, and the like. For example, to enhance therapeutic efficacy a compound of the present invention, the compound can be co-administered with one or more active agents to increase the absorption or diffusion of the compound from the gastrointestinal tract, or to inhibit degradation of the drug in the systemic circulation. In certain embodiments, at least one compound of the present invention can be coadministered with active agents having a pharmacological effect that enhance the therapeutic efficacy of 3APS.

In certain embodiments, compounds or pharmaceutical compositions of the present invention include, or can be administered to a patient together with, another therapeutic drug that may be available over-the-counter or by prescription. U.S. patent application No. 2005/0031651 (incorporated herein by reference) provide a long but non-exhaustive list of "therapeutic drugs" that can be useful, in combination, according to the invention. Preferred therapeutic drugs to be used with the compounds or pharmaceutical compositions of the present invention are therapeutic drugs useful in the prevention or treatment of Alzheimer's Disease or its symptoms, including but not limited to donepezil (Aricept™), memantine (Namenda™), rivastigmine (Exelon™), Galanthamine (Reminyl™ and R-flurbiprofen (Flurizan™). The compounds and compositions according to the invention could also be combined with vaccines and antibodies for the prevention or treatment of AD.

In a further embodiment, the compounds of the invention can be co-administered with 3APS.

IX. Standard Methods for Testing the Compounds of the Invention

The compounds according to the invention can be further analyzed, tested or validated using a variety of in vitro assays, or in vivo assays to confirm their safety, bioavailabity, neuroprotection, their capability to deliver 3APS etc. The following are illustrative of the type of biological assays that can be conducted to assess the instant compounds.

i) Determination of Enzymatic Cleavage of Prodrugs In Vitro

For orally administered prodrugs, it is generally desirable that the prodrug remains intact (i.e., uncleaved) while in the gastrointestinal tract and be cleaved (i.e., to release the parent drug) while in the systemic circulation. A useful level of stability can at least in part be determined by the mechanism and kinetics of absorption of the prodrug by the gastrointestinal tract. A useful level of liability can at least in part be determined by the pharmacokinetics of the prodrug and parent drug in the systemic circulation. In general, prodrugs that are more stable in a Caco-2 S9 and/or pancreatin assay and are more labile in a rat plasma, human plasma, rat liver S9, and/or human liver S9 preparation can be useful as an orally administered prodrug. The results of tests, for determining the enzymatic cleavage of prodrugs in vitro can be used to select prodrugs for in vivo testing.

ii) Bioavailability of Prodrugs in vivo

Prodrugs that provide a bioavailability of the corresponding parent drug that is greater than the bioavailability provided by an equimolar dose of the parent drug administered to a patient by the same route (e.g., oral administration) can be useful as therapeutic agents. Bioavailability of the compounds of the invention and of released 3APS can be measured in vivo (humans and laboratory animals) using methods well known in the art. Example 3 herein provides an exemplary method for assessing bioavailability in mice.

iii) In Vivo Assays: Animal Models

Various animal models can be used to the efficacy and/or potency of the compound according to the invention. For example, certain transgenic animal models have been described, for example, in U.S. Pat. Nos. 5,877,399; 5,612,486; 5,387,742; 5,720,936; 5,850,003; 5,877,015, and 5,811,633, and in Ganes et al., (Nature 1995, 373:523). Preferred are animal models that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

iv) Toxicity

A variety of different parameters can be monitored to assess toxicity. Examples of such parameters include, but are not limited to, cell proliferation, monitoring activation of cellular pathways for toxicological responses by gene or protein expression analysis, DNA fragmentation, changes in the composition of cellular membranes, membrane permeability, activation of components of death-receptors or downstream signaling pathways (e.g., caspases), generic stress responses, NF-kappaB activation and responses to mitogens. Related assays are used to assay for apoptosis (a programmed process of cell death) and necrosis, including cGMP formation and NO formation.

Toxicity and therapeutic efficacy of the compound(s) and composition(s) of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50, and usually a larger therapeutic index is more efficacious. While agents that exhibit toxic side effects may be used, care should be taken to design a delivery system that targets such agents to the site of affected tissue in order to minimize potential damage to unaffected cells and, thereby, reduce side effects.

v) Neuroprotection

The following are illustrative of the type of biological assays that can be conducted to assess whether a inhibitory agent has a protective effect against neuronal injury or disease.

a. Morphological Changes

Apoptosis in many cell types is correlated with altered morphological appearances. Examples of such alterations include, but are not limited to, plasma membrane blebbing, cell shape change, loss of substrate adhesion properties. Such changes are readily detectable with a light microscope. Cells undergoing apoptosis can also be detected by fragmentation and disintegration of chromosomes. These changes can be detected using light microscopy and/or DNA or chromatin specific dyes.

b. Altered Membrane Permeability

Often the membranes of cells undergoing apoptosis become increasingly permeable. This change in membrane properties can be readily detected using vital dyes (e.g., propidium iodide and trypan blue). Dyes can be used to detect the presence of necrotic cells. For example, certain methods utilize a green-fluorescent LIVE/DEAD™ Cytotoxicity Kit #2, available from Molecular Probes. The dye specifically reacts with cellular amine groups. In necrotic cells, the entire free amine content is available to react with the dye, thus resulting in intense fluorescent staining. In contrast, only the cell-surface amines of viable cells are available to react with the dye. Hence, the fluorescence intensity for viable cells is reduced significantly relative to necrotic cells (see, e.g., Haugland, 1996 Handbook of Fluorescent Probes and Research Chemicals, 6th ed., Molecular Probes, OR).

c. Dysfunction of Mitochondrial Membrane Potential

Mitochondria provide direct and indirect biochemical regulation of diverse cellular processes as the main energy source in cells of higher organisms. These process include the electron transport chain activity, which drives oxidative phosphorylation to produce metabolic energy in the form of adenosine triphosphate (i.e., ATP). Altered or defective mitochondrial activity can result in mitochondrial collapse called the "permeability transition" or mitochondrial permeability transition. Proper mitochondrial functioning requires maintenance of the membrane potential established across the membrane. Dissipation of the membrane potential prevents ATP synthesis and thus halts or restricts the production of a vital biochemical energy source.

Consequently, a variety of assays designed to assess toxicity and cell death involve monitoring the effect of a test agent on mitochondrial membrane potentials or on the mitochondrial permeability transition. One approach is to utilize fluorescent indicators (see, e.g., Haugland, 1996 Handbook of Fluorescent Probes and Research Chemicals, 6th ed., Molecular Probes, OR, pp. 266-274 and 589-594). Various non-fluorescent probes can also be utilized (see, e.g., Kamo et al. (1979) J. Membrane Biol. 49:105). Mitochondrial membrane potentials can also be determined indirectly from mitochondrial membrane permeability (see, e.g., Quinn (1976) The Molecular Biology of Cell Membranes, University Park Press, Baltimore, Md., pp. 200-217). Further guidance on methods for conducting such assays is provided in PCT publication WO 00/19200 to Dykens et al.

d. Caspase Activation

Apoptosis is the process of programmed cell death and involves the activation of a genetic program when cells are no longer needed or have become seriously damaged. Apoptosis involves a cascade of biochemical events and is under the regulation of a number of different genes. One group of genes act as effectors of apoptosis and are referred to as the interleukin-1β converting enzyme (ICE) family of genes. These genes encode a family of cysteine proteases whose activity is increased in apoptosis. The ICE family of proteases is generically referred to as caspase enzymes. The "C" in the name reflects the fact that the enzymes are cysteine proteases, while "Caspase" refers to the ability of these enzymes to cleave after aspartic acid residues.

Consequently, some assays for apoptosis are based upon the observation that caspases are induced during apoptosis. Induction of these enzymes can be detected by monitoring the cleavage of specifically-recognized substrates for these enzymes. A number of naturally occurring and synthetic protein substrates are known (see, e.g., Ellerby et al. (1997) J. Neurosci. 17:6165; Kluck, et al. (1997) Science 275:1132; Nicholson et al. (1995) Nature 376:37; and Rosen and Casciola-Rosen (1997) J. Cell Biochem. 64:50). Methods for preparing a number of different substrates that can be utilized in these assays are described in U.S. Pat. No. 5,976,822. This patent also describes assays that can be conducted using whole cells that are amendable to certain of the microfluidic devices described herein. Other methods using FRET techniques are discussed in Mahajan, et al. (1999) Chem. Biol. 6:401-9; and Xu, et al. (1998) Nucl. Acids. Res. 26:2034-5.

e. Cytochrome C Release

In healthy cells, the inner mitochondrial membrane is impermeable to macromolecules. Thus, one indicator of cell apoptosis is the release or leakage of cytochrome C from the mitochondria. Detection of cytochrome C can be performed using spectroscopic methods because of the inherent absorption properties of the protein. Thus, one detection option with the present devices is to place the cells within a holding space and monitor absorbance at a characteristic absorption wavelength for cytochrome C. Alternatively, the protein can be detected using standard immunological methods (e.g., ELISA assays) with an antibody that specifically binds to cytochrome C (see, e.g., Liu et al. (1996) Cell 86:147).

f. Assays for Cell Lysis

The final stage of cell death is typically lysis of the cell. When cells die they typically release a mixture of chemicals, including nucleotides, and a variety of other substances (e.g., proteins and carbohydrates) into their surroundings. Some of the substances released include ADP and ATP, as well as the enzyme adenylate cyclase, which catalyzes the conversion of ADP to ATP in the presence of excess ADP. Thus, certain assays involve providing sufficient ADP in the assay medium to drive the equilibrium towards the generation of ATP which can subsequently be detected via a number of different means. One such approach is to utilize a luciferin/luciferase system that is well known to those of ordinary skill in the art in which the enzyme luciferase utilizes ATP and the substrate luciferin to generate a photometrically detectable signal. Further details regarding certain cell lysis assays that can be performed are set forth in PCT publication WO 00/70082.

g. Ischemic Model Systems

Methods for assaying whether a compound can confer protective neurological effects against ischemia and stroke are discussed by Aarts, et al. (Science 298:846-850, 2002). In general, this assay involves subjecting rats to a middle cerebral artery occlusion (MCAO) for a relatively short period of time (e.g., about 90 minutes). MCAO can be induced using various methods, including an intraluminal suture method (see, e.g., Longa, E. Z. et al. (1989) Stroke 20:84; and Belayev, L., et al. (1996) Stroke 27:1616). A composition containing the putative inhibitor is introduced into the rat using conventional methods (e.g., via intravenous injection). To evaluate the compositions prophylactic effect, the composition is administered before performing MCAO. If the compound is to be evaluated for its ability to mitigate against an ischemic event that has already occurred, the composition with the compound is introduced after MCAO has been initiated. The extent of cerebral infarction is then evaluated using various measures of neurological function. Examples of such measures include the postural reflex test (Bederson, J. B. et al. (1986) Stroke 17:472) and the forelimb placing test (De Ryck, M. et al. (1989) Stroke 20:1383). Methods are also described in Aarts et al assessing the effects of NMDA-induced excitotoxicity using in vitro assays.

h. MTT Cytotoxicity Assay

The MTT assay is another assay which has been widely used to assess cytotoxicity in neuronal cells. The cellular toxicity can assessed using the 3-(4,5-dimethylthiazol-2-yl)-2,5-diphenyl tetrazolium bromide (MTT) assay (Trevigen, Gaithersburg, Md.) following the recommendations of the manufacturer.

i. Trypan Blue Cell Viability Measurement

Cell viability can be measured using the trypan blue exclusion method (Yao et al., *Brain Res.*, 889, 181-190 (2001)).

j. Determination of Cellular ATP Levels

Cellular ATP Levels can be indicative of cell viability. Cellular ATP concentrations can be measured using the ATPLite-M® luminescence assay (Packard BioSciences Co.). For example, in this assay, cells typically are cultured on black 96-well ViewPlate® and the ATP concentrations are measured on a TopCount NXT® counter (Packard BioSciences Co.) following the recommendations of the manufacturer.

vi) Gastrointestinal Absorption

The compounds or drugs according to the invention can be further analyzed, tested or validated for their ability to be absorbed by the gut and/or intestine if so desired.

Intestinal permeability and transport of a drug candidate may be estimated using a variety of in vitro, in situ, as well as in vivo models (Balimane et al. (2000) J Pharmacol Toxicol Methods 44:385-401; Hidalgo I. (2001) Curr Top Med Chem 1:385-401, Hillgreen K, Kato A and Borchardt R. (1995) 15:83-109).

For instance, parallel artificial membrane permeability (PAMPA) assay and cell-based systems such as Caco-2 and Mardin-Darby canine kidney (MDCK) cells are the most frequently used in vitro models. The PAMPA model consists of a hydrophobic filter material coated with a mixture of lecithin/phospholipids dissolved in an inert organic solvent creating an artificial lipid membrane barrier that mimics the intestinal epithelium. Caco-2 cells, a human colon adenocarcinoma, undergo spontaneous enterocytic differentiation in culture and become polarized cells with well-established tight junctions, resembling intestinal epithelium in humans. Caco-2 cell model has been the most popular and the most extensively characterized cell-based model in examining the permeability of drugs in both the pharmaceutical industries and academia. Alternatively, MDCK cells which also develop tight junctions and form monolayers of polarized cells are used.

An in situ study such as an intestinal perfusion could also be performed to assess drug absorption. Isolated intestinal segments comprise the absorptive cells and the underlying muscle layers. As it is commonly used, this technique only allows sampling from the mucosal side; drug disappearance is assumed to be equal to drug absorption. Typically, a whole animal absorption study (pharmacokinetic study) will be performed in parallel with the in vitro and/or in situ studies to assess intestinal permeability. In general, drug absorption in animals is believed to be a good predictor of absorption in humans.

vii) Gastrointestinal Toxicity

The compounds or drugs according to the invention can be further analyzed, tested or validated for gastrointestinal (GI) toxicity. Gastrointestinal toxicity of a compound in vivo can be reliably established through the implementation of a standard battery of general toxicological assessments. Generally, regulatory test guidelines from the EU, OECD, ICH, FDA and JMOHW are used as reference material for the preparation of study protocols for such assessments. In North America, the toxicological assessments will generally be carried out in compliance with the United States Food and Drug Administration Title 21 Code of Federal Regulations Part 58, Good Laboratory Practice for Non-clinical studies issued on Dec. 22, 1978, Federal Register plus subsequent amendments.

Within the context of such a non-clinical assessment of the toxicity of a particular compound, GI toxicity may specifically be assessed through the monitoring of body weight gain, the gross examination of materials emitted by the test subject (specifically vomitus and feces) and the monitoring of food/water consumption (appetence). Furthermore, upon termination of a non-clinical toxicological assessment, the retention and processing of GI tract tissues from the test subject(s) to the slide stage, followed by histopathological examination of said tissues by a trained pathologist, is a useful tool, complementary to the aforementioned "in-life" observations.

viii) Crossing of the Blood Brain Barrier (BBB)

The blood-brain barrier (BBB) is a very specialized barrier system of endothelial cells that separates the blood from the underlying brain cells, providing protection to brain cells and preserving brain homeostasis. The brain endothelium has a complex arrangement of tight junctions between the cells that restrict the passage of molecules. Typically the BBB is permeable to small and lipophilic molecules, but larger molecules are generally not transported across unless there is an active transport system available. Thus this is one of the stumbling blocks for drug delivery. An additional problem is the very effective drug efflux systems (P-glycoprotein), which pump the drug back out of cells.

The compounds according to the invention can be further analyzed, tested or validated for their ability to cross the BBB is so desired. Many in-vitro, in-vivo and in-silico methods may be employed during drug development to mimic the BBB (Lohmann et al. (2002) Predicting blood-brain barrier permeability of drugs: evaluation of different in vitro assays. *J Drug Target* 10:263-276; Nicolazzo et al. (2006) Methods to assess drug permeability across the blood-brain barrier. *J Pharm Pharmacol* 58:281-293). In-vitro models include primary endothelial cell culture and immortalized cell lines such as Caco-2, BMEC, MDCK. These cells are useful as a screening method and can appropriately rank compounds in order of BBB permeability. In vivo models such as the internal carotid artery single injection or perfusion, intravenous bolus injection, brain efflux index and intracerebral microdialysis provide more accurate information regarding brain uptake, and these can be complemented with novel imaging techniques (such as magnetic resonance imaging and positron emission tomography), although such methods are not suited to high-throughput permeability assessment.

ix) Brain and CSF Level

The brain and/or cerebrospinal fluid (CSF) levels of the compounds or drugs according to the invention can be assessed, measured or estimated using various models methods, and assays (see Potchoiba M J, and Nocerini, M R (2004) DMD 32:1190-1198; Orlowska-Madjack M. (2004) Acta Neurobiol Exp 64: 177-188; and Hocht, C, Opezza, J A and Taira, C A (2004) Curr Drug Discov Technol 1:269-85)

One of the most common techniques is probably a brain sampling after a whole animal absorption study (pharmacokinetic). For instance, pharmacokinetics (PK) profiles of the compound of the invention could be investigated using typical nonclinical PK studies in mice. Briefly, at different timepoints following intravenous, subcutaneous and oral compound administrations, brain, CSF and plasma samples are collected. The brain, CSF and plasma samples are then analyzed by LC/MS to determine the concentration-time profiles of the compound.

Alternatives such as brain dialysis or distribution of a radiolabelled compound with or without autoradioluminography could also be used. A typical example is a tissue distribution study to assess the time course elimination of radioactivity from tissues following the administration of a known quantity of radiolabeled compound, the percentage of the original dose transported in the brain or CSF can be determined. Furthermore, autoradioluminography of cryosections containing brain tissues with a wide range of radioactivity concentrations can be readily quantified to determine brain levels of a drug.

Alternatively, microdialysis offers a way to remove drugs from the brain. The principle of microdialysis is based on the diffusion of molecules through small-diameter pores of a semi permeable membrane tubing connected to a probe that is implanted into a defined brain area. The probe is connected to a perfusion pump and perfused with a liquid, which equilibrates with the fluid outside the tube by diffusion in both directions. A quantitative analysis of drug in the fraction-collected microdialysates reflects their concentration in the fluid.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference. The invention is further illustrated by the following examples, which should not be construed as further limiting.

EXAMPLES

The Examples set forth herein below provide exemplary syntheses of certain representative compounds of the invention. Also provided are exemplary methods for assaying the compounds of the invention for in vitro stability, microsomes metabolism and mouse bioavailability.

Unless otherwise indicated, all numbers expressing quantities of ingredients, reaction conditions, concentrations, properties, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

The present invention also relates to novel compounds and the synthesis thereof.

The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques. In some cases, the compounds may be commercially available.

Example 1-A

Chemical Synthesis of Amino Acid Prodrugs

Accordingly, the following examples are presented to illustrate how some amino acid prodrugs according to the invention compounds may be prepared.

Preparation of N-hydroxysuccinimide Ester

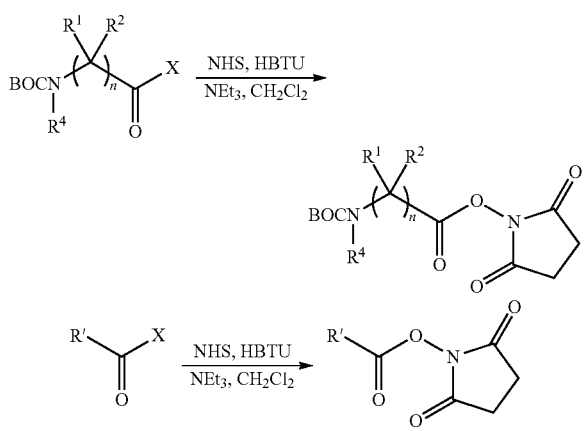

To a stirred solution of a N-Boc-protected amino acid or a carboxylic acid (10 mmol) in $CH_2Cl_2$ (100 mL) was added HBTU (N,N,N',N'-Tetramethyl-O-(1H-benzotriazol-1-yl)uronium hexafluorophosphate, 4.17 g, 11 mmol) followed by addition of triethylamine (1.53 mL, 11 mmol) and N-hydroxysuccinimide (NHS, 1.26 g, 11 mmol). The reaction mixture was stirred at room temperature for 4 h, and then diluted with HCl (1 N) and EtOAc (ethyl acetate). The organic layer was isolated, dried over $Na_2SO_4$, and concentrated. The residual material was purified by flash chromatography on silica gel using hexanes-EtOAc as eluent to afford the corresponding N-hydroxysuccinimide ester in good yield (about 70 to 88%).

General Procedures for the Preparation of Amino Acid Prodrugs of 3-amino-1-propanesulfonic acid (Procedures A to D)

Procedures A to D were used in different combinations, to produce exemplary compounds of the invention. Results for the preparation of Compounds A to Y using these procedures are summarized in Table 2 below.

Procedure A

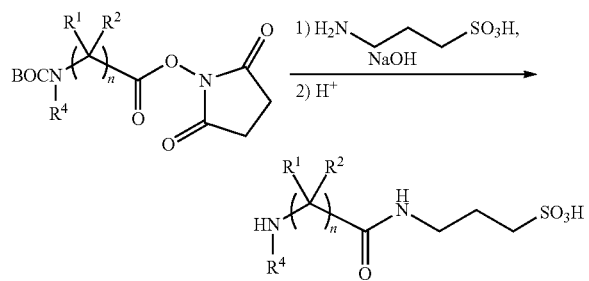

A solution of the N-hydroxysuccinimide ester of a N-Boc-protected amino acid or a carboxylic acid (48 mmol, 1.2 eq) in acetonitrile or acetone (50 mL) was added slowly to a solution of 3APS, 3-amino-1-propanesulfonic acid, 40 mmol, 1 eq in 2 N NaOH (sodium hydroxide, 23 mL, 1.2 eq). The reaction mixture was stirred at room temperature overnight. The mixture was evaporated to dryness. The residual material was stirred with Et$_2$O (diethyl ether, 150 mL) at reflux for 1 h. After the mixture was cooled to room temperature, the solid material was filtered and dried in vacuo, and further purified according to one of the following work-up procedures:

(i) The solid material was dissolved in water (25 mL). The solution was passed through a Dowex™ Marathon™ C ion-exchange column (strongly acidic, 110 g (5 eq), prewashed). The strong acidic fractions were combined and treated with concentrated HCl (10 mL). The mixture was stirred at 50° C. for 30 minutes, and then was concentrated to dryness. The residual material was co-evaporated with EtOH (ethanol) to completely remove water. EtOH (100 mL) was added to the residue. The mixture was stirred at reflux for 1 h, and then cooled to room temperature. The solid material was collected by filtration. The solid material was dissolved in water (10 mL). The solution was added drop wise to EtOH (100 mL). The product slowly crystallized. The suspension was stirred at room temperature for 30 minutes. The solid material was collected by filtration and it was dried in a vacuum oven (60° C.).

(ii) The solid material was dissolved in water (25 mL). The solution was passed through a Dowex™ Marathon™ C ion exchange column (strongly acidic, 110 g (5 eq), prewashed). The strong acidic fractions were combined and evaporated under reduced pressure. The residue was purified using reverse-phase flash chromatography (Biotage™ SP-1, C18 column). For ester-containing compound, the final product was obtained after removal of the solvent from the corresponding fractions; otherwise go to (iii).

(iii) The residual material from step (ii) above was stirred with 4N HCl (3 mL) at 50° C. for 1 h. A white solid precipitate appeared. After the mixture was cooled to room temperature, the solid material was collected by filtration, washed, and dried in vacuo, to provide the final product.

Procedure B

To a stirred solution of a N-hydroxysuccinimide ester (3 mmol) in a mixture of H$_2$O/tetrahydrofuran/CH$_3$CN (10/10/10 mL) was added a solution of 3APS (as sodium salt) (3.3 mmol) in water (5 mL) followed by addition of 1M solution of potassium carbonate (3 mL). The reaction mixture was stirred for 2 h, followed by addition of EtOAc. The aqueous layer was isolated and concentrated to a residue. The residual material was purified by silica gel column using CH$_2$Cl$_2$-MeOH (80-20) as eluent to give the corresponding N-Boc-protected product. The purified N-Boc-protected product was dissolved in dichloromethane (CH$_2$Cl$_2$, 10 mL) followed by addition of TFA (trifluoroacetic acid, 5 mL). The reaction mixture was stirred for 2 h, and then concentrated under reduced pressure. The residual solid material was suspended in a minimum amount of ethanol and the mixture was stirred for 1 h under reflux. The mixture was cooled to room temperature. The solid material was collected by filtration, washed with ethanol, and dried under high vacuum to afford the final compound.

Procedure C

To the purified product containing benzyl ether protection group from procedure A or B (3.5 mmol) in 2N HCl (500 mL) and MeOH (500 mL) was added 10% Pd/C (2.15 g). The mixture was stirred under hydrogen (1 atm) overnight. The suspension was filtered (Celite™. The filter cake was washed with water (2×25 mL). The filtrate and the washing were combined and evaporated under reduced pressure. The residual material was purified by reverse-phase HPLC(C18 column, 0-15% acetonitrile/water). The fractions containing the desired compound were combined and lyophilized, to give the final product.

Procedure D

This procedure is used to produce prodrugs of Formulae I to VI having more than one amino acid coupled to 3APS. Step (i) or (ii) is repeated as necessary to obtain the desired compound.

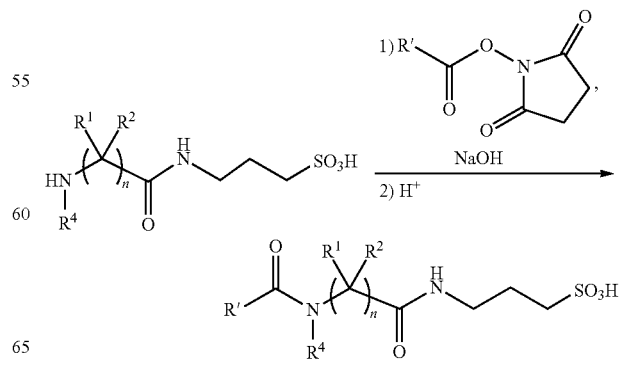

(i) The product from Procedures A, B, or C is further reacted with another N-hydroxysuccinimide ester following Procedure A(i).

(ii) The product from Procedures A, B, or C was further reacted with another N-hydroxysuccinimide ester following Procedure B.

TABLE 5

Synthesis and characterization of exemplary amino acid prodrugs according to the invention

| ID | Synthetic Procedure | NMR (ppm; 1H 500 MHz; 13C 125 MHz) MS (electrospray ionization) |
|---|---|---|
| A1 | A(i) | 1H NMR (D2O) δ 1.55-1.61 (m, 2H), 2.40-2.48 (m, 2H), 2.92-3.01 (m, 2H), 3.04-3.14 (m, 2H), 3.95-3.98 (m, 1H), 7.11 (d, J = 6.8 Hz, 2H), 7.19.7.27 (m, 3H); 13C NMR (D2O) δ 23.76, 37.02, 38.21, 48.36, 54.79, 128.19, 129.33, 129.42, 134.01, 168.94; m/z 285 (M-1). |
| A2 | A(i) | 1H NMR (D2O) δ 0.87-0.90 (m, 6H), 1.83 (qt, J = 7.2 Hz, 2H), 2.02-2.09 (m, 1H), 2.79 (t, J = 7.8 Hz, 2H), 3.20-3.29 (m, 2H), 3.60 (d, J = 6.3 Hz, 2H); 13C NMR (D2O) δ 17.20, 17.77, 24.11, 30.00, 38.29, 48.63, 58.96, 169.35; m/z 237 (M-1). |
| A3 | A(i) | 1H NMR (D2O) δ 1.82 (qt, J = 7.2 Hz, 2H), 1.90-1.95 (m, 3H), 2.28-2.33 (m, 1H), 2.78 (t, J = 7.8 Hz, 2H), 3.22-3.33 (m, 4H), 4.21 (t, J = 7.1 Hz, 2H); 13C NMR (D2O) δ 23.95, 24.07, 29.85, 38.49, 46.57, 48.53, 60.00, 169.64; m/z 235 (M-1). |
| A4 | A(ii) | 1H NMR (D2O) δ 1.30 (qt, J = 8.1 Hz, 2H), 1.57 (qt, J = 7.8 Hz, 2H), 1.75-1.85 (m, 4H), 2.77-280 (m, 2H), 2.87 (t, J = 7.8 Hz, 2H), 3.17 (qt, J = 6.7 Hz, 1H), 3.31 (qt, J = 6.8 Hz, 1H), 3.83 (t, J = 6.6 Hz, 1H); 13C NMR (D2O) δ 21.47, 24.12, 30.49, 38.30, 39.18, 48.63, 53.28, 169.66; m/z 266 (M-1). |
| A5 | B | 1H NMR (DMSO-d6) δ 0.81 (d, J = 7.3 Hz, 3H), 7.84 (d, J = 7.3 Hz, 3H), 1.5 (m, 1H), 1.60 (m, 2H), 1.82 (m, 2H), 2.80 (m, 2H), 3.20-3.30 (m, 2H), 3.82 (t, J = 7.3 Hz, 1H); 13C NMR (DMSO-d6) δ 21.48, 21.78, 24.17, 38.42, 40.08, 48.66, 52.35, 170.53; m/z 251 (M-1). |
| A6 | A(i) | 1H NMR (D2O) δ 1.84 (m, 2H), 1.99 (s, 3H), 2.04 (m, 2H), 2.47 (m, 2H), 2.80 (m, 2H), 3.24 (t, J = 6.6 Hz, 2H), 3.94 (t, J = 6.6 Hz, 2H); 13C NMR (D2O) δ 14.18, 24.07, 28.44, 30.09, 38.41, 48.61, 52.66, 169.46; m/z 269 (M-1). |
| A7 | B and C | 1H NMR (D2O) δ 1.81 (m, 2H), 2.80 (m, 2H), 3.23 (m, 2H), 3.80 (m, 2H), 3.97 (t, J = 5.0 Hz, 1H); 13C NMR (D2O) δ 24.10, 38.39, 48.55, 54.85, 60.44, 167.97; m/z 225 (M-1). |
| A8 | A(i) | 1H NMR (D2O) δ 3.90 (q, 1H, J = 7 Hz), 3.23 (t, 2H, J = 7 Hz), 2.78 (m, 2H), 1.82 (m, 2H), 1.38 (d, 3H, J = 7 Hz); 13C NMR (D2O) δ 170.90, 49.30, 48.55, 38.28, 24.10, 16.65; m/z 209 (M-1). |
| A9 | A(i) | 1H NMR (D2O) δ 3.90 (q, 1H, J = 7 Hz), 3.23 (t, 2H, J = 7 Hz), 2.78 (m, 2H), 1.82 (m, 2H), 1.38 (d, 3H, J = 7 Hz); 13C NMR (D2O) δ 170.90, 49.30, 48.55, 38.28, 24.10, 16.65; m/z 209 (M-1). |
| A10 | B | 1H NMR (D2O) δ 1.82 (m, 2H), 2.80 (m, 2H), 3.25 (m, 2H), 3.67 (s, 2H); 13C NMR (D2O) δ 24.13, 38.26, 40.57, 48.55, 167.08; m/z 195 (M-1). |
| A11 | A(i) | 1H NMR (D2O) δ 0.80 (t, 3H, J = 7.3 Hz), 0.86 (d, 3H, J = 6.8 Hz), 1.12 (m, 1H), 1.40 (m, 1H), 1.83 (m, 3H), 2.79 (m, 2H), 3.25 (m, 2H), 3.68 (d, 1H, J = 5.9 Hz); 13C NMR (D2O) δ 10.59, 14.22, 24.11, 24.37, 36.38, 38.29, 48.64, 58.00, 169.35; m/z 251 (M-1). |
| A12 | A(i) | 1H NMR (D2O) δ 1.84 (m, 2H), 1.99 (s, 3H), 2.04 (m, 2H), 2.47 (m, 2H), 2.80 (m, 2H), 3.25 (t, J = 7.3 Hz, 2H), 3.94 (t, J = 6.6 Hz, 1H); 13C NMR (D2O) δ 14.18, 24.06, 28.42, 30.07, 38.41, 48.60, 52.66, 169.42; m/z 269 (M-1). |
| A13 | A(i) | 1H NMR (D2O) δ 1.70 (m, 2H), 2.64 (m, 2H), 3.15 (m, 1H), 3.22 (m, 3H), 4.06 (t, J = 6.3 Hz, 1H), 7.30 (s, 1H), 8.55 (d, J = 1.5 Hz, 1H); 13C NMR (D2O) δ 23.94, 26.27, 38.36, 48.43, 52.59, 118.40, 126.36, 134.60, 167.96; m/z 275 (M-1). |
| A14 | A(i) | 1H NMR (D2O) δ 1.46 (s, 6H), 1.83 (m, 2H), 2.77 (m, 2H), 3.23 (t, J = 6.6 Hz, 2H); 13C NMR (D2O) δ 23.44, 24.08, 38.54, 48.61, 57.21, 173.20; m/z 223 (M-1). |
| A15 | A(i) | 1H NMR (D2O) δ 1.74 (m, 2H), 2.59 (m, 2H), 3.15 (m, 1H), 3.23 (m, 1H), 4.95 (s, 1H), 7.38 (m, 5H); 13C NMR (D2O) δ 24.00, 38.35, 48.38, 56.84, 128.05, 129.87, 130.52, 132.46, 168.90; m/z 271 (M-1). |
| A16 | A(i) | 1H NMR (D2O) δ 1.49 (m, 2H), 2.34 (m, 2H), 2.98 (m, 2H), 3.21 (m, 2H), 4.01 (m, 1H), 7.05 (t, 1H, J = 7.3 Hz), 7.14 (m, 2H), 7.39 (d, 1H, J = 8.3 Hz), 7.47 (m, 1H); 13C NMR (D2O) δ 23.60, 27.14, 38.32, 48.16, 54.12, 106.83, 112.32, 118.23, 119.70, 122.35, 125.18, 126.63, 136.37, 139.57; m/z 324 (M-1). |
| A17 | A(iii) and then C | 1H NMR (D2O) δ 1.66 (m, 2H), 2.58 (m, 2H), 2.92 (m, 1H), 3.04 (m, 2H), 3.17 (m, 1H), 3.95 (t, 1H, J = 6.3 Hz), 6.77 (d, 2H, J 8.8 Hz), 7.02 (d, 2H, J = 8.3 Hz); 13C NMR (D2O) δ 23.91, 36.29, 38.25, 48.42, 54.95, 116.07, 125.88, 130.91, 155.29, 169.56; m/z 301 (M-1). |
| A18 | B | 1H NMR (D2O) δ 1.77 (m, 2H), 2.74 (m, 2H), 3.19 (, m2H), 3.75 (m, 2H), 4.05 (m, 1H), 4.42 & 4.65 (AB, J = 12.2 Hz, 2H), 7.26-7.33 (m, 5H); 13C NMR (D2O) δ 24.10, 38.43, 53.23, 67.39, 73.28, 128.63, 128.67, 128.96, 136.86, 167.55; m/z 315 (M-1). |
| A19 | A(ii) | 1H NMR (D2O) δ 7.3-7.2 (m, 5H), 5.05 (s, 2H), 3.83 (t, J = 6.7 Hz, 1H), 3.21 (qn, J = 7 Hz, 1H), 3.08 (qn, J = 7 Hz, 1H), 2.78 (t, J = 7.8 Hz, 2H), 2.45 (t, J = 7 Hz, 2H), 2.05 (q, J = 7 Hz, 2H), 1.78 (m, 2H); m/z 357 (M-1). |
| A20 | B | 1H NMR (D2O) δ 1.78-1.85 (m, 4H), 2.24 (t, J = 7.5 Hz, 2H), 2.79 (m, 2H), 2.88 (t, J = 7.8 Hz, 2H), 3.18 (t, J = 7.0 Hz, 2H). 13C NMR (D2O) δ 23.21, 24.16, 32.70, 38.16, 38.98, 48.65, 175.06; m/z 223 (M-1). |
| A22 | | 1H NMR (D2O) δ 1.84 (qn, 2H, J = 7 Hz), 2.78 (dd, 2H, J = 8.0, 6 Hz), 2.85 (ABX, 2H, J = 5.5, 7.3, 16.8 Hz), 3.24 (m, 2H), 3.61 (dd, 1H, J = 5.5, 7.3 Hz); 13C NMR (D2O) δ 24.05, 35.42, 38.46, 48.53, 50.04, 169, 171. |
| A28 | | 1H NMR (D2O) δ 0.8-0.9 (m, 12H), 1.81 (m, 1H), 1.88 (m, 1H), 2.09 (m, 2H), 2.77 (t, 2H, J = 8.0 Hz), 3.20 (t, 2H, J = 6.6 Hz), 3.73 (d, 1H, J = 6.1 Hz), 3.87 (d, 1H, J = 8.9 Hz); 13C NMR (D2O) δ 16.93, 17.82, 18.36, 24.21, 29.77, 30.27, 38.08, 48.72, 58.42, 60.66, 169.45, 173.07 |

Example 1-B

Chemical Synthesis of Carbamate Prodrugs

Accordingly, the following examples are presented to illustrate how some carbamate prodrugs according to the invention compounds may be prepared.

General Synthetic Procedures

Procedure A

Preparation of Compound C1 sodium salt (3-(p-acetyloxybenzyloxycarbonyl)amino-1-propanesulfonic acid sodium salt)

Step 3: The carbonate prepared in the step 2 (2.2 g, 6.7 mmol, 2 eq.) was added to a mixture of 3-amino-1-propanesulfonic acid sodium salt (538 mg, 3.32 mmol) and triethylamine (0.90 ml, 6.7 mmol, 2 eq.) in dry N,N-dimethylformamide (DMF, 10 mL). The reaction mixture was stirred at room temperature overnight. Solvent was removed by evaporation. The residue was partitioned between EtOAc and water. The aqueous phase was washed twice with EtOAc, and then lyophilized. HPLC purification (acetonitrile/water, 20/80 to 90/10) of the lyophilized residue provided the title compound (396 mg, 33%): $^1$H NMR (500 MHz, D$_2$O) δ ppm 1.83-1.89 (m, 2H), 1.98 (s, 3H), 2.84-2.87 (m, 2H), 3.19-3.21 (m, 2H), 5.01 (s, 2H), 7.03 (d, J=8.8 Hz, 2H), 7.32 (d, J=8.3 Hz, 2H). 87

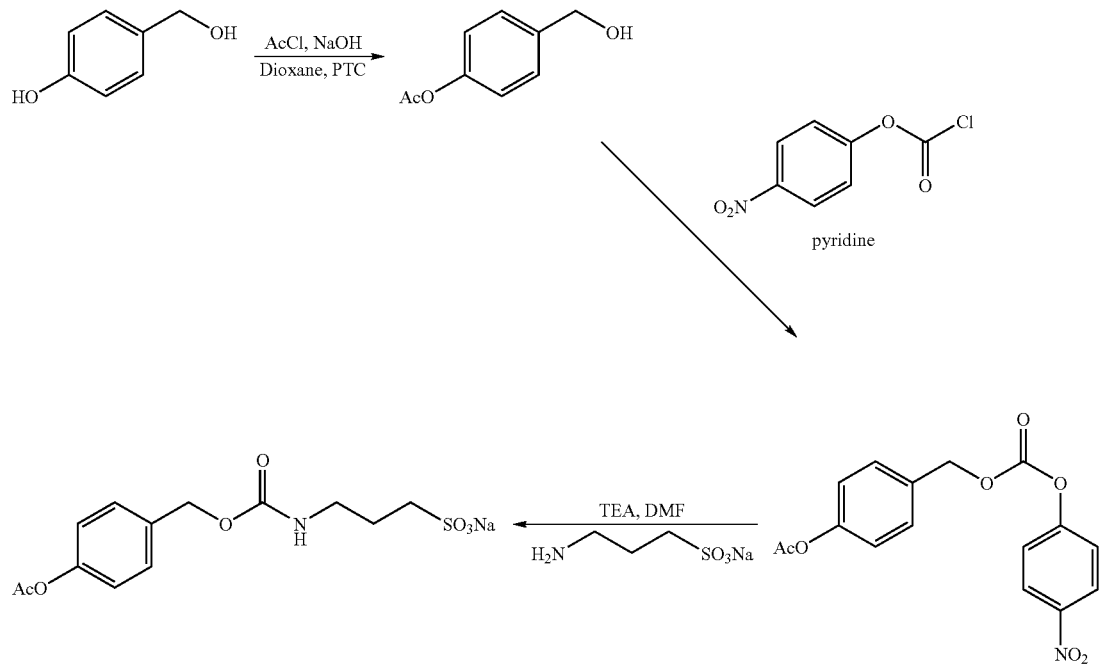

Step 1: Acetyl chloride (3.0 mL, 42 mmol, 1 eq.) was added to a mixture of 4-hydroxybenzylalcohol (5.3 g, 42 mmol), sodium hydroxide (1.7 g, 42 mmol, 1 eq.) and tetrabutylammonium hydrogen sulfate (7 g, 0.5 eq.) in dioxane (100 mL). The reaction mixture was stirred at room temperature for 4 hours and the solvent was evaporated. The residue was dissolved in water and the aqueous phase was extracted with EtOAc (3 times). Combined organic extracts were washed with brine, dried and concentrated to give colorless oil. Purification (flash chromatography; hexane/EtOAc, gradient mode) provided the corresponding monoacetate (2.2 g, 32%).

Step 2: Anhydrous pyridine (1.1 mL, 13 mmol, 1 eq) was added drop wise to a stirred mixture of p-nitrophenyl chloroformate (4.0 g, 20 mmol, 1.5 eq.) and the monoacetate (from step 1: 2.2 g, 13 mmol) in dry tetrahydrofuran (THF, 25 mL). A white precipitate was formed. The reaction mixture was stirred at room temperature for 1 hour. The solid material was removed by filtration, and washed with THF. The filtrate and the washing were combined; and the solvent was removed in vacuo. The residual material was purified by flash chromatography (hexanes/EtOAc, 80/20) to provide the corresponding carbonate (2.8 g, 62%).

Procedure B

Preparation of Compound C6 sodium salt (4-aza-7-methyl-15-phenyl-11,11-tetramethylene-6,8,14-trioxa-5,9,13-trioxo-1-pentadecanesulfonic acid sodium salt)

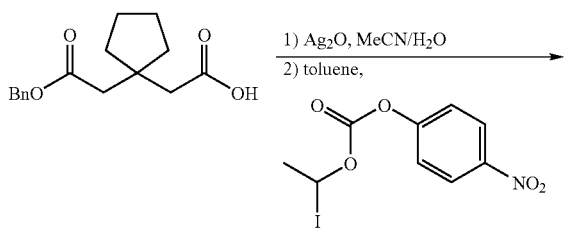

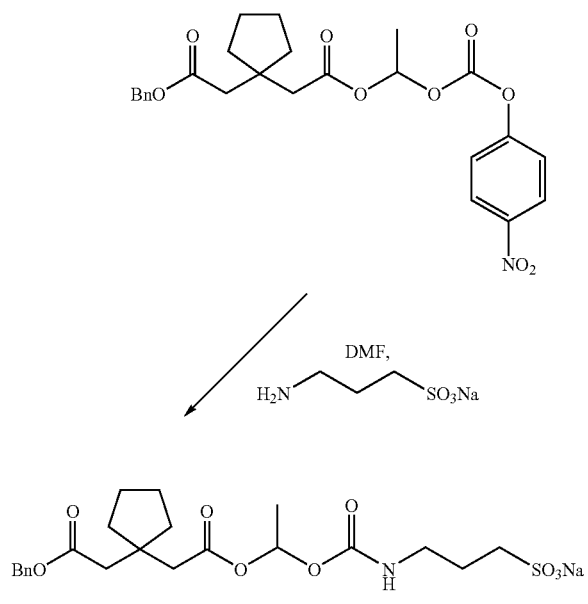

Step 1: 3,3-Tetramethyleneglutaric acid monobenzyl ester (4.26 g; 15.4 mmol, prepared by heating overnight the cyclic anhydride and benzyl alcohol in dioxane at 80° C. in the presence of triethylamine) and silver oxide (2.13 g; 9.22 mmol) were added to a mixture of acetonitrile (40 mL) and water (20 mL). The mixture was heated at 70° C. for 3 h, and then cooled to room temperature. The mixture was filtered through a pad of Celite™. The filtrate was evaporated to provide the crude silver carboxylate (2.19 g, 37%) which was used in the next step without further purification.

Step 2: A mixture of the silver carboxylate (2.19 g, 5.71 mmol; from step 1) and the carbamating reagent (1.00 g; 2.95 mmol; for preparation, see in Procedure E), in dry toluene (100 mL) was heated at 50° C. overnight. The mixture was filtered through a pad of Celite™ and the filtrate was evaporated to provide a solid residue, which was purified by flash chromatography using hexane/EtOAc (80/20), giving the desired intermediate product (0.915 g, 64%).

Step 3: To a solution of the intermediate product from step 2 (0.915 g; 1.88 mmol) in dry DMF (5 mL) was added 3-amino-1-propanesulfonic acid sodium salt (300 mg; 1.85 mmol). The mixture was stirred at room temperature overnight. Solvent was removed by evaporation. The residual material was purified by Prep-HPLC to furnish, after lyophilization, the title compound (632 mg, 66%): $^1$H NMR (CD$_3$OD, 500 MHz) δ 1.39 (d, J=5.9 Hz, 3H), 1.64-1.59 (m, 8 H), 1.97-1.91 (m, 2H), 2.49 (qAB, J=15.1 Hz, 2H), 2.57 (qAB, J=15.1 Hz, 2H), 2.82-2.79 (m, 2H), 5.10 (s, 2H), 3.26-3.14 (m, 2H), 6.74 (q, J=5.9 Hz, 1H), 7.38-7.29 (m, 5H). 88

Other compounds prepared according to this procedure (Procedure B) were purified either by precipitation using methanol and ether (protocol (b)), or by preparative HPLC using acetonitrile/water (10/90 to 90/10) over 40 minutes at 50 mL/min (protocol (a)), or by normal phase flash chromatography (protocol (c)).

Procedure C

Preparation of Compound C2 sodium salt (4-aza-12-carboxy-6,8-dioxa-5,9-dioxo-7-methyl-11,11-tetramethylene-1-dodecanesulfonic acid sodium salt)

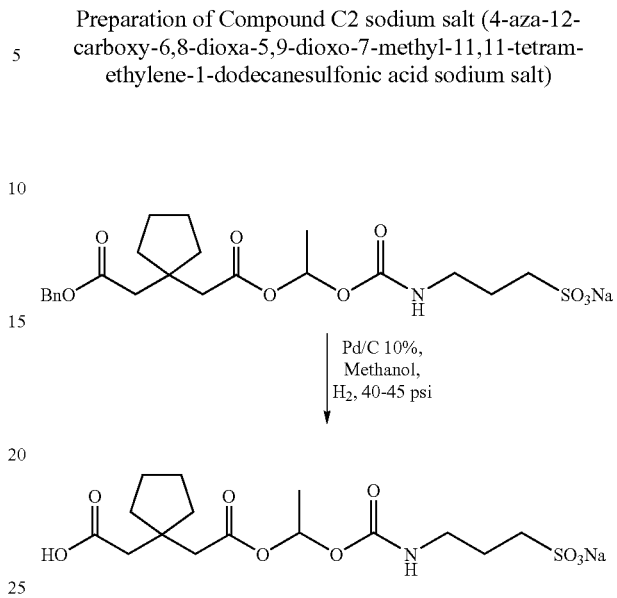

The corresponding benzylester of the title compound (344 mg; 0.678 mmol) in methanol (5 mL) was hydrogenolyzed in the presence of Pd/C 10% (100 mg) at 40-45 psi for 1 h. The mixture was filtered (Celite™ and the filtrate was evaporated to dryness. The residual material was dissolved in water and the aqueous solution was lyophilized, giving the title compound (242 mg, 86%): $^1$H NMR (CD$_3$OD, 500 MHz) δ 1.43 (d, J=5.4 Hz, 3H), 1.66-1.63 (m, 8H), 1.98-1.92 (m, 2H), 2.49 (qAB, J=15.6 Hz, 2H), 2.55 (qAB, J=15.1 Hz, 2H), 2.83-2.80 (m, 2H), 3.24-3.21 (m, 2H), 6.77 (q, J=5.4 Hz, 1H), 7.22 (t, J=5.4, N-H).

Procedure D

Preparation of Compound C19 sodium salt (4-aza-7-methyl-6,8-dioxa-5,9-dioxo-1-decanesulfonic acid sodium salt)

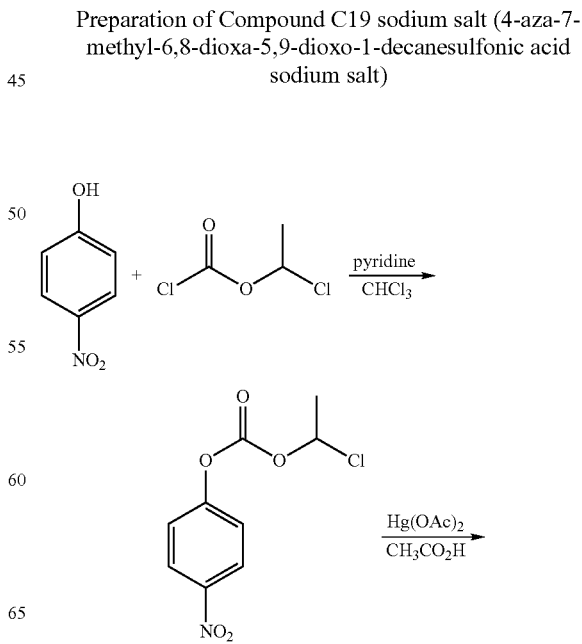

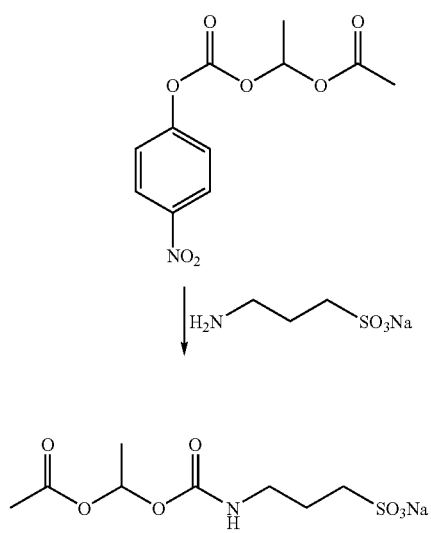

Step 1: 1-Chloroethylchloroformate (7.8 ml, 72 mmol, 1 eq.) was added to an ice-cold solution of p-nitrophenol (10 g, 72 mmol) in chloroform (100 mL), followed by drop wise addition of pyridine (8.8 ml, 108 mmol, 1.5 eq.) over a period of 20 min. The mixture was stirred in the ice-cold bath for 15 min, and then at room temperature overnight. The reaction mixture was sequentially washed with water, 1 N hydrochloric acid, water, 1 N sodium hydroxide, water, and brine. The organic phase was dried over $Na_2SO_4$, and concentrated to give yellow oil which, upon standing, crystallized to afford the corresponding chloroethyl carbonate (15.5 g, 88%).

Step 2: To a solution of the chloroethyl carbonate obtained from step 1 (6.2 g, 25 mmol) in acetic acid (150 mL) was added mercuric acetate (9.6 g, 30 mmol, 1.2 eq.). The mixture was stirred at room temperature overnight. Solvent was evaporated. The residual material was transferred into ether and washed with a saturated aqueous solution of $NaHCO_3$. The ether layer was dried over $MgSO_4$ and concentrated to give thick yellow oil. Purification of the oil by flash chromatography (hexane/EtOAc, 95/5) gave the corresponding acetyloxyethyl carbonate (6.3 g, 94%) as colorless oil.

Step 3: The acetyloxyethyl carbonate obtained from step 2 (1.2 g, 4.3 mmol, 1.1 eq.) was added to a solution of 3-amino-1-propanesulfonic acid sodium salt (0.63 g, 3.9 mmol) in DMF (10 mL). The yellow solution was stirred at room temperature overnight (color disappeared at this point). Solvent was evaporated. The residue was triturated several times with ether and turned to a solid. The solid material was collected by filtration to give the title compound (840 mg, 74%): $^1H$ NMR (500 MHz, $CD_3OD$) δ 1.42 (d, J=5.4 Hz, 3H), 1.92-1.98 (m, 2H), 2.02 (s, 3H), 2.80-2.83 (m, 2H), 3.20-3.24 (m, 2H), 6.73 (q, J=5.4 Hz, 1H)

Other compounds prepared according to this procedure (Procedure D) were purified either by extraction from EtOAc/water followed by lyophilization of the aqueous phase, or reverse-phase HPLC purification using acetonitrile/water (10/90 to 90/10) in 40 minutes at 50 mL/min, or trituration/precipitation with ether.

Procedure E

Preparation of Compound C16 sodium salt (4-aza-7-methyl-6,8-dioxa-5,9-dioxo-9-phenyl-1-nonane-sulfonic acid sodium salt)

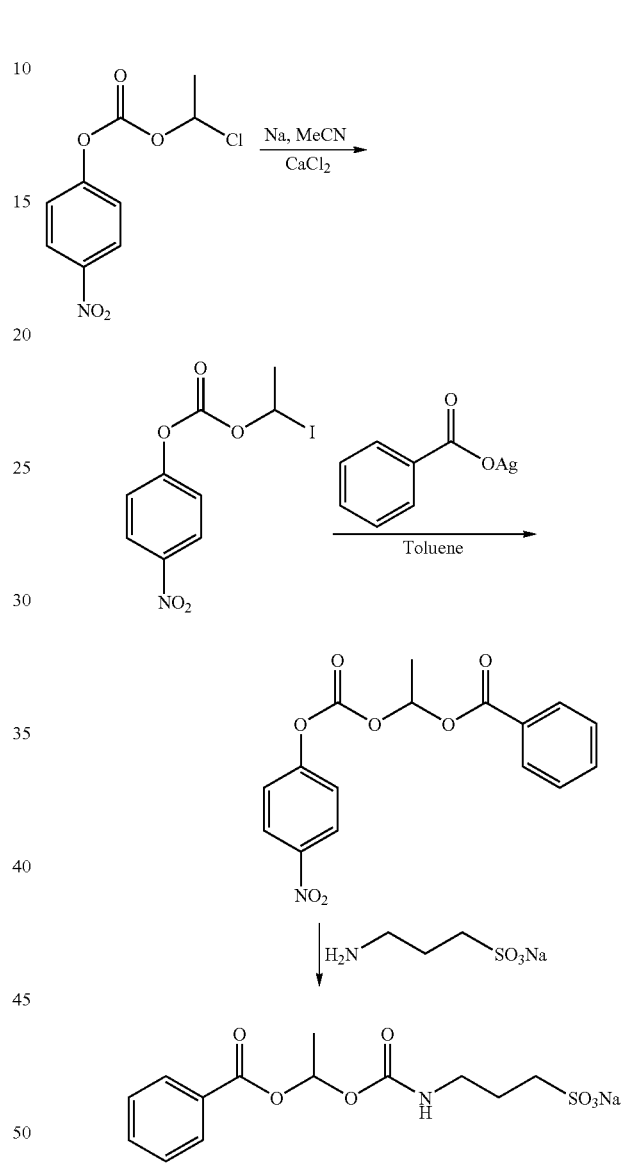

Step 1: Sodium iodide (14 g, 92 mmol, 3 eq.) was added to a mixture of the chloroethyl carbonate (7.5 g, 31 mmol; for preparation, see in Procedure D), and grinded calcium chloride (10 g, 92 mmol, 3 eq.) in acetonitrile (100 mL). The reaction mixture was stirred at 40 LC for 4 days, followed by filtration through a Celite™ pad. The filtrate was concentrated to give a red gummy residue. Purification by flash chromatography using EtOAc/hexane in a gradient mode provided the corresponding iodoethyl carbonate (6 g, 59%) as pale yellow oil.

Step 2: Silver benzoate (5.5 g, 24 mmol, 2 eq.) was added to a solution of the above-obtained iodoethyl carbonate (4 g, 12 mmol) in toluene (50 mL). The reaction mixture was stirred at 55 LC overnight. The reaction mixture was filtered through a Celite™ pad and washed with toluene. The filtrate was concentrated to give brown oil. Two repeated purifications by flash chromatography using hexane/EtOAc (90/10) provided the corresponding benzoate (0.98 g, 25%) in high purity.

Step 3: The above-obtained benzoate (0.98 g, 2.9 mmol, 1.1 eq., from step 2) was added to a solution of 3-amino-1-propanesulfonic acid sodium salt (0.43 g, 2.7 mmol) in DMF (10 mL). The yellow solution was stirred at room temperature overnight. Solvent was evaporated and the residue was dissolved in water. The aqueous solution was extracted several times with EtOAc. The aqueous phase was lyophilized to give a residue, which was purified by preparative HPLC (acetonitrile/water; 10/90 to 90/10, in 40 minutes at 50 mL/min), giving the title compound (256 mg): $^1$H NMR (500 MHz, $D_2O$) δ1.48 (d, J=5.4 Hz, 3H), 1.76-1.82 (m, 2H), 2.76-2.79 (m, 2H), 3.08-3.14 (m, 2H), 6.83 (q, J=5.4 Hz, 1H), 7.39-7.42 (m, 2H), 7.55-7.58 (m, 1H), 7.89-7.91 (m, 2H).

Procedure F

Preparation of Compound C26 sodium salt (3-({[(5-methyl-2-oxo-1,3-dioxol-4-yl)methoxy]carbonyl}amino)-1-propanesulfonic acid sodium salt)

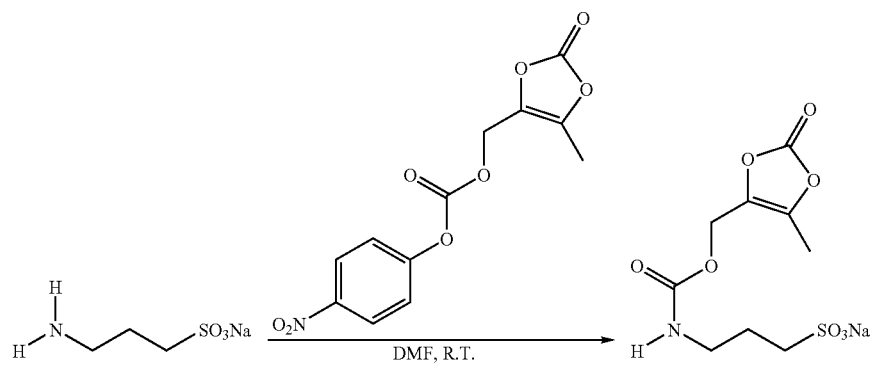

A mixture of the sodium salt of 3-amino-1-propanesulfonic acid (532 mg; 3.30 mmol) and the carbonate (1.10 g; 3.73 mmol; ref., *J. Med. Chem.*, 1996, 39, 480-486) in dry DMF (10 mL) was stirred at room temperature overnight. Solvent was removed in vacuo. To the residual material was added methanol (10 mL), followed by the addition of ether (75 mL). The solid formed was collected by filtration and dried overnight. Again the solid was dissolved in methanol (10 mL) and precipitated with ether (50 mL). The solid material was purified by preparative HPLC to provide the title compound (260 mg, 25%) as a white lyophilized solid: $^1$H NMR (CD$_3$OD, 500 MHz) δ 1.98-1.92 (m, 2H), 2.17 (s, 3H), 2.90-2.79 m, 2H), 3.22 (t, J=6.8 Hz, 2H), 4.86 (s, 2H).

TABLE 6

Synthesis and characterization of exemplary carbamate prodrugs according to the invention

| ID | Synthetic procedure | Purifying protocol* | m/z (ES$^-$) (M − H, or M − Na)$^†$ |
|---|---|---|---|
| C1 | A | (a) | 330.0 |
| C2 | C | (d) | 394.0 |
| C3 | B, C | (a) | 408.5 |
| C4 | C | (d) | 326.1 |
| C5 | B | (a) | 416.0 |
| C6 | B | (a) | 484.0 |
| C7 | B | (a) | 458.3 |
| C8 | C | (d) | 368.5 |
| C9 | C | (d) | 354.0 |
| C10 | B | (a) | 444.1 |
| C11 | C | (d) | 340.1 |
| C12 | B | (b) and (a) | 430.2 |
| C13 | B | (b) and (a) | 378.0 |
| C14 | B | (b) and (a) | 372.0 |
| C15 | D | (a) | 310.2 |
| C16 | E | (a) | 330.2 |
| C17 | D | (a) | 336.2 |
| C18 | D | (b) | 296.2 |
| C19 | D | (b) | 268.1 |
| C20 | D | (a) | 378.1 |
| C21 | D | (a) | 310.1 |
| C22 | D | (a) | 296.1 |
| C23 | D | (a) | 338.1 |
| C24 | D | (a) | 310.0 |
| C25 | E | (b) | 253.9 |
| C26 | F | (b) and (a) | 294.0 |

*(a), HPLC; (b), precipitation; (c), flash chromatography; (d), filtration; (e), extraction,
$^†$the compounds were synthesized as acid form, or as sodium salt form.

Example 1-C

Chemical Synthesis of Non-Amino Acid Amide Prodrugs

Accordingly, the following examples are presented to illustrate how some non-amino acid amide prodrugs according to the invention compounds may be prepared.

Procedure A

Preparation of Compound B3 sodium salt (3,3-dimethyl-5-oxo-5-[(3-sulfopropyl)amino]pentanoic acid sodium salt)

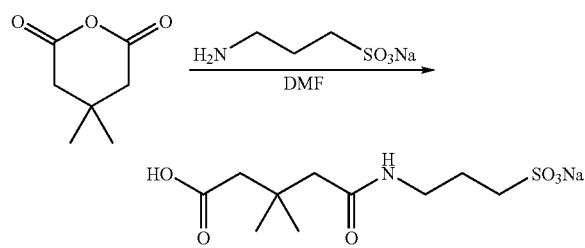

A mixture of the 3,3-dimethylglutaric anhydride (1.0 g; 7.0 mmol) and 3-amino-1-propanesulfonic acid sodium salt (0.950 g; 5.86 mmol) in dry DMF (20 mL) was stirred at 50° C. for 2 days. Solvent was evaporated. To the residual material was added methanol (~10 mL) followed by the addition of ether (~50 mL) to cause precipitation. The precipitate formed was collected by filtration and then dissolved in water and lyophilized to provide the title compounds (1.33 g, 75%) as a powder: $^1$H NMR ($D_2O$, 500 MHz) δ 0.94 (s, 6H), 1.82-1.77 (m, 2H), 2.14 (s, 3H), 2.23 (s, 3H), 2.79-2.76 (m, 2H), 3.16 (t, J=6.8 Hz, 2H).

Other compounds prepared in the above procedure (Procedure A, see Table 7) were purified either by methanol-ether precipitation (Purification protocol (b)), or using preparative HPLC (Purification protocol (a)), or by normal-phase flash-chromatography (Purification protocol (c)). Reaction time for Compounds B1 and B2 was 4 days; and for all other compounds, 2 days.

Procedure B

Preparation of Compound B7 (3-[3-(2-Hydroxy-((S)-valyl ester)-4,6-dimethyl-phenyl)-3-methyl-butyrylamino]-1-propanesulfonic acid)

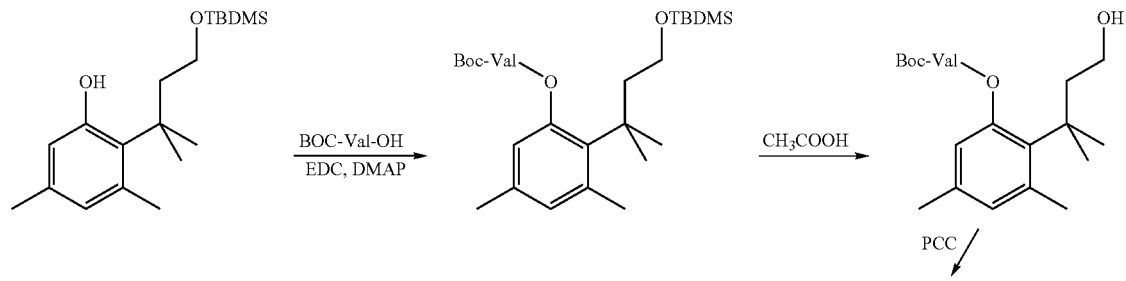

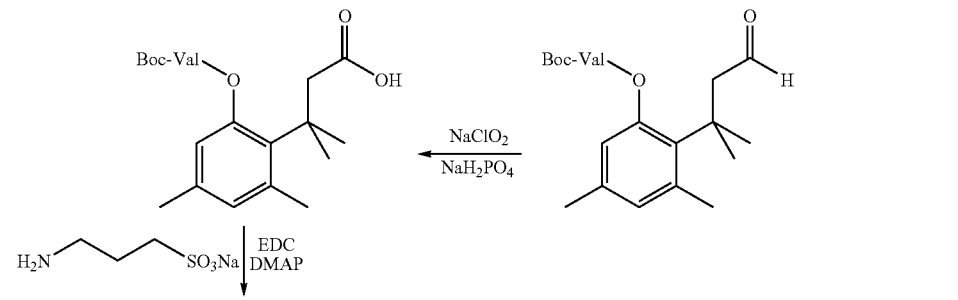

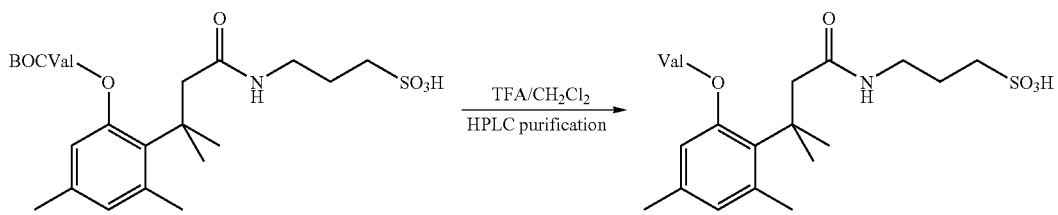

Step 1: EDC(N-(3-dimethylaminopropyl)-N-ethylcarbodiimide) (6.4 g, 33 mmol, 3 eq.) was added, at 0° C., to a 150-mL dry dichloromethane solution containing Boc-Val-OH (4.9 g, 22 mmol, 2 eq.), the silylated phenol (3.6 g, 11 mmol; ref., *J. Med. Chem.*, 2000, 43, 475-487), and DMAP (4-(dimethylamino)pyridine, 5.5 g, 45 mmol, 4 eq.). The reaction mixture was stirred at room temperature overnight, then diluted with dichloromethane, and washed with a saturated aqueous solution of $NaHCO_3$, 1N HCl, and brine subsequently. The organic layer was dried and concentrated to a colorless oil residue. Purification of the residual material (flash chromatography; using hexane/EtOAc, 95/5) gave the corresponding intermediate (5.7 g, 99%) as a colorless oil.

Step 2: The intermediate from step 1 (5.7 g, 11 mmol) was stirred in a mixture of THF-water-acetic acid (20 mL/20 mL/60 mL) at room temperature for 3 h; then the solvent was removed and the residue dried in vacuo. The residual material (the free alcohol) obtained was used in the next step without further purification Step 3: A solution of the alcohol (11 mmol, from step 2) in dichloromethane (125 mL) was slowly added to a suspension of PCC (pyridinium chlorochromate, 5.0 g, 23 mmol, 2.1 eq.) in dry dichloromethane (125 mL). The reaction mixture was stirred at room temperature overnight. Solvent was evaporated and the residue was dissolved in a minimum amount of dichloromethane. The resulting dichloromethane solution was passed through a silica gel column using Hexane/EtOAc (50/50). Evaporation of the solvent gave the corresponding aldehyde as yellow oil which was directly used in the next step without further purification.

Step 4: A solution of 80% sodium chlorite (2.5 g, 28 mmol, 2.5 eq.) in water (10 mL) was added slowly to a solution of the aldehyde (11 mmol, form step 3) and sodium dihydrogen phosphate (818 mg, 6.8 mmol, 0.6 eq.) in acetonitrile (20 mL) and water (20 mL) at 0 LC. The mixture was stirred 1 h at 0 LC then at room temperature for 1 h. Sodium sulfite (1.5 g, 1 eq.) was added to decompose peroxides, and the pH was adjusted to 2 with 1N HCl solution. Reaction mixture was extracted twice with EtOAc. The organic layers were washed with brine, dried, and concentrated. Purification of the residual material (flash chromatography; $CH_2Cl_2/CH_3OH$, 100/0 to 95/5) gave the corresponding carboxylic acid (3.4 g, 73%) as a foam.

Step 5: EDC (908 mg, 4.75 mmol, 2 eq.) was added to a mixture of the carboxylic acid (1 g, 2 mmol; from step 4), 3-amino-1-propanesulfonic acid sodium salt (380 mg, 2.34 mmol) and a catalytic amount of DMAP in DMF (10 mL). The reaction mixture was stirred at room temperature overnight. Solvent was removed and the residue was dried in vacuo to provide the corresponding derivative of 3-amino-1-propanesulfonic acid which was used in the next step without further purification.

Step 6: Trifluoroacetic acid (5 mL) was added to a solution of the 3-amino-1-propanesulfonic acid derivative (2.4 mmol, from step 5) in dichloromethane (5 mL) at room temperature. The reaction mixture was stirred for 2 h, followed by evaporation of the solvent. The resulted residue was purified (preparative HPLC; acetonitrile/water, 5/95 to 70/30 in the presence of 0.01% TFA) to yield, after lyophilization, the title compound (0.3 g, 29%) as a white solid: $^1$H NMR (500 MHz, $D_2O$) δ 1.04 (d, J=7 Hz, 3H), 1.07 (d, J=7 Hz, 3H), 1.39 (s, 3H), 1.45 (s, 3H), 1.55-1.58 (m, 2H), 2.11 (s, 3H), 2.43 (s, 3H), 2.45-2.58 (m, 5H), 2.98-3.02 (m, 2H), 4.26 (d, J=4 Hz, 1H), 6.54 (d, J=1.5 Hz, 1H), 6.93 (d, J=1.5 Hz, 1H).

Procedure C

Preparation of Compound B14: 3-{[(3α,5β,7α,12α)-3,7,12-trihydroxy-24-oxo-cholan-24-yl]amino}-1-propanesulfonic acid

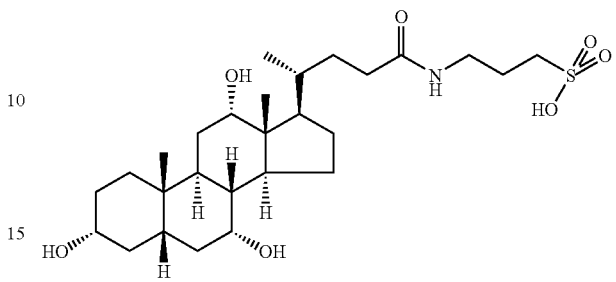

To a mixture of (+)-cholic acid (5.0 g, 12.2 mmol), 3-amino-1-propanesulfonic acid sodium salt (1.85 g, 11.5 mmol), 4-dimethylaminopyridine (72 mg, 0.6 mmol) in DMF (30 mL) was added N-(3-dimethylaminopropyl)-N'-ethylcarbodiimide hydrochloride (EDC, 4.68 g, 24.4 mmol). The reaction mixture was stirred at room temperature overnight. The cloudy mixture was filtered through sintered glass before the solvent was evaporated to dryness under reduced pressure. The viscous residue was dissolved in water (30 mL). The solution was treated with Dowex Marathon C™ ion exchange resin (strongly acidic, 30 g, prewashed). The suspension was stirred for 15 minutes before the resin was removed by filtration. The filtrate was concentrated to dryness under reduced pressure and dried in vacuo. The residue was triturated with diethyl ether (1000 mL). The solid product was recovered by filtration and dried in vacuo. The crude product was purified by flash chromatography (Biotage™ SP1: 20-40% EtOH in $CH_2Cl_2$) and the corresponding fractions were collected and lyophilized, affording the title compound (178 mg, 3%); $^1$H NMR ($D_2O$, 500 MHz) δ ppm 0.73 (s, 3H), 0.93 (s, 3H), 1.02 (m, 4H), 1.31 (m, 7H), 1.52 (d, 1H, J=14.5 Hz), 1.65 (m, 6H), 1.79 (m, 3H), 1.94 (m, 3H), 2.04 (m, 3H), 2.23 (m, 1H), 2.31 (m, 1H), 2.92 (m, 2H), 3.31 (m, 2H), 3.52 (m, 1H), 3.92 (s, 1H), 4.08 (s, 1H); $^{13}$C NMR ($D_2O$, 125 MHz) δ ppm 12.31, 16.82, 22.33, 23.12, 24.30, 26.48, 27.47, 27.95, 29.37, 31.87, 32.71, 34.06, 34.54, 35.09, 35.33, 38.15, 38.49, 39.50, 41.29, 41.64, 46.27, 46.28, 48.73, 68.33, 71.69, 73.14, 177.44; m/z ($ES^+$) 530; $[\alpha]_D$=+25.7°(c=0.005, water).

TABLE 7

Synthesis and characterization of exemplary non-amino acid amide prodrugs according to the invention

| ID | Synthetic procedure | Purifying protocol* | m/z ($ES^-$) (M − H, or M − Na)[†] |
|---|---|---|---|
| B1 | A | (a) | 320.4 |
| B2 | A | (a) | 306.5 |
| B3 | A | (b) | 280.2 |
| B4 | A | (c) | 280.3 |
| B5 | A | (b) | 238.0 |
| B6 | A | (b) | 525.0 |
| B7 | B | (a) | 441.3 |
| B9 | B | (a) | 491.4 |
| B10 | B | (a) | 457.3 |
| B11 | B** | (a) | 514.2 |
| B13 | B** | (a) | 548.1 |

*(a), HPLC; (b), precipitation; (c), flash chromatography; (d), filtration; (e), extraction;
**Procedure B, replacing 3-APS by N-glycyl-3-APS;
[†]the compounds were synthesized as acid form, or as sodium salt form.

Example 1-D

Chemical Synthesis of Carbohydrate-derived Prodrugs

Accordingly, the following examples are presented to illustrate how some carbohydrate-derived prodrugs according to the invention compounds may be prepared.

Synthesis of Compound S1 sodium salt

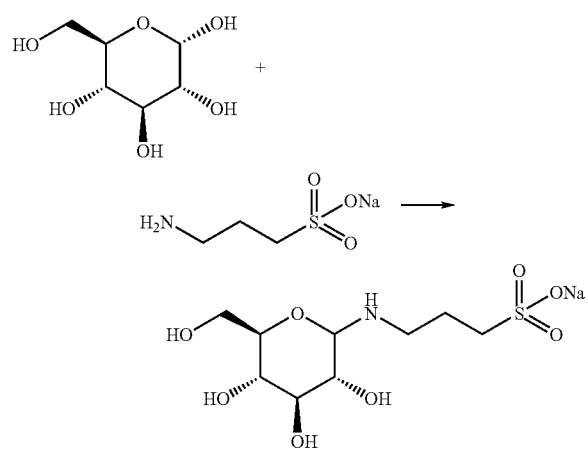

A suspension of glucose (2 g, 11.1 mmol) and the sodium salt of 3APS (2.24 g, 11.1 mmol) in MeOH (10 mL) was refluxed for 30 min before being cooled down to room temperature. After 24 h of stirring at room temperature, the solid was filtrated and washed twice with MeOH (2×10 mL). The resulting solid was dried overnight under high vacuum and afford the sodium salt of Compound Si (3.1 g, 9.6 mmol, 86%) as a white solid. $^1$H NMR (D$_2$O) (500 MHz) δ ppm 4.55 (d, J=4.4 Hz, 0.33H, α-anomer), 3.87 (d, J=9.3 Hz, 0.66H, α-anomer), 3.74 (dd, J=12.2, 1.5 Hz, 0.66H), 3.70 (dd, J=12.7, 2.4 Hz, 0.33H), 3.61 (dd, J=12.2, 4.9 Hz, 0.33H), 3.56 (dd, J=12.2, 5.4 Hz, 0.66H), 3.53-3.49 (m, 1H), 3.33 (t, J=9.3 Hz, 0.66H), 3.25-3.20 (m, 1H), 3.05 (t, J=8.8 Hz, 0.33H), 2.83 (m, 2.66H), 2.68 (m, 1H), 2.57 (m, 0.33H), 1.78 (m, 2H). m/z (ES$^-$) 300.0 (M-H).

Synthesis of Compound S2

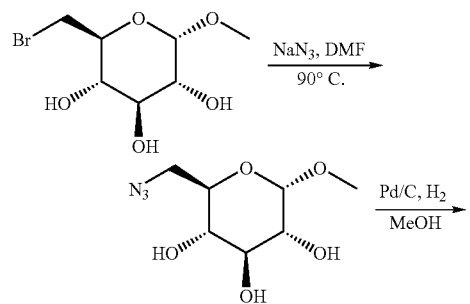

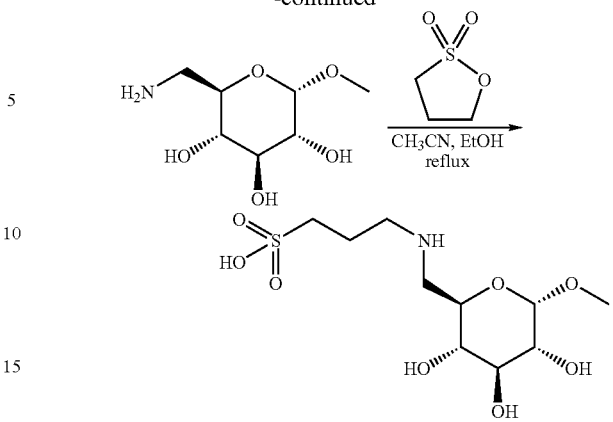

Methyl 6-bromo-6-deoxy-(x-D-glucopyranoside was prepared according to *Tetrahedron* 1991, 28(47), 5185-5192.

Step 1: A stirred suspension of bromide (1 g, 3.89 mmol) and sodium azide (278 mg, 4.28 mmol) in DMF (10 ml) was stirred at 90° C. for 5 days. After being cooled down to room temperature, the solution was evaporated under vacuum and the residue was purify by chromatography on silica gel (CHCl$_3$/MeOH 95/5 to 70/30 linear gradient) to afford the desired azido (776 mg, 3.54 mmol, 91%) as a white solid.

Step 2: A solution of the previously prepared azido derivative (776 mg, 3.54 mmol) in MeOH (10 ml) was degazed with N$_2$ for 10 min before a suspension of 10% Pd/C (50 mg) in CHCl$_3$ was added. After being stirred 2 h under H$_2$ pressure (40 PSI), the solution was filtrated over a pad of Celite™ (MeOH) and evaporated under vacuum and afforded the desired amine (628 mg, 3.25 mmol, 92% crude) as a yellow oil. This compound was used in the next step without further purification.

Step 3: A solution of sultone (285 μl, 3.25 mmol) in CH$_3$CN (5 ml) was added drop wise (over 30 min) to a refluxing solution of the previously prepared amine (628 mg, 3.25 mmol) in a 2/1 mixture CH$_3$CN/EtOH (10 ml). The resulting solution was heated under reflux for 15 h before being cooled down to room temperature and evaporated under vacuum. The residue was purified by chromatography on silica gel (i-PrOH/H$_2$O (0.5% NH$_4$OH) 98/2 to 80/20 linear gradient). After Evaporation, the compound was passed through a C-8 pad (H$_2$O) and lyophilized and afforded Compound S2 (450 mg, 1.43 mmol, 44% over two steps) as a white solid. NMR $^1$H (D$_2$O) (500 MHz): 2.06 (m, 2H), 2.92 (t, J=7.0 Hz, 2H), 3.13 (m, 3H), 3.21 (t, J=9.5 Hz, 1H), 3.34 (s, 3H), 3.36 (dd, 12.5, 3 Hz, 1H), 3.48 (dd, J=9.5, 3.5 Hz, 1H), 3.56 (t, J=9.0 Hz, 1H), 3.77 (dt, J=9.0, 2.5 Hz, 1H), 4.74 (d, J=3.5 Hz, 1H). ES (MS) 314.1 (M-H). [α]$_D$=+86.3 (c 1.0, H$_2$O)

Procedure A: General procedure for the deprotection of 1,2,3,4- or 2,3,4,6-tetraacetate glucose derivative:

To a stirred solution of the protected glucose derivative was added enough of a solution of NaOMe (sodium methoxide, 0.5M in MeOH) in order to obtain a basic pH (8-9, pH paper). The resulting solution was stirred at room temperature until completion (the reactions were generally followed by MS) before addition of twice the initial volume of CH$_3$CN. The resulting solid was then filtrated and washed several time with CH$_3$CN, acetone and diethyl ether. The resulting solid was then passed trough a C8 column (0.5% NH$_4$OH in H$_2$O) and lyophilized to afford the desired compound.

Synthesis of Compounds S3 and S4

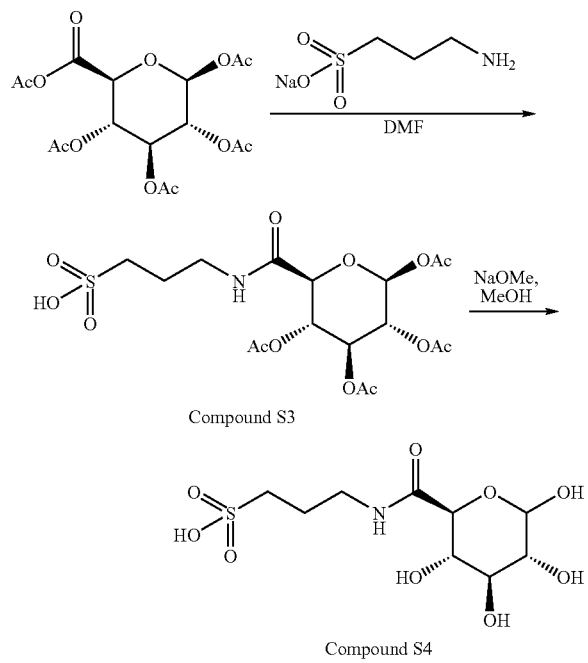

Compound S3

Compound S4

Step 1: A suspension of the sodium salt of 3-amino-1-propanesulfonic acid (398 mg, 2.47 mmol) and glucopyranuronic anhydride (398 mg, 2.47 mmol) in DMF (15 mL) was stirred 3 days at room temperature before evaporation of the solvent under vacuum. The residue was purified by chromatography on silica gel (CHCl$_3$/MeOH 100/0 to 70/30 linear) to afford compound S3 (719 mg, 1.49 mmol, 60%) as a white foam. $^1$H NMR (CD$_3$OD, 500 MHz) δ ppm 1.96 (m, 2H), 1.98 (s, 3H), 2.01 (s, 3H), 2.02 (s, 3H), 2.09 (s, 3H), 2.83 (m, 2H), 3.31 (m, 2H), 4.19 (d, J=9.5 Hz, 1H, H$_5$), 5.12 (t, J=8 Hz, 1H, H$_2$), 5.19 (t, J=10 Hz, 1H, H$_4$), 5.38 (t, J=9 Hz, 1H, H$_3$), 5.87 (d, J=8.5 Hz, 1H, H$_1$). m/z (ES) 482.4 (M-H); [α]$_D$=+6.2 (c 0.93, MeOH).

Step 2: Compound S3 (190 mg, 0.54 mmol) was treated according to Procedure A to afford Compound S4 (150 mg, 0.48 mmol, 88%) as a white solid. $^1$H NMR (D$_2$O, 500 MHz) δ ppm 1.92 (m, 2H), 2.90 (m, 2H), 3.27 (t, J=8.5 Hz, 0.5H), 3.32 (m, 2H), 3.47-3.50 (m, 1.5H), 3.56 (dd, J=9.5, 4.0 Hz, 0.5H), 3.69 (t, J=9.0 Hz, 0.5H), 3.86 (d, J=7.0 Hz, 0.5H), 4.16 (d, J=10.0 Hz, 0.5H), 4.6-4.7 (0.5H, under water peak), 5.25 (d, J=3.5 Hz, 0.5H); m/z (ES$^-$) 314.4 (M-H).

Synthesis of Compound S5 sodium salt and Compound S6 ammonium salt

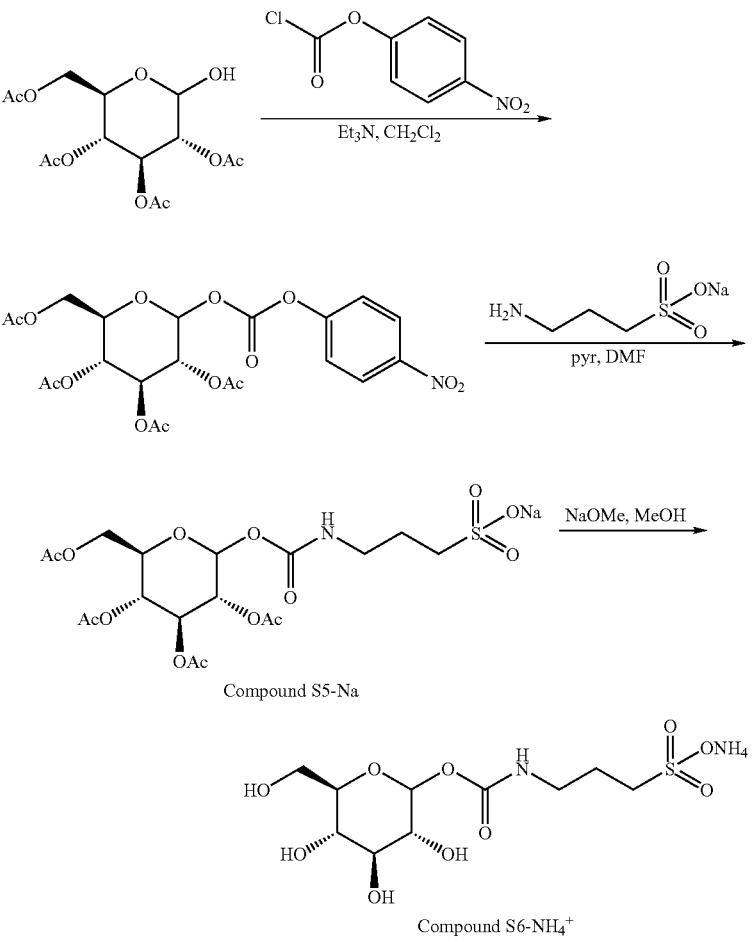

Compound S5-Na

Compound S6-NH$_4^+$ 2,3,4,6-Tetra-O-acetyl-D-glucose was prepared according to *J. Am. Chem. Soc.* 1993, 115, 2260-2267.

Step 1: p-nitrophenolchloroformate (638 mg, 3.16 mmol) was added to a stirred solution of tetraacetylglucose (1 g, 2.87 mmol) and Et$_3$N (800 µl, 5.74 mmol) in CH$_2$Cl$_2$ (20 ml) and the reaction was stirred overnight at room temperature. A 1N aqueous solution of hydrochloric acid (10 ml) was added and the layers were separated. The aqueous layer was extracted twice with CH$_2$Cl$_2$ (20 ml) and the combined organic layer were washed subsequently with a saturated solution of sodium carbonate (10 ml) and a saturated solution of sodium chloride. The organic layer was then dry over MgSO$_4$, filtrated and the solvent was evaporated under vacuum. The residue was purified by chromatography on silica gel (Hex/EtOAc 90/10 to 5050, linear gradient) to afford the desired carbonate (1.108 g, 2.16 mmol, 75%) as colorless solid.

Step 2: Pyridine (524 ml, 6.48 mmol) was added to a suspension of the carbonate previously prepared (1.108 g, 2.16 mmol) and the sodium salt of 3APS (522 mg, 2.16 mmol). After 3 days of stirring at room temperature, the solvent was evaporated under vacuum and the residue was purified by chromatography on silica gel (CHCl$_3$/MeOH 100/0 to 80/20, linear gradient) to afford Compound S5-Sodium salt (1.066 g, 2.07 mmol, 96%) as a white solid. $^1$H NMR (D$_2$O, 500 MHz) δ ppm 1.97 (s, 3H), 2.00 (s, 3H), 2.01 (s, 3H), 2.1 (m, 2H, hide), 2.05 (s, 3H), 2.83 (m, 2H), 3.25 (m, 2H), 3.98 (br d, J=8.0 Hz, 0.4H, H$_{5b}$), 4.09 (t, J=10.5 Hz, 1H, H$_6$), 4.17 (br d, J=10.2 Hz, 0.6H, H$_{5a}$), 4.26-4.30 (m, 1H, H$_6$), 4.99-5.12 (m, 2H, H$_{2a}$, H$_{2b}$, H$_{4b}$, H$_{4a}$), 5.32 (t, J=9.5 Hz, 0.40H, H$_{3b}$), 5.50 (t, J=9.9, 0.6H, H$_{3a}$), 5.69 (d, J=8.4 Hz, 0.3H, H$_{1b}$), 6.17 (d, J=3.5 Hz, 0.6H, H$_{1a}$). m/z (MS) 512.5 (M-H).

Step 3: Compound S5 sodium salt (500 mg, 0.97 mmol) was treated according to Procedure A to afford Compound S6-ammonium salt (220 mg, 0.64 mmol, 66%) as a white solid. $^1$H NMR (D$_2$O (500 MHz) δ ppm 1.80 (m, 2H), 2.80 (m, 2H), 3.15 (m, 2H), 3.30-3.37 (m, 1.5H), 3.41-3.43 (m, 1H), 3.68-3.53 (m, 3H), 3.75 (d, J=12.2 Hz, 0.5H), 5.26 (d, J=8.2 Hz, 0.5H, H$_{1b}$), 5.82 (d, J=3.05H2, 0.5H, H$_{1a}$). m/z (ES) 344.4 (M-H).

Synthesis of the Sodium Salt of Compound S7

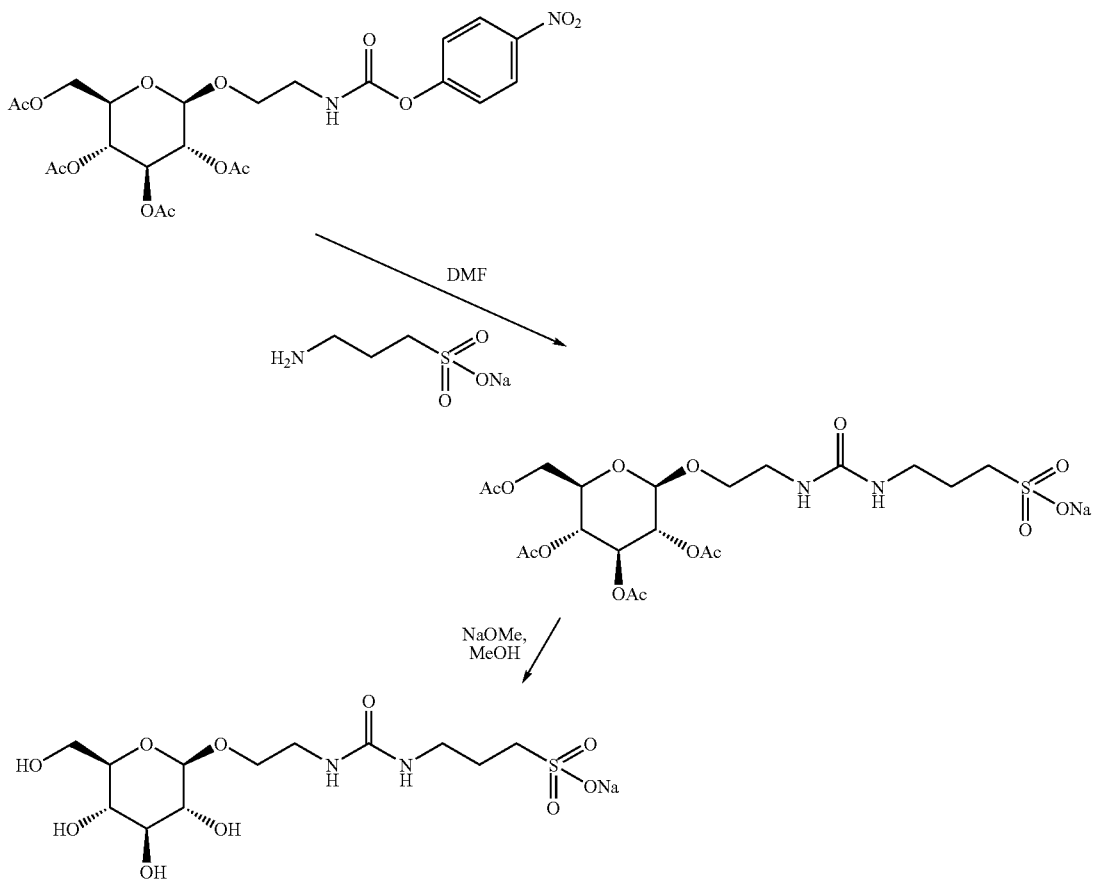

2-(p-nitrophenyl carbamate)-ethyl-2,3,4,6-tetra-O-acetyl-β-D-glucopyranoside was prepared according to *Org. Lett.* 2000, 2(8), 1093-1096.

Step 1: 3APS-sodium salt (223 mg, 1.38 mmol) was added to a stirring solution of p-nitrophenyl carbamate (643 mg, 1.16 mmol) in DMF (7 mL). After 24 h of stirring at room temperature, the solvent was evaporated under vacuum and the residue was purified by chromatography on silica gel (CHCl$_3$/MeOH 100/0 to 70/30, linear gradient) and afforded the desired sulfonate (596 mg, 1.07 mmol, 92%) as a white solid.

Step 2: The 2,3,4,6-tetra-O-acetyl-D-glucose previously prepared (596 mg, 1.07 mmol) was treated according to Procedure A to afford Compound S7-sodium salt (260 mg, 0.67 mmol, 63%) as a white solid. $^1$H NMR (D$_2$O, 500 MHz) δ ppm 1.91 (m, 2H, H11), 2.93 (t, J=7.5 Hz, 2H, H12), 2.24 (t, J=6.0 Hz, H10), 3.28 (t, J=9.0 Hz, 1H, H2), 3.34 (m, 2H, H8), 3.38 (t, J=9.5 Hz, 1H, H4), 3.45 (m1, 1H, H6a), 3.49 (dd, J=9, 9 Hz, 1H, H3), 3.7-3.77 (m, 2H, H6a, H7a), 3.91 (apparent d, J=11.5 Hz, H5, H7b), 4.46 (d, J=8.0 Hz, H1). m/z (ES) 386.9 (M-H).

Step 2: Piperidine (2.7 mL, 27 mmol) was added to a stirred solution of previously prepared Fmoc serine derivative (1070 mg, 1.37 mmol) in DMF (15 mL). After stirred for 1 h, solvent was evaporated under reduced pressure. The residue was purified by chromatography on silica gel (CHCl$_3$/MeOH 100/0 to 75/25, linear gradient) to afford the desired amine Compound S8-sodium salt (350 mg, 0.63 mmol, 46%) as a white solid.

Synthesis of the sodium salt o
f Compounds S8 and S9

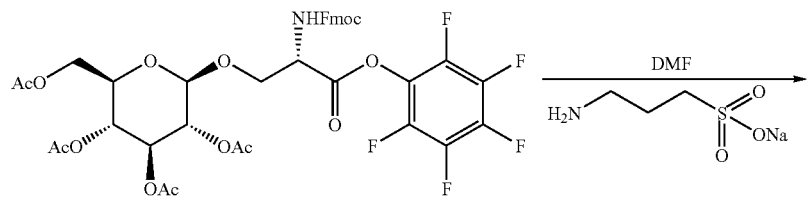

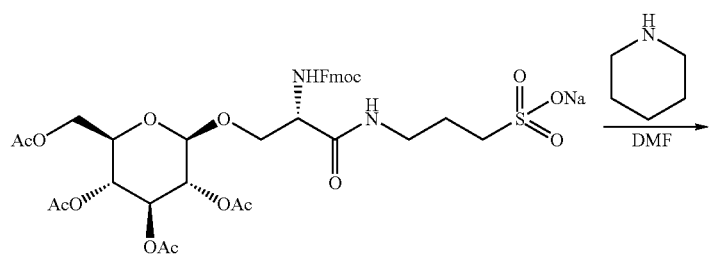

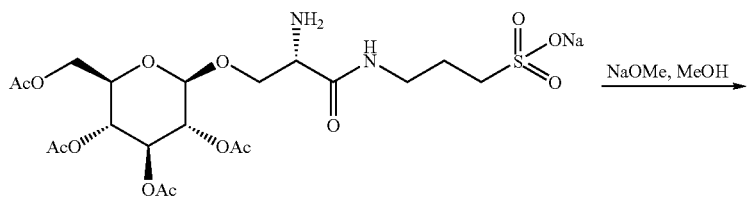

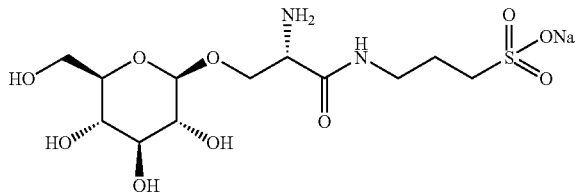

N-(9-Fluorenylmethoxycarbonyl)-3-O-(2,3,4,6-tetra-O-acetyl-β-D-glucopyranosyl)-L-serine Pentafluorophenyl ester was prepared according to J. Med. Chem. 1995, 38, 161-169.

Step 1: 3APS-sodium salt (258 mg, 1.60 mmol) was added to a stirring solution of pentafluorophenyl ester (1200 mg, 1.45 mmol) in DMF (15 mL). After 24 h of stirring at room temperature, the solvent was evaporated under vacuum and the residue was purified by chromatography on silica gel (CHCl$_3$/MeOH 100/0 to 80/20, linear gradient) to afford the desired sulfonate (1070 mg, 1.37 mmol, 94%) as a white solid.

Step 3: The 2,3,4,6-tetra-O-acetyl-D-glucose previously prepared (350 mg, 0.63 mmol) was treated according to Procedure A to afford Compound S9-sodium salt (210 mg, 0.54 mmol, 86%) as a white solid. $^1$H NMR (D$_2$O, 500 MHz) 1.95 (m, 2H, H11), 2.94 (t, J=8.0 Hz, 2H, H12), 3.35 (dd, J=7.5, 9.0 Hz, 1H, H2), 3.36-3.41 (m, 3H, H4, H10), 3.42-3.50 (m, 2H, H3, H5), 3.73 (dd, J=6.0, 1H, 12.0 Hz, H6a), 3.92 (br d, J=12.0 Hz, 1H, H6b), 3.96 (dd, J=4.5, 1H, 11.5 Hz, H8), 4.05 (t, J=4.5 Hz, 1H, H7a), 4.22 (dd, J=4.5, 11.5 Hz, 1H, H7), 4.47 (d, J=7.5 Hz, 1H, H1). m/z (ES) 387.25 (M-H).

Synthesis of the sodium salt of Compounds S14 and S15

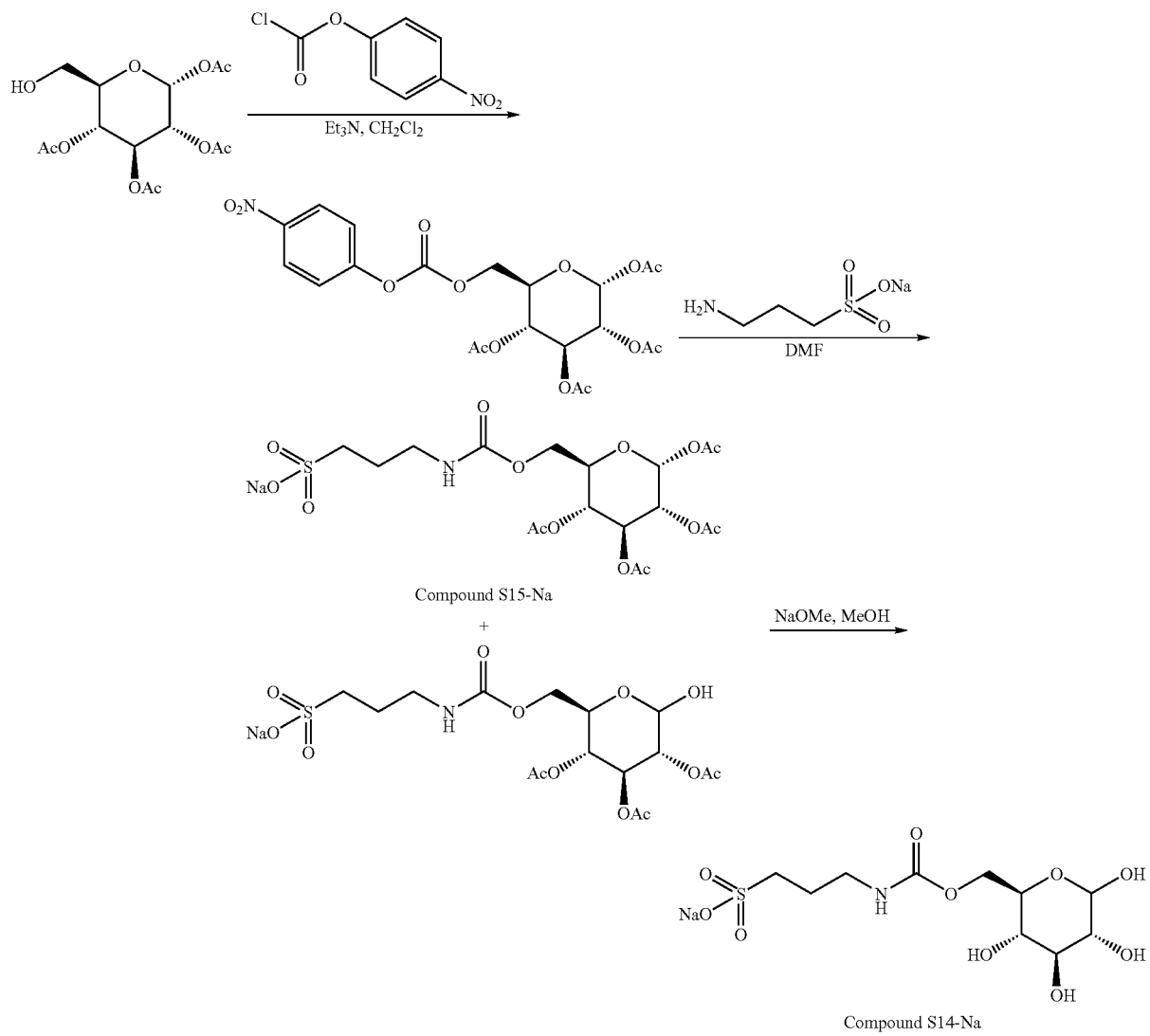

1,2,3,4-tetra-O-acetyl-α-D-glucopyranoside was prepared according to Org. Lett. 2006, 8, 2393-2396 and J. Am. Chem. Soc. 2000, 122, 12151-12157.

Step 1: p-Nitrophenolchloroformate (3 g, 14.8 mmol) was added to a stirred solution of 1,2,3,4-tetra-O-acetyl-α-D-glucopyranoside (4.7 g, 13.4 mmol) and triethylamine (3.7 ml, 26.8 mmol) in dichloromethane (100 mL). The reaction mixture was stirred overnight at room temperature. A 1N aqueous solution of hydrochloric acid (30 mL) was added and the layers were separated. The aqueous layer was extracted twice with dichloromethane (100 mL) and the combined organic layers were washed subsequently with a saturated solution of sodium carbonate (50 mL) and then with a saturated solution of sodium chloride. The organic layer was dried over magnesium sulfate, filtered and the solvent was evaporated under vacuum. The residue was purified by chromatography on silica gel (hexanes/ethyl acetate 90/10 to 50/50, linear gradient), affording the corresponding carbonate (4.7 g, 68%) as a colorless solid.

Step 2: The sodium salt of 3APS (2.22 g, 13.8 mmol) was added to a solution of the carbonate previously prepared (4.7 g, 9.16 mmol) in N,N-dimethylformamide (50 mL). After 3 days of stirring at room temperature, the solvent was evaporated under vacuum and the residue was purified by chromatography on silica gel (dichloromethane/methanol 100/0 to 70/30, linear gradient) and afforded Compound S15-sodium salt (1.95 g, 41%) as a white solid together with its 1-deactetylated derivative (1.21 g, 36%) as a white solid: $^1$H NMR ($D_2O$, 500 MHz) δ ppm 1.91-2.02 (m, 11H), 2.07 (s, 2H), 2.17 (s, 1H), 2.86 (m, 2H, H1), 3.24 (t, J=8.0 Hz, 2H, H3), 3.99 (m, 0.7H, $H_6$β), 4.10-4.20 (m, 2.3H, H5 and H6α), 5.02 (m, 1H, H9), 5.08 (t, J=10.0 Hz, 0.7H, $H_7$β), 5.13 (t, J=9.5 Hz, 0.3H, H7α), 5.34 (t, J=9.5 Hz, 0.7H, $H_8$β), 5.44 (t, J=9.5 Hz, 0.3H, H8α), 5.81 (d, J=8.0 Hz, 0.7H, $H_{10}$β), 6.28 (d, J=3.5 Hz, 0.3H, H10α); m/z (ES) 512.0 (M-H).

Step 3: Compound S15-sodium salt (1.37 g, 2.67 mmol)) was treated according to Procedure A to afford Compound S14-sodium salt (520 mg, 1.51 mmol, 56%) as a white solid: $^1$H NMR ($D_2O$, 500 MHz) δ ppm 1.80 (m, 2H, H2); 2.81 (m, 2H, H1), 3.12 (m, 2.55H, H3 and $H_9$β); 3.31 (m, 1H, H7α and $H_7$β); 3.36 (m, 0.55H, $H_8$β); 3.41 (dd, J=10.0, 4.0 Hz, 0.45H, H9α); 3.48 (m, 0.55H, $H_6$β); 3.56 (t, J=9.0 Hz, 0.45H, H8α); 3.84 (brd, J=10.0 Hz, 0.45H, H6α), 4.10 (m, 1H, H5a), 4.23 (apparent t, J=12.5 Hz, 1H, H5b), 4.51 (d, J=8.0 Hz, 0.55H, H10β); 5.08 (d, J=4.0 Hz, 0.45H, H10α); m/z (ES) 344.0 (M-H).

Synthesis of the sodium salt of Compounds S16 and S17

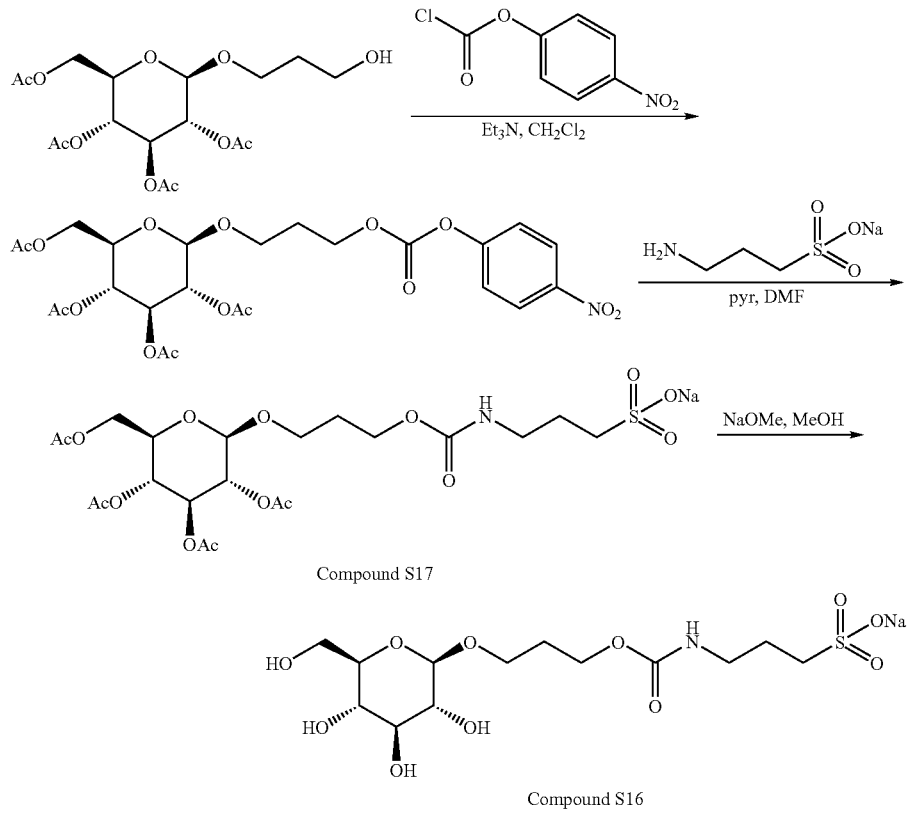

and p-nitrophenol (1.33 g) as a white solid, which was used in next step without further purification.

Step 3: The crude Compound S17 (1.33 g) was treated according to Procedure A to afford Compound S16-sodium salt (850 mg, 49% over two steps) as a white solid: $^1$H NMR (D$_2$O, 500 MHz) δ ppm 1.84-1.91 (m, 4H, H6+H2), 2.88 (m, 2H, H1), 3.18 (m, 2H, H3), 3.21 (t, J=8.5 Hz, 1H, H9), 3.33 (t, J=9.3 Hz, 1H, H11), 3.39 (m, 1H, H12), 3.44 (t, J=9.3 Hz, 1H, H10), 3.67 (dd, J=12.3, 5.8 Hz, 1H, H13a), 3.71 (m, 1H, H7a), 3.85 (dd, J=12.3, 2.0 Hz, 1H, H13b), 3.94 (m, 1H, H7b), 4.10 (m, 2H, H5), 4.39 (d, J=8.0 Hz, 1H, H8); m/z (ES) 402.1 (M-H).

2,3,4,6-Tetra-O-acetyl-D-glucose-1-propanol was prepared according to *J. Am. Chem. Soc.* 1940, 62, 917-920.

Step 1: p-Nitrophenolchloroformate (2.3 g, 11.4 mmol) was added to a stirred solution of 3-hydroxy-1-propyl 2,3,4,6-tetra-O-acetyl-β-D-glucopyranoside (3.1 g, 7.64 mmol) and triethylamine (2.12 mL, 11.44 mmol) in dichloromethane (60 mL) and the reaction mixture was stirred overnight at room temperature. Aqueous hydrochloric acid (1N, 15 mL) was added and the layers were separated. The aqueous layer was extracted 2 times with dichloromethane (40 mL) and the combined organic layer were washed subsequently with a saturated solution of sodium carbonate (15 mL) and then with a saturated solution of sodium chloride. The organic layer was then dried over magnesium sulfate, filtrated and the solvent was evaporated under vacuum. The residue was purified by chromatography on silica gel (hexanes/ethyl acetate 90/10 to 50/50, linear gradient) to afford the corresponding carbonate (3.1 g, 71%) as colorless solid.

Step 2: The sodium salt of 3-APS (655 mg, 4.07 mmol) was added to a solution of the carbonate previously prepared (1.55 g, 2.71 mmol) in N,N-dimethylformamide (50 mL). After 3 days of stirring at room temperature, the solvent was evaporated under vacuum and the residue was purified by chromatography on silica gel (dichloromethane/methanol 95/5 to 70/30, linear gradient) to afford a mixture of Compound S17

Example 1-E

Chemical Synthesis of Imine-Derived Prodrugs

Accordingly, the following examples are presented to illustrate how some imine-derived prodrugs according to the invention compounds may be prepared.

Synthesis of Compound M7 sodium salt

H$_2$N⁀⁀SO$_3$Na +

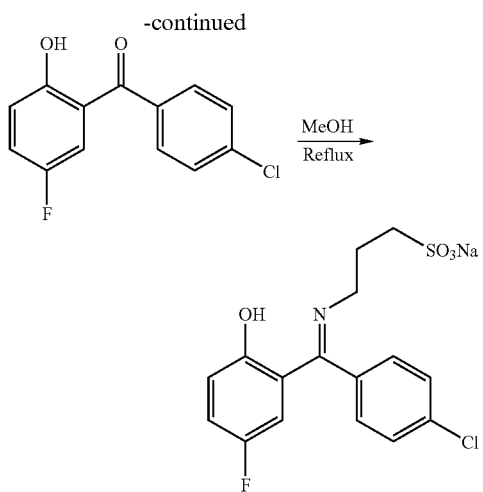

Sodium 3-amino-1-propanesulfonate (0.64 g, 4.0 mmol) was added to a solution of 4'-chloro-5-fluoro-2-hydroxy-benzophenone (0.50 g, 2.0 mmol) in methanol (50 mL). The reaction mixture was stirred under reflux for 4 h then concentrated under reduced pressure. The residual material was purified by flash chromatography (silica gel, chloroform:methanol 90:10 then 80:20) to afford the title compound (0.51 g, 64%): $^1$H NMR (CDCl$_3$, 500 MHz) δ 1.89 (m, 2H), 2.5 (t, J=7.0 Hz, 2H), 3.36 (t, J=7.0 Hz, 2H), 6.95 (m, 1H), 6.95 (m, 1H), 7.22 (m, 1H), 7.38 (d, J=8.0 Hz, 2H), 7.66 (d, J=8.0 Hz, 2H), 15.27 (s, 1H). ES-MS (370 M-1).

Synthesis of Compound M7-sulfonamide

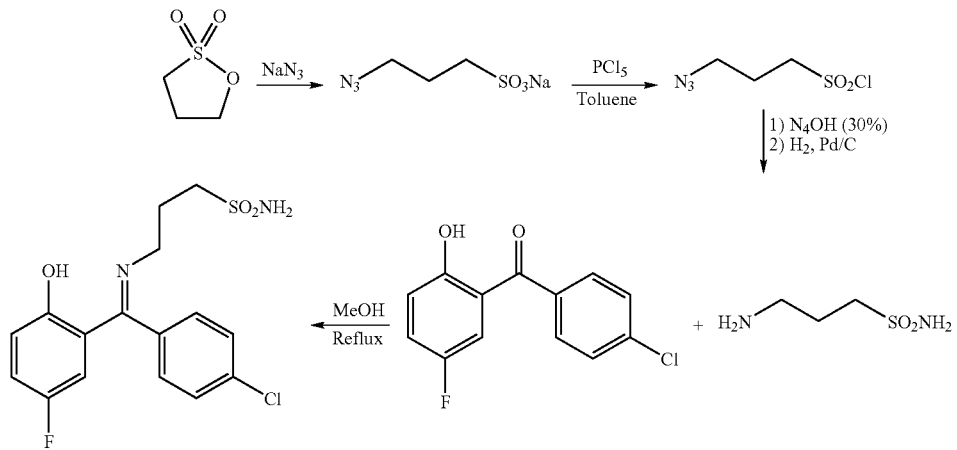

Step 1: To a stirred solution of sodium azide (3.5 g, 50 mmol) in water (25 mL) was added a solution of 1,3-propane sultone (6.1 g, 50 mmol) in acetone (25 mL). The reaction mixture was stirred at room temperature for 24 h then concentrated to dryness. The resulting solid was suspended in diethyl ether (100 mL) and stirred at reflux for 1 h. The suspension was cooled to room temperature and the solid was collected by filtration, washed with acetone and diethyl ether, and dried under vacuum, affording of 3-azido-1-propanesulfonic acid (7.6 g, 80%).

Step 2: PCl$_5$ (2.61 g, 12.53 mmol) was added to a suspension of 3-azido-1-propanesulfonic acid (2.07 g, 12.53 mmol) in toluene. The reaction mixture was stirred under reflux for 3 h. After cooling to room temperature, the solvent was evaporated, and the resulting material was used in the next step without further purification.

Step 3: Ammonium hydroxide (28%) (10 mL) was added to a solution of 3-azido-1-propanesulfonyl chloride (~2.29 g, 12.53 mmol; obtained in step 2) in ethanol (10 mL). The reaction mixture was stirred at room temperature for 3 h then concentrated. The residual material was passed through a short silica gel column using hexanes:ethyl acetate as eluent to isolate 3-azido-1-propanesulfonamide (1.5 g, 86%).

Step 4: 3-Azido-1-propanesulfonamide (1.5 g, 10.86 mmol; obtained from step 3) was dissolved in water/ethanol (10 mL/10 mL), followed by addition of 10% Pd/C (0.2 g). The resulting suspension was stirred under atmospheric pressure of H$_2$ for 5 h. The insoluble material was removed by filtration; and the filtrate was concentrated. The residual material was suspended in hydrogen. The suspension was filtered and the resulting solid was washed with ethanol and diethyl ether, dried under high vacuum, affording 3-amino-1-propanesulfonamide (1.2 g, 80%).

Step 5: 3-Amino-1-propanesulfonamide (0.55 g, 4 mmol; from step 4) was added to a solution of 4'-chloro-5-fluoro-2-hydroxy-benzophenone (1 g, 4 mmol) in methanol (50 mL). The reaction mixture was stirred under reflux for 5 h then concentrated under reduced pressure. The residual material was purified by column chromatography (silica gel, dichloromethane:methanol 90:10 then 80:20). The corresponding solid (after removal of solvent) was recrystallized in diethyl ether to afford 3-{[(1E)-(4-chlorophenyl)(5-fluoro-2-hydroxyphenyl)methylene]amino}propane-1-sulfonamide (0.75 g, 51%). $^1$H NMR (CDCl$_3$, 500 MHz) δ 2.21 (m, 2H), 3.24 (t, J=7.0 Hz, 2H), 3.47 (t, J=7.0H, 2H), 4.63 (bs, 2H), 6.93 (m, 1H), 6.95 (m, 1H), 7.04 (m, 1H), 7.13 (d, J=8.2 Hz, 2H), 7.54 (d, J=8.2 Hz, 2H), 14.71 (s, 1H). ES-MS (369 M-1).

Example 2

In vitro Stability and Metabolism

In vitro stability of exemplary prodrugs of the invention was tested in water, in an acidic aqueous solution (pH: 1.5), in PBS, in human and mouse microsomes, and in human and mouse whole blood.

A. Stability in Water, at pH: 1.5 and PBS

Stability of exemplary compounds was determined in water, aqueous acidic solution (pH 1.5, HCl) and PBS (phosphate buffered saline) solution using ESI-MS (electrospray ionization mass spectrometry) as the detecting instruments. In general a 2 pg/mL pro-drug solution containing 1 μg/ml IS (internal standard) was prepared and incubated for 60 min. For water stability the incubation was performed at room temperature and for stability in acidic solution and in buffer. The incubation temperature was 37° C. Samples were analyzed for prodrug content at time points 0 and 60 min. using MS. The % changes in peak area ratio after 60 minutes for each test compound tested are calculated using the average values from six replicate runs. The compounds tested included Compounds A1 to A19, Compounds B5 and B6 and Compounds C1 to C26. Except for C26 which was found unstable at pH 1.5 and in PBS, all other compounds were judged to be stable under all conditions tested with less than about 15%-20% concentration change after 60 minutes.

B. Metabolism in Mouse and Human Microsomes

Microsomal stability of Compounds A1, A2, A3, C17, C18 and C19 was determined in duplicate, in presence of pooled mouse or human liver microsomes for up to 60 minutes at 37° C. Briefly, microsomes were diluted to achieve a concentration of 1.0 mg/mL in PBS buffer (pH 7.4) containing 3 mM $MgCl_2$ and 1 mM EDTA. Compounds (10 μM) and microsomes were pre-incubated for a period of 5 minutes before the enzymatic reaction was started by addition of co-factors (1 mM NADPH and 2 mM UDPGA in PBS buffer). After a 1-hour incubation period, the reaction was stopped by the addition of ice cold acetonitrile. For time 0 samples, the reaction was stopped with acetonitrile before the addition of the co-factors. Analysis of extracted samples was achieved using HPLC with MS detection. Several types of HPLC columns and mobile phases were used depending of the polarity of the compound. The compound stability was determined by the % of compound remaining at 60 minutes (peak response of compound at 60 minutes/peak response at 0 minutes×100). Four of the compounds tested (three amino acid prodrugs A1, A2, A3, and the carbamate prodrug C19) were found stable, with over 90% of the compounds remaining after 60 minutes in presence of mouse or human microsomes (data not shown). Compound C17 was found less stable with between 20 and 35% of the prodrug remaining after 60 minutes in presence of mouse or human microsomes, while carbamate C18 showed moderate stability with between 75 and 80% of the prodrug remaining under the same conditions.

C. Mouse and Human Whole Blood Stability

Test compounds were incubated for a total of 240 minutes at 37° C. in whole mouse and whole human blood. The compounds were added at time-point 0 and sample aliquots were withdrawn at each time point (usually 0, 60 and 240 minutes). The samples were extracted using protein precipitation. Analysis of extracted samples was achieved using HPLC with MS detection. Several types of HPLC columns and mobile phase were used depending of the polarity of the compound. The compound stability was determined by the % of compound remaining at 240 minutes (peak response of compound at 240 minutes/peak response at 0 minutes×100). Results are summarized in Table 8.

TABLE 8

Stability in mouse and human whole blood

| ID | Blood stability (% of compound remaining after 240 min.) | |
| --- | --- | --- |
| | Human Blood | Mouse Blood |
| A1 | ND | + |
| A2 | ND | ++ |
| A3 | ND | ++ |
| A4 | + | +++ |
| A5 | + | + |
| A6 | ++ | + |
| A7 | +++ | +++ |
| A8 | + | ++ |
| A9 | +++ | +++ |
| A10 | ++ | ++ |
| A11 | +++ | +++ |
| A12 | +++ | +++ |
| A13 | +++ | +++ |
| A14 | +++ | +++ |
| A15 | ++ | + |
| A16 | +++ | ++ |
| A18 | + | + |
| A19 | + | + |
| B3 | +++ | ++ |
| B4 | +++ | +++ |
| B5 | +++ | +++ |
| B6 | +++ | +++ |
| C1 | + | + |
| C4 | +++ | ++ |
| C5 | + | + |
| C7 | +++ | + |
| C8 | +++ | +++ |
| C9 | ++ | ++ |
| C10 | + | + |
| C11 | +++ | +++ |
| C12 | ++ | + |
| C13 | + | + |
| C14 | +++ | ++ |
| C15 | ++ | + |
| C16 | ++ | + |
| C17 | ND | + |
| C18 | ND | + |
| C19 | ND | + |
| C20 | ++ | + |
| C21 | ++ | + |
| C22 | ++ | + |
| C23 | ++ | + |
| C24 | ++ | + |

+: <30%, ++: 30-75%, +++: >75%; ND: not determined

These data illustrate the use of these compounds as pro-drugs, as they are converted to 3APS in the blood.

Example 3

Pharmacokinetics in Mice

A. Bioavailability of Exemplary Compounds

Selected exemplary compounds were tested for bioavailability in mice. Bioavailability estimates are performed for 3APS after administration of molar equivalent the selected compounds. At a specific time point following drug administration, one blood sample (approximately 1 ml) is collected from each of 3 animals from the inferior vena cava. The animals are anesthetized with isoflurane before blood collection (approximately 45 sec). Samples are collected at 5, 30, 60, 120, 180, 240 and 360 min post intravenous administration and at 15, 30, 60, 120, 180, 240 and 360 min post oral administration. One animal is used to obtain a baseline sample (pre-dose sample). Blood samples are collected into Sarstedt™ micro tubes (EDTA KE/1.3 ml), kept on ice until centrifugation at 4° C. at a minimum speed of 3000 rpm (1620 G) for 10 min. Plasma samples are transferred into Eppendorf™ tubes, immediately placed on dry ice and stored at −80° C. Plasma samples are stored frozen at −20° C. pending analysis.

Compounds in mouse plasma are extracted using protein precipitation. Quantitation of 3APS in mouse plasma matrix is achieved using LC-MS detection. Sample concentration is calculated using a calibration curve. Bioavailability results are summarized in Table 9.

TABLE 9

Bioavailability of selected compounds in mice

| ID | Bioavailability (F) in mice *<br>(+: <25%, ++: 25-35%, +++: >35%) |
|---|---|
| A (3APS) | ++ |
| A1 | ++ |
| A2 | +++ |

B. PK Brain and Plasma Levels of Oral Compound A2 and 3-APS

Compounds A2 and 3-aminopropanesulfonic acid were tested for pharmacokinetic parameters in mice. Parmacokinetic parameters (Cmax, Tmax, T1/2, AUC) are evaluated for 3APS after administration of a molar equivalent of each compound. Blood samples (approximately 1 ml) and brain samples are collected from each of 3 animals at time points 5, 15, 30, minutes 1, 2, 4, 6, 12, and 24 hours. The results analyzed from plasma samples and brain homogenates are summarized in Table 10. Relative bioavailability (F %) of Compound A2 and 3-APS were respectively of 51% and to 32%. A 2-fold increase in plasma concentration (Cmax) of 3-APS was observed when orally administering Compound A2 compared to 3-APS. Brain concentration of 3-APS was observed after oral administration of 0.18 mmol/kg for Compound A2 whereas the concentration could not be quantified after oral administration of the same molar equivalent of 3-APS.

TABLE 10

PK data on 3-APS analysis following oral administration of 25 mg/kg
(0.18 mmol/kg) and 250 mg/kg (1.80 mmol/kg) equivalent of 3-APS

| | | Plasma | | | | Brain | | |
|---|---|---|---|---|---|---|---|---|
| ID | Dose (mmol/kg) | AUC | Cmax (ng/mL) | Tmax (h) | T½ (h) | AUC | Cmax (ng/mL) | Tmax (h) | T½ (h) |
| 3-APS | 0.18 | 6427 | 1768 | 0.5 | 4.9 | BLLQ | BLLQ | N/A | N/A |
| A2 | 0.18 | 10135 | 3435 | 0.5 | 2.8 | 557 | 148 | 2.0 | 3.9 |
| A2 | 1.80 | 140661 | 35451 | 0.5 | 2.8 | 9772 | 1068 | 2.0 | 12.4 |

BLLQ: below the lower limit of quantification
N/A: not applicable

TABLE 9-continued

Bioavailability of selected compounds in mice

| ID | Bioavailability (F) in mice *<br>(+: <25%, ++: 25-35%, +++: >35%) |
|---|---|
| A3 | + |
| A4 | +++ |
| A6 | ++ |
| A7 | +++ |
| A13 | +++ |
| A18 | +++ |
| C9 | + |
| C13 | + |
| C14 | + |
| C15 | + |
| C16 | + |
| C17 | + |
| C18 | + |
| C19 | ++ |
| C21 | + |
| C22 | + |
| C25 | + |

* Calculated from the concentration of 3APS, 6 hours after administration of the tested compound. The calculated F value represents the Ratio (in percentage) of the AUC p.o. of the compound tested over the AUC i.v. of 3APS, based on the observation of 3APS.

As shown in Table 9, all the compounds tested were capable of delivering measurable quantities of 3APS. Compounds A2, A4, A7 and A18 were helpful in increasing the bioavailability of 3APS suggesting that they were more readily absorbed than 3APS or were able to prevent first-pass metabolism of 3APS. Although not shown, Compounds A3, C13, C14, C16, C17, C21, C22 and C25 had a measured $T_{max}$ 4 times to 16 times longer that 3APS (0.25 h), suggesting a significant improvement in the pk profiles of 3APS using those compounds.

Example 4

Pharmacokinetic Analysis of 3APS and Associated Metabolism

Example 4A

Metabolic Profiling of $^{14}$C-3APS in Mice, Rats and Dogs

Three single dose studies were conducted in mice, rats and dogs to determine the metabolic profile of $^{14}$C-3APS in plasma, urine and feces. In the first study, twenty-seven male CD-1 mice received a single dose of 100 mg/kg (20 µCi/animal) of $^{14}$C-3APS by oral gavage. Blood samples (3 animals/time point) were collected for 12 hr following drug administration while urine and feces (3 animals/time point) samples were collected for 96 hr. In the second study, eight male Sprague-Dawley rats received a single dose of 100 mg/kg (50 µCi/animal) of $^{14}$C-3APS by oral gavage while in the third study, three male Beagle dogs received a single dose of 100 mg/kg (30 µCi/kg) of $^{14}$C-3APS by oral gavage. For the rat and dog studies, blood samples were collected for 24 hr following drug administration while urine and feces samples were collected for 72 hr. All samples were analyzed for total radioactivity using appropriate sample preparation procedures and scintillation counting. Plasma and urine samples were also analyzed for 3APS and 3APS metabolites (2-carboxyethanesulfonic acid, 3-hydroxy-1-propanesulfonic acid and 3-acetylamino-1-propanesulfonic acid) concentrations using qualified HPLC and MS/MS methods.

Following oral administration of 100 mg/kg $^{14}$C-3APS to mice and rats, mean maximum plasma concentrations of total radioactivity and 3APS were reached at approximately 30 minutes post-dose (Table 11). Thereafter, plasma concentrations of total radioactivity and 3APS declined in a multiphasic manner with apparent terminal half-lives of approximately 2 and 6 h for mice and rats, respectively. Mean maximum plasma concentration of 2-carboxyethanesulfonic acid was achieved at 120 to 240 h post-dose. Thereafter, plasma concentrations declined in a multi-phasic manner with an apparent terminal half-life of approximately 2 h and 4 h for mice and rats, respectively.

Following oral administration of 100 mg/kg $^{14}$C-3APS to dogs, maximum plasma concentration of total radioactivity and 3APS were reached at approximately 30 minutes post-dose, whereas maximum plasma concentration of 2-carboxyethanesulfonic acid was achieved at 720 minutes post-dose (Table 11). Thereafter, plasma concentrations of total radioactivity and 3APS declined in a multi-phasic manner. The mean apparent terminal half-lives were approximately 35 h and 5 h for total radioactivity and 3APS, respectively.

For all species, the majority of total radioactivity was associated with 3APS and 2-carboxyethanesulfonic acid (Table 12). Based on $AUC_{0-\infty}$ values, 3APS accounted for approximately 60% of total radioactivity while 2-carboxyethanesulfonic acid accounted for 30% in mice and rats. In dogs, 3APS accounted for approximately 54% of total radioactivity while 2-carboxyethanesulfonic acid accounted for approximately 67%. 3APS and 2-carboxyethanesulfonic acid $AUC_{0-\infty}$ constituted approximately 90% (mouse and rat) and approximately 121% (dog) of the total radioactivity indicating that 2-carboxyethanesulfonic acid is the major metabolite of 3APS in the mouse, rat and dog.

For all species, total radioactivity was quantitatively recovered in urine and feces with approximately 75 to 90% of the administered dose recovered in 72 h (rat and dog) or 96 h (mouse). The major route of excretion of total radioactivity was via urine. 114

On average, 60% of the dose was excreted in urine as total radioactivity in all species. Based on the total amount of radioactivity excreted in urine, approximately 30% was excreted as 3APS while 2-carboxyethanesulfonic acid accounted for another 63% to 77% in mouse and dog. In rats, 3APS and 2-carboxyethanesulfonic acid accounted for 59% and 62% of total radioactivity, respectively. On average the two metabolites 3-hydroxy-1-propanesulfonic acid and 3-acetylamino-1-propanesulfonic acid represented less than 3% of the total radioactivity in all species (Table 11). The urinary cumulative amount of 3APS and 2-carboxyethanesulfonic acid accounted for approximately 90 to 110% of that determined for total radioactivity, once again suggesting that 2-carboxyethanesulfonic acid is the major metabolite of 3APS in the mouse, rat and dog.

TABLE 11

Pharmacokinetic Parameters of Total Radioactivity, 3APS and 2-carboxyethanesulfonic acid Following Single Oral Administration of 100 mg/kg $^{14}$C-3APS in Mice, Rats and Dogs

| Parameter | Mouse[1] | Rat | Dog |
|---|---|---|---|
| Total Radioactivity | | | |
| $C_{max}$ (μmol eq/mL) | 0.126 | 0.228 | 0.249 |
| $T_{max}$ (min) | 30 | 30 | 31 |
| $AUC_{0-\tau}$ (μmol eq · min/mL) | 24.4 | 43.3 | 45.4 |
| $AUC_{\infty}$ (μmol eq · min/mL) | 25.0 | 45.2 | 108 |
| $T_{1/2}$ (h) | 2.14 | 6.02 | 35.7 |

TABLE 11-continued

Pharmacokinetic Parameters of Total Radioactivity, 3APS and 2-carboxyethanesulfonic acid Following Single Oral Administration of 100 mg/kg $^{14}$C-3APS in Mice, Rats and Dogs

| Parameter | Mouse[1] | Rat | Dog |
|---|---|---|---|
| 3APS | | | |
| $C_{max}$ (μmol/mL) | 0.0977 | 0.218 | 0.250 |
| $T_{max}$ (min) | 30 | 30 | 31 |
| $AUC_{0-\tau}$ (μmol · min/mL) | 15.5 | 26.7 | 24.5 |
| $AUC_{\infty}$ (μmol · min/mL) | 15.7 | 27.6 | 25.3 |
| $T_{1/2}$ (h) | 1.72 | 6.43 | 5.04 |
| 2-carboxyethanesulfonic acid | | | |
| $C_{max}$ (μmol/mL) | 0.018 | 0.0234 | 0.0312 |
| $T_{max}$ (min) | 120 | 240 | 720 |
| $AUC_{0-\tau}$ (μmol · min/mL) | 7.26 | 12.7 | 30.5 |
| $AUC_{\infty}$ (μmol · min/mL) | 7.56 | 13.6 | NC |
| $T_{1/2}$ (h) | 2.33 | 3.99 | NC |

[1]PK parameters were derived using the mean plasma concentration-time profiles
NC: Not calculated

TABLE 12

Percentage of 3APS, 2-carboxyethanesulfonic acid, 3-acetylamino-1-propanesulfonic acid and 3-hydroxy-1-propanesulfonic acid in Plasma and Urine Following Single Oral Administration of 100 mg/kg $^{14}$C-3APS in Mice, Rats and Dogs

| | | % of Total Radioactivity | | | |
|---|---|---|---|---|---|
| | | 3APS | 2-carboxyethane-sulfonic acid | 3-acetylamino-1-propane-sulfonic acid | 3-hydroxy-1-propane-sulfonic acid |
| Mouse | Plasma* | 63 | 30 | — | — |
| | Urine[†] | 30 | 62 | 3.1 | 0.4 |
| Rat | Plasma* | 61 | 30 | — | — |
| | Urine[†] | 59 | 62 | 2.3 | 0.3 |
| Dog | Plasma* | 54 | 67 | — | — |
| | Urine[†] | 29 | 77 | 0.01 | 0.3 |

*Calculated as [AUC0-∞ 3APS or metabolites/AUC total radioactivity)] (or using AUC0-t if AUC0-∞ could not be reliably estimated)
[†]Calculated as [Amount Excreted 3APS or metabolites/AUC total radioactivity)]

Example 4B

Absorption, Excretion and Plasma Kinetics of $^{14}$C-3APS in Humans

Following the identification of 3APS metabolites, plasma and urine samples from this human AME study were reanalyzed for 3APS and 3APS metabolite (2-carboxyethanesulfonic acid, 3-hydroxy-1-propanesulfonic acid and 3-acetylamino-1-propanesulfonic acid) concentrations using qualified HPLC and MS/MS methods to determine the metabolic profile of $^{14}$C-3APS in human.

Following oral administration of $^{14}$C-3APS to healthy subjects, maximum plasma concentration of total radioactivity and 3APS were reached at approximately 1 to 1.25 hours post-dose, whereas maximum plasma concentration of 2-carboxyethanesulfonic acid was achieved at 6.5 hours. In plasma, the majority of total radioactivity was associated with 3APS and 2-carboxyethanesulfonic acid. Based on $AUC_{0-\infty}$ values, 3APS accounted for approximately 48% of total radioactivity while 2-carboxyethanesulfonic acid accounted for 49%. 3APS and 2-carboxyethanesulfonic acid $AUC_{0-\infty}$ constituted approximately 97% of the total radioactivity indicating that 2-carboxyethanesulfonic acid is the major metabolite of 3APS in human plasma.

Based on the total amount of radioactivity excreted in urine, approximately 15% was excreted as 3APS while 2-carboxyethanesulfonic acid accounted for another 79%. The urinary cumulative amount of 3APS and 2-carboxyethanesulfonic acid accounted for approximately 94% of that determined for total radioactivity, once again suggesting that 2-carboxyethanesulfonic acid is the major metabolite of 3APS.

Using those data, it is possible to calculate a metabolite-to-parent ratio of the exposure of about 0.1 following IV administration and a ratio of 0.38 following oral administration. This higher metabolite-to-parent ratio of the exposure following oral administration when compared to IV is consistent with an intestinal first-pass metabolism.

TABLE 13

Comparison of Systemic Exposure of 3APS and 2-carboxyethanesulfonic acid versus Total Radioactivity following a Single IV and Oral Administration of 14C-3APS in Rats

| Animal | 3APS | $AUC_{0-\infty}$(nmol.h/mL)[#] 2-carboxyethane-sulfonic acid | Total Radioactivity | % (2-carboxyethane-sulfonic acid)* | % (3APS and 2-carboxyethane-sulfonic acid)** |
|---|---|---|---|---|---|
| IV | | | | | |
| 1001 | 1528 | 105 | 1625 | 6.5 | 100.5 |
| 1002 | 1420 | 144 | 1588 | 9.1 | 98.5 |
| 1003 | 1591 | 184 | 1883 | 9.8 | 94.3 |
| 1004 | 1147 | 125 | 1266 | 9.9 | 100.5 |
| Mean | 1422 | 140 | 1591 | 8.8 | 98.4 |
| ±SD | 196.2 | 33.7 | 253.0 | 1.60 | 2.93 |
| % CV | 13.8 | 24.1 | 15.9 | 18.1 | 2.98 |
| PO | | | | | |
| 3001 | 610 | 232 | 874 | 26.5 | 96.3 |
| 3002 | 539 | 153 | 714 | 21.4 | 96.9 |
| 3003 | 407 | 177 | 628 | 28.2 | 93.0 |
| 3004 | 471 | 229 | 781 | 29.3 | 89.6 |
| Mean | 507 | 198 | 749 | 26.4 | 94.0 |
| ±SD | 87.4 | 39.1 | 104 | 3.49 | 3.37 |
| % CV | 17.3 | 19.8 | 13.9 | 13.2 | 3.59 |

[#]$AUC_{0-\infty}$ expressed as nmol eq.h/mL for total radioactivity
*Calculated as [($AUC_{0-\infty}$ 2-carboxyethanesulfonic acid/AUC total radioactivity)*100]
**Calculated as [($AUC_{0-\infty}$ 3APS + $AUC_{0-\infty}$ 2-carboxyethanesulfonic acid)/AUC total radioactivity]*100

Example 4C

Comparative Pharmacokinetic Parameters of 3APS and 2-Carboxyethanesulfonic Acid Following a Single Oral and IV Administration of $^{14}$C-3APS to Rats The purpose of this study was to investigate the absorption, metabolism and excretion profiles of $^{14}$C-3APS following a single intravenous bolus and oral administration to rats. Thirty-six male Sprague-Dawley rats received a single 100 mg/kg (~50 µCi/animal) dose of $^{14}$C-3APS by an IV bolus injection (water or isotonic saline solution) and an additional 36 male rats received the same dose level by oral gavage (in water). Blood, urine, feces, brain and CSF samples were collected for up to 72 hr following dose administration. Plasma, urine, brain and CSF concentrations of 3APS and 2-carboxyethanesulfonic acid (3APS major metabolite) were measured using LC and MS/MS detection method. Plasma, urine, feces, brain and CSF samples were analyzed for total radioactivity using appropriate sample preparation procedures and scintillation counting.

Based on $AUC_{0-\infty}$ values, after IV administration, 3APS accounted for 89% of total radioactivity and 2-carboxyethanesulfonic acid only about 9%. On the other hand, after oral administration, 3APS accounted for about 68% of total radioactivity and 2-carboxyethanesulfonic acid about 26%.

Example 4D

Comparative Pharmacokinetics Parameters of 3APS and 2-carboxyethanesulfonic acid Following a Single Oral, Intravenous and Portal Administration of 3APS in Rats The purpose of this study was to compare the pharmacokinetic profile of 3APS following a single dose administration either orally, intravenously or into the portal vein to male Sprague-Dawley rats. The oral, intravenous and portal routes of administration were selected to determine the intestinal and hepatic first-pass effects in the rat. Three groups of 4 male Sprague-Dawley rats were assigned to receive a single dose of 250 mg/kg 3APS by different routes of administration. One group received 3APS as an IV bolus administration (in water or isotonic saline solution), one group by oral gavage (in water) and the last group via a catheter into the portal vein (in water or isotonic saline solution). Blood samples were collected for 24 hours following dose administration. Plasma concentrations of 3APS and 2-carboxyethanesulfonic acid (the major metabolite of 3APS) were determined using LC and MS/MS method.

Following oral administration, maximum plasma concentrations ($C_{max}$) were generally reached within 1 hour for 3APS and its bioavailability based on the $AUC_\infty$ was calculated to be about 38%.

The results obtained confirmed that there is an important metabolism of 3APS. More particularly, based on a comparison between the systemic exposures following hepatoportal and intravenous administrations, metabolism of 3APS associated with hepatic first-pass was estimated to be 24%. By comparison between the systemic exposures following oral and hepatoportal administrations, metabolism of 3APS associated with intestinal first-pass was estimated to be 43%. This study also showed that the oral administration of 3APS generated 50% more metabolite than the intravenous administration which is consistent with an intestinal first-pass metabolism.

Example 5

In vitro Metabolism of 3APS in Primary Rat Neuron Culture and Organotypic Hippocampal Slice Culture The metabolism of 3APS was also studied in vitro in different types of cellular models. In some cases, the metabolism of 3APS was compared with that of γ-amino butyric acid (GABA).

The results obtained demonstrated that incubation of 3APS (400 μM) in primary rat neuron culture media produced 2-carboxyethanesulfonic acid as a metabolite. The conversion of 3APS to 2-carboxyethanesulfonic acid was time-dependent and cell concentration-dependent. Incubation of 3APS (400 μM initial concentration) for six days in the cell culture media (containing 800,000 cells) produced with 48 μM of 2-carboxyethanesulfonic acid. Under the same experimental conditions, 5.4 μM succinic acid was detected starting from GABA (400 μM initial concentration).

The conversion of 3APS to 2-carboxyethanesulfonic acid in the primary neuron culture media was significantly inhibited by vigabatrin, the latter a classic GABA transaminase inhibitor. Nialamide, a monoamine oxidase inhibitor, also reduced the formation of 2-carboxyethanesulfonic acid (from 3APS) but to a lesser extent. In contrast, gabapentin (known to increase GABA concentration in the brain) had no significant effect on the conversion of 3APS to 2-carboxyethanesulfonic acid.

In another in vitro model employing organotypic hippocampal slice culture, the conversion of 3APS to 2-carboxyethanesulfonic acid was time-dependent. More than 60% of 3APS was converted to 2-carboxyethanesulfonic acid after 3-day incubation in the culture media. 2-carboxyethanesulfonic acid was also detected after incubation of 3APS in human hepatocyte (HepG2) culture media.

It is understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. A compound of Formula IV, or a pharmaceutically acceptable salt thereof:

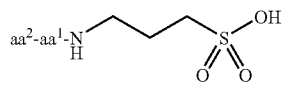

(IV)

wherein:
   $aa^1$ is valine, lysine, serine, alanine, isoleucine, histidine, or O-benzylserine, and
   $aa^2$ is valine, lysine, serine, alanine, isoleucine, histidine, O-benzylserine, or is absent.

2. The compound of claim 1, which is of Formula V, or a pharmaceutically acceptable salt thereof:

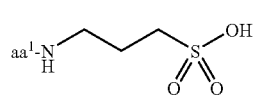

(V)

wherein $aa^1$ is valine, lysine, serine, alanine, isoleucine, histidine, or O-benzylserine.

3. The compound of claim 1, which is

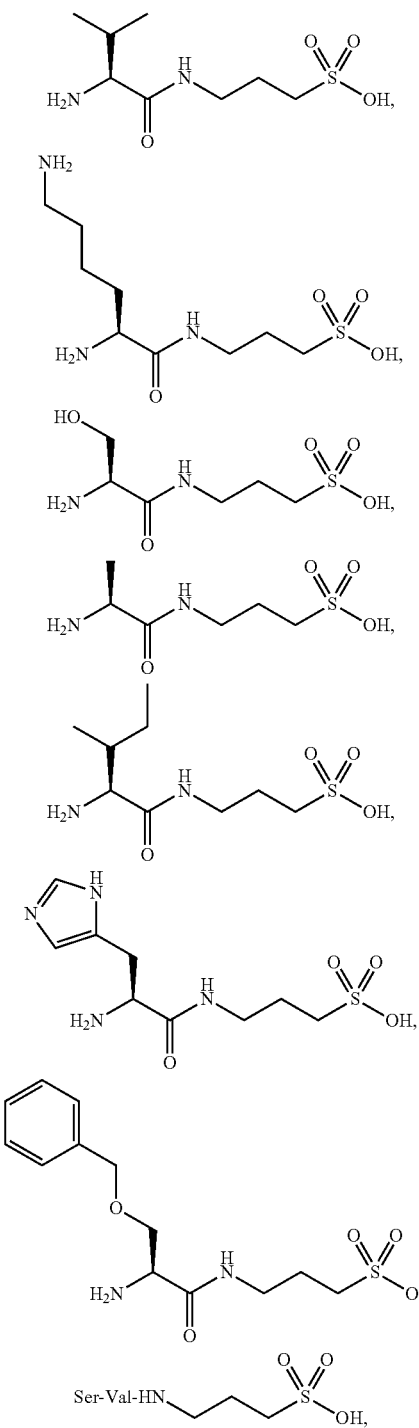

-continued

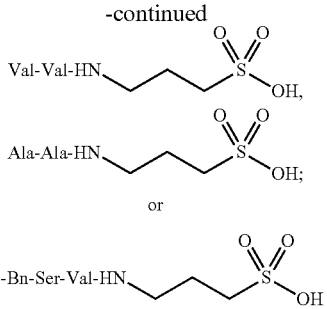

or a pharmaceutically acceptable salt thereof.

4. The compound of claim 1, which is

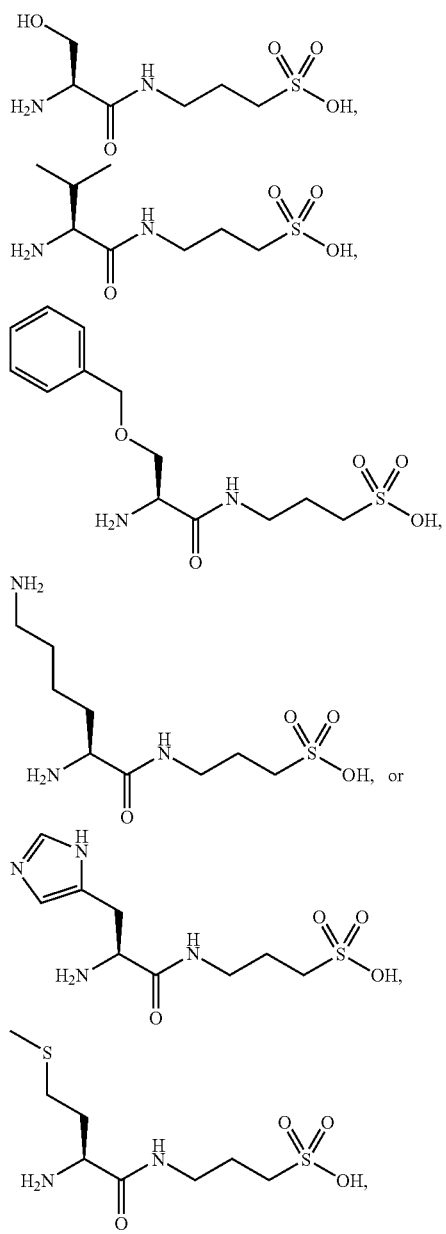

or a pharmaceutically acceptable salt thereof.

5. The compound of claim 1, which is

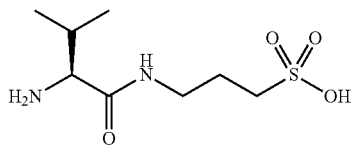

or a pharmaceutically acceptable salt thereof.

6. A pharmaceutical composition comprising a compound of claim 1 together with a pharmaceutically acceptable carrier.

7. A pharmaceutical composition comprising a compound of claim 1 together with a pharmaceutically acceptable carrier, which pharmaceutical composition is suitable for oral administration.

8. A pharmaceutical composition according to claim 7, which is in the form of a hard shell gelatin capsule, soft shell gelatin capsule, cachet, pill, tablet, lozenge, powder, granule, pellet, dragee, which is optionally enteric coated, a solution, an aqueous liquid suspension, a non-aqueous liquid suspension, an oil-in-water liquid emulsion, a water-in-oil liquid emulsion, an elixir, a syrup, or a pastille.

9. A pharmaceutical composition comprising a compound having the structure

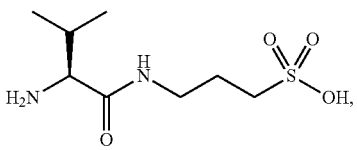

or a pharmaceutically acceptable salt thereof, with a pharmaceutically acceptable carrier.

10. A process for converting a compound of claim 1 to 3-amino-1-propanesulfonic acid (3APS) comprising contacting said compound with plasma, blood and/or brain cells whereby said compound is converted to 3APS.

11. A method for treating Alzheimer's disease, mild cognitive impairment, Down's syndrome, Hereditary Cerebral Hemorrhage with Amyloidosis of the Dutch-Type, cerebral amyloid angiopathy, a degenerative dementia, a dementia of mixed vascular and degenerative origin, dementia associated with Parkinson's disease, dementia associated with progressive supranuclear palsy, dementia associated with cortical basal degeneration, or diffuse Lewy body type of Alzheimer's disease, comprising administering a therapeutically effective amount of a compound of claim 1 to a human subject in need thereof.

12. The method according to claim 11, which is for treating Alzheimer's disease, mild cognitive impairment, cerebral amyloid angiopathy, or degenerative dementia.

13. The method according to claim 11, which is for treating Alzheimer's disease.

14. A method for treating Alzheimer's disease, mild cognitive impairment, Down's syndrome, Hereditary Cerebral Hemorrhage with Amyloidosis of the Dutch-Type, cerebral amyloid angiopathy, a degenerative dementia, a dementia of mixed vascular and degenerative origin, dementia associated with Parkinson's disease, dementia associated with progressive supranuclear palsy, dementia associated with cortical basal degeneration, or diffuse Lewy body type of Alzheimer's disease, comprising administering a therapeutically effective amount of a compound having the structure
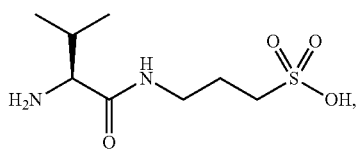
or a pharmaceutically acceptable salt thereof, to a human subject in need thereof.
* * * * *

UNITED STATES PATENT AND TRADEMARK OFFICE
CERTIFICATE OF CORRECTION

| | | |
|---|---|---|
| PATENT NO. | : 8,748,656 B2 | Page 1 of 1 |
| APPLICATION NO. | : 11/871639 | |
| DATED | : June 10, 2014 | |
| INVENTOR(S) | : Kong et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1204 days.

Signed and Sealed this
Sixteenth Day of August, 2016

Michelle K. Lee
*Director of the United States Patent and Trademark Office*